US008802634B2

(12) United States Patent
Watt et al.

(10) Patent No.: US 8,802,634 B2
(45) Date of Patent: Aug. 12, 2014

(54) CD40-L INHIBITORY PEPTIDES

(75) Inventors: Paul Michael Watt, Perth (AU); Richard Hopkins, Perth (AU); Katrin Hoffman, Aubin Grove (AU)

(73) Assignee: Phylogica Limited, Subiaco (AU)

( * ) Notice: Subject to any disclaimer, the term of this patent is extended or adjusted under 35 U.S.C. 154(b) by 165 days.

(21) Appl. No.: 13/003,726

(22) PCT Filed: Jul. 13, 2009

(86) PCT No.: PCT/AU2009/000896
§ 371 (c)(1),
(2), (4) Date: Sep. 2, 2011

(87) PCT Pub. No.: WO2010/003193
PCT Pub. Date: Jan. 14, 2010

(65) Prior Publication Data
US 2012/0065134 A1 Mar. 15, 2012

(30) Foreign Application Priority Data
Jul. 11, 2008 (AU) .................................. 2008903552

(51) Int. Cl.
*A61K 38/16* (2006.01)
*A61K 38/10* (2006.01)
*A61K 38/00* (2006.01)
*A61K 39/385* (2006.01)

(52) U.S. Cl.
USPC ..... 514/21.3; 514/21.4; 514/19.2; 424/185.1; 424/193.1; 530/324; 530/326

(58) Field of Classification Search
None
See application file for complete search history.

(56) References Cited

U.S. PATENT DOCUMENTS

| | | | |
|---|---|---|---|
| 7,122,187 B2 * | 10/2006 | Black et al. ................ | 424/154.1 |
| 2005/0181994 A1 * | 8/2005 | Chamberlain et al. .......... | 514/12 |
| 2006/0062784 A1 | 3/2006 | Grant et al. | |

FOREIGN PATENT DOCUMENTS

| WO | WO 02/089730 A2 | 11/2002 |
|---|---|---|
| WO | WO 2005/035570 A2 | 4/2005 |
| WO | WO 2009/071486 A1 | 6/2009 |

OTHER PUBLICATIONS

Kitagawa et al. 2005. Mod Rheumatol. 15:423-6.*
Kooten et al. 2000. J. Leukocyte Biol. 67:2-17.*
Daoussis et al. 2004. Clin and Diag Lab Immun. 11:635-641.*
Kitagawa et at (2005). Identification of three novel peptides that inhibit CD40-CD154 interaction. *Mod Rheumatol*, 15(6), 423-426.
Bianco et al. (2006). Solid-phase synthesis of CD40L mimetics. *Org Biomol Chem*, 4(8), 1461-1463.
Deambrosis et at (2009). Inhibition of CD40-CD154 costimulatory pathway by a cyclic peptide targeting CD154. *J Mol Med*, 87(2), 181-197.
NCBI RefSeq Accession No. YP_002086306.1. Retrieved from http://www.ncbi.nlm.nih.gov, 2009.
NCBI RefSeq Accession No. ZP_03411233.1. Retrieved from http://www.ncbi.nlm.nih.gov, 2008.
NCBI RefSeq Accession No. NP_952559.1. Retrieved from http://www.ncbi.nlm.nih.gov, 2009.
NCBI RefSeq Accession No. NP_388296.1. Retrieved from http://www.ncbi.nlm.nih.gov, 2009.
NCBI RefSeq Accession No. NP_636443.1. Retrieved from http://www.ncbi.nlm.nih.gov, 2009.
Howard et al. (Jan. 1999). Mechanisms of immunotherapeutic intervention by anti-CD40L (CD154) antibody in an animal model of multiple sclerosis. *The Journal of Clinical Investigation*, 103(2), 281-290.
Daoussis, Andonopoulos, & Liossis (Jul. 2004). Targeting CD40L: a promising therapeutic approach. *Clinical and Diagnostic Laboratory Immunology*, 11(4), 635-641.
van Kooten & Banchereau (Jan. 2000). CD40-CD40 ligand. *Journal of Leukocyte Biology*, 67(1), 2-17.
NCBI RefSeq Accession No. ZP_03245141.1. Retrieved from http://www.ncbi.nlm.nih.gov, 2010.
UniProtKB Accession No. B0L8W9. Retrieved from http://www.uniprot.org, 2008.
UniProtKB Accession No. B0L8W8. Retrieved from http://www.uniprot.org, 2008.
GenBank Accession No. ABR01095.1. Retrieved from http://www.ncbi.nlm.nih.gov, 2008.
GenBank Accession No. ABR01096.1. Retrieved from http://www.ncbi.nlm.nih.gov, 2008.
International Search Report, mailed Sep. 8, 2009 in connection with PCT International Application No. PCT/AU2009/000896, filed Jul. 13, 2009.
Written Opinion of the International Searching Authority, mailed Sep. 8, 2009 in connection with PCT International Application No. PCT/AU2009/000896, filed Jul. 13, 2009.
International Preliminary Report on Patentability (Chapter I of the Patent Cooperation Treaty), including Written Opinion of the International Searching Authority, issued Jan. 11, 2011 in connection with PCT International Application No. PCT/AU2009/000896, filed Jul. 13, 2009.

* cited by examiner

*Primary Examiner* — Shulamith H Shafer
(74) *Attorney, Agent, or Firm* — John P. White; Cooper & Dunham LLP

(57) ABSTRACT

The present invention provides compositions comprising peptidyl inhibitors of CD40L-dependent signalling that are not derived from a natural binding partner of CD40L such as CD40, or from a native CD40-CD40L interface. More particularly, the peptidyl inhibitors of the present invention are derived from natural sources that do not express CD40-CD40L costimulatory pathways. The invention also provides synthetic derivatives and analogs of the peptidyl inhibitors having enhanced binding affinity for CD40L or enhanced inhibitory activity relative to their par

CD40-L INHIBITORY PEPTIDES

CROSS-REFERENCE TO RELATED APPLICATIONS

This application is a §371 national stage application of PCT International Application No. PCT/AU2009/000896, filed Jul. 13, 2009, designating the United States and claims priority of Australian Patent Application No 2008903552, filed Jul. 11, 2009, the contents of all of which are hereby incorporated by reference into this application.

REFERENCE TO SEQUENCE LISTING

This application incorporates-by-reference nucleotide and/or amino acid sequences which are present in the file named "110721_2251_82422_Sequence_Listing_GC.txt," which is 17.8 kilobytes in size, and which was created Jul. 18, 2011 in the IBM-PC machine format, having an operating system compatibility with MS-Windows, which is contained in the text file filed Jul. 21, 2011 as part of this application.

FIELD OF THE INVENTION

The present invention relates to peptide-based compositions, analogs thereof and their use in medicine, for example in a method of diagnosis and/or prognosis and/or therapy of the human or animal body or in an ex vivo method of diagnosis and/or prognosis and/or therapy of the human or animal body.

BACKGROUND

Protein-Protein Interactions

The majority of biological processes in living organisms are mediated by proteins and their interactions with specific ligands e.g., other proteins, antigens, antibodies, nucleic acids, lipids and carbohydrates. Not only are such interactions involved in normal biological processes, protein interactions are also causative of processes involved in diseases or disorders. As a consequence, protein interactions are important targets for the development of new therapeutic compounds.

CD40 Ligand (CD40L or CD154) and CD40L Signaling Effects

CD40 ligand is a trimeric, transmembrane protein of the tumor necrosis factor family. A large variety of immunologic and vascular cells have been found to express CD40, CD40 ligand, or both.

For example, the CD40 ligand (CD40L or CD154), which is not expressed on resting human T cells, is up-regulated on the T-cell surface in response to foreign antigen presentation on MHC-class II molecules, up-regulation of the B7 antigen on the B-cell surface, formation of a complex between T-cells and B-cells via the T-cell receptor (TCR), and antigen recognition. Stimulation through the TCR also activates the T-cells, initiating T-cell cytokine production, interaction between the CD28 antigen on T-cells and the B7 antigen on B cells and binding of CD40L to CD40 receptor on the B-cell surface to thereby stimulate the B-cell to mature into a plasma cell secreting immunoglobulin.

The interaction between CD40L and the CD40 receptor may also cause adverse effects and transformed cells from patients with low-grade and high-grade B-cell lymphomas, B-cell acute lymphoblastic leukemia, multiple myeloma, chronic lymphocytic leukemia, and Hodgkin's disease express CD40. CD40 expression is also detected in two-thirds of acute myeloblastic leukemia cases and 50% of AIDS-related lymphomas. Immunoblastic B-cell lymphomas frequently arise in immune-compromized individuals such as allograft recipients and others receiving long-term immunosuppressive therapy, AIDS patients, and patients with primary immunodeficiency syndromes such as X-linked lymphoproliferative syndrome or Wiscott-Aldrich syndrome (Thomas et al., Adv. Cancer Res. 57, 329 (1991); Straus et al., Ann. Intern. Med. 118, 45 (1993). Malignant B cells from several tumors of B-cell lineage express a high degree of CD40 and appear to depend on CD40 signaling for survival and proliferation.

CD40-CD40L interactions may also promote immune-mediated angiogenesis, gut inflammation, acute intestinal injury or chronic intestinal injury, in the pathogenesis of inflammatory bowel disease (IBD). For example, the engagement of CD40L-activated HIF supernatants induce angiogenic events as determined by migration of HUMECs and tubule formation, both of which are inhibited using antibodies that bind to vascular endothelial growth factor (VEGF), interleukin-8 (IL-8) or hepatocyte growth factor (HGF). Additionally, CD40-deficient and CD40L-deficient mice are protected from DSS-induced colitis and display significant impairment of gut inflammation-driven angiogenesis, as determined by their microvascular density (Danese et al., Gut 56, 1248-1256, 2007).

CD40-CD40L interaction also activates extracellular signal-regulated kinase ½ and nuclear factor-KB pathways in insulinoma NIT-1 cells, and inhibitors of either pathway suppress cytokine/chemokine production in islets and up-regulate intercellular adhesion molecule-1 associated with inflammation, contributing to early islet graft loss after transplantation (Barbé-Tuana et al., Diabetes 55, 2437-2445, 2006).

Cell types typically resident in atherosclerotic plaques e.g., endothelial cells, macrophages and smooth muscle cells also express CD40L, and exposure to CD40L stimulates a broad inflammatory response in these cells such as heightened expression of pro-inflammatory cytokines, adhesion molecules, matrix degrading enzymes, and pro-coagulants, thereby leading to atherogenesis and lesion complication (Alderson et al., J Exp Med. 178, 669-674, 1993; Mach et al., Proc. Natl. Acad. Sci. USA 94, 1931-1936, 1997; Schonbeck et al., Circ Res. 89, 1092-1103, 2001; Mach et al., Nature 394, 200-203, 1998; Bavendiek et al., Arterioscler Thromb Vasc Biol. 25, 1244-1249, 2005). Animals that are deficient in CD40L have reduced levels of atherosclerosis on high-cholesterol diets and atherosclerotic lesions in such animals display features associated with plaque stability e.g., reduced macrophage count, reduced lipid content, increased collagen content (Lutgens et al., Nat. Med. 5, 1313-1316, 1999; Schonbeck et al., Proc. Natl. Acad. Sci. USA 97, 7458-7463, 2000). The soluble 18 kDa CD40L protein released from platelets on platelet activation may identify first or recurrent cardiovascular events, which further supports the pathogenic role of CD40L (Heeschen et al., N. Engl. J. Med. 348, 1104-1111, 2003; Schonbeck et al., Circulation 104, 2266-2268, 2001; Varo et al., Circulation 107, 2664-2669, 2003). Recently, Zirlik et al., Circulation 115, 1571-1580, 2007 demonstrated that CD40L interacts with Mac-1 on monocytes, and functionally enhances Mac-1 dependent monocyte adhesion and migration in vitro, and that inhibition of Mac-1 in vivo in LDLR−/− mice slows lesion development and macrophage accumulation in atherosclerotic plaques. Zirlik et al. suggest that the CD40L-Mac-1 interaction may participate, albeit not necessarily exclusively, in the expression of several pro-inflammatory cytokines including MIP-2, interleukin-1β, IL-8, pro-coagulant tissue factor, and in the activation of pro-inflammatory NF-κB. Thus, CD40L not only may attract inflammatory cells via Mac-1, but also induces the expression of a variety of pro-inflammatory and pro-oxidant functions that promote atherogenesis.

Elevated soluble CD40L is also prognostic of an increased risk of thrombosis and cardiac ischemia.

Modulators of Protein-Protein Interactions

To identify suitable therapeutic compounds, the pharmaceutical industry has particularly focussed on screening processes to identify antibodies, peptides and small molecule compounds capable of interacting with a protein and/or inhibiting a protein interaction. To function as a drug suitable for administration to a subject an antibody, peptide or small molecule must be capable of binding to a target with high affinity and selectivity.

Peptides offer significant advantages over antibodies in terms of uptake and low immunogenicity, and over small molecules in terms of reduced toxicity.

1. Molecular Shape Considerations

Often, small molecules and short peptides do not effectively modulate protein interactions because they do not generally possess a required shape e.g., to fit into complex protein surfaces or bind to relatively featureless interfaces. As a consequence, small-molecules ands short peptides are generally unable to bind to many surfaces of a target protein with sufficiently-high affinity and specificity to modulate binding of a ligand to the target, or to otherwise agonize or antagonize the activity of the target protein. Accordingly, there is a high attrition rate for the screening of such molecules as drug leads for therapeutic applications, particularly for targets such as protein interactions.

2. Random Peptides

By way of example, notwithstanding that short random peptides e.g., peptide aptamers, may be sufficiently small for commercial i.e., large-scale production by chemical synthesis, they generally provide highly-variable bioactivities against target proteins, and interactions with their targets are generally low affinity interactions. For example, in a screen of a random peptide library to identify a peptide capable of dissociating HIV protease fewer than about $1 \times 10^{-6}$ peptides displayed the desired activity (Park and Raines Nat. Biotechnol., 18: 548-550, 2000). This low "hit" rate appears to be a result of the inability of the such random peptides to assume stable secondary structure and/or tertiary structure to thereby facilitate binding to a target protein.

3. Structural Constraint

In response to the low "hit" rate for identifying new drug leads, the pharmaceutical industry has expended some effort in developing synthetic scaffolds for presenting ligands to proteins, with a view to modulating activity of the target protein. However, such constraint of random peptide libraries has failed to increase the "hit" rate for identifying new drug candidates based on random peptide sequences to a level that makes peptides a viable alternative to small molecules. For example, random peptides have been constrained within scaffold structures e.g., the active site loop of thioredoxin ("Trx"; Colas et al., Nature, 380: 548-550, 1996) and tested for binding to cyclin-dependent kinase-2 (Cdk-2), however fewer than $2 \times 10^{-5}$ of the Trx-constrained peptides actually blocked the target. Thus, the provision of synthetic scaffolds does not necessarily enhance "hit" rate. It is also possible that the limited repertoire of artificial scaffolds available to the industry will necessarily limit the diversity of structures that can be produced using such approaches, and may even mask or modify any native structures formed.

4. Secondary Structures, Domains, Sub-Domains and Folds

Native proteins have considerable structural features, including protein "domains" that are generally of functional significance. Until the present invention, such structural features have largely been utilized to determine evolutionary relationships between proteins, and for dissecting dynamic folding pathways i.e., how particular proteins fold. For example, the CATH database (Orengo et al., Structure 5, 1093-1108, 1997) classifies proteins according to a hierarchy of Class, Architecture, Topology and Homologous superfamily based upon structure, sequence, and functional considerations. In particular, the CATH hierarchy acknowledges three basic structural features i.e., class, architecture and topology. Protein "class" is highest in the CATH hierarchy and, in this context is a reference to the secondary structure composition and packing of a protein i.e., mainly α-helix, mainly β-strand, and α–β including alternating a/β in which the secondary structures alternate along the protein chain, and α+β in which the α and β regions are largely segregated. Thus, the "class" to which a protein belongs is a global assignment based on secondary structure considerations. Protein "architecture" refers to the overall shape of a protein based upon groups of similar secondary structural arrangements irrespective of the order in which they are connected in the protein. Protein "topology" describes the relative associations and orientations of secondary structures in 3D and the order in which they are connected. Protein "folds" are recognized in the CATH hierarchy as a function of topology, however the literature is confusing in this respect, because a fold can adopt a specific architecture e.g., Orengo and Thornton, Ann. Rev. Biochem. 74, 867-900, 2005.

As used herein, the term "fold" is therefore taken in its broadest context to mean a tertiary structure formed by the folding of multiple secondary structures including aspects of both architecture and topology. Herein, the term "subdomain" is used interchangeably with the term "fold". A "fold" may form independently or in association with other parts of a protein or other proteins or a scaffold structure.

Table 1 herein includes descriptions of segments of proteins comprising protein domains.

TABLE 1

Exemplary structures adopted by homologous superfamilies of proteins

| Structure | Architecture and/or topology of folds within proteins |
|---|---|
| α-helix | α-helices; folded leaf, partly opened |
| α-helix | 2α-helices; antiparallel hairpin, left-handed twist |
| α-helix | tandem repeat of two calcium-binding loop-helix motifs comprising α--helices |
| α-helix | helix-extended loop-helix; parallel α-helices |
| α-helix | 2α-helices: one short, one long; aromatic-rich interface |
| α-helix | 3α-helices; folded leaf, opened |
| α-helix | 3-α-helices; bundle, closed or partly opened, right-handed twist; up-and down |
| α-helix | 3-α-helices; bundle, closed or partly opened, right-handed twist; up-and down |
| α-helix | 3α-helices; bundle, right-handed twist |

TABLE 1-continued

Exemplary structures adopted by homologous superfamilies of proteins

| Structure | Architecture and/or topology of folds within proteins |
|---|---|
| α-helix | 3-4α-helices |
| α-helix | 3α-helices; architecture is similar to that of the "winged helix" fold |
| α-helix | 3α-helices; bundle, closed, left-handed twist; up-and-down |
| α-helix | 3α-helices; bundle, closed, left-handed twist; up-and-down; mirror topology to the spectrin-like fold |
| α-helix | 3α-helices; bundle, closed, right-handed twist; up-and-down |
| α-helix | 3α-helices; bundle, closed, left-handed twist, up-and-down |
| α-helix | core: 3α-helices; bundle, closed, left-handed twist; up-and-down |
| α-helix | 3α-helices; bundle, partly opened |
| α-helix | 3α-helices, the first one is shorter than the other two; bundle, partly opened |
| α-helix | 3 short α-helices; irregular array |
| α-helix | 3 short α-helices; irregular array |
| α-helix | 3α-helices; irregular array |
| α-helix | 3α-helices; irregular array; disulfide-rich |
| α-helix | α-helices; irregular array; disulfide-rich |
| α-helix | 3α-helices; irregular array |
| α-helix | 3α-helices; bundle, closed, right-handed twist; up-and-down |
| α-helix | 3α-helices; bundle, closed, left-handed twist; parallel |
| α-helix | 3α-helices; irregular array |
| α-helix | 3α-helices; long middle helix is flanked at each end with shorter ones |
| α-helix | 3α-helices; bundle, open |
| α-helix | α-helices; irregular array |
| α-helix | 4α-helices; bundle, closed or partly opened, left-handed twist; up-and-down |
| α-helix | 4α-helices; bundle, closed, right-handed twist; 1 crossover connection |
| α-helix | 4α-helices; bundle, closed, left-handed twist; 1 crossover connection |
| α-helix | 4α-helices; bundle, closed; left-handed twist; 2 crossover connections |
| α-helix | 4α-helices; bundle; one loop crosses over one side of the bundle |
| α-helix | 4α-helices, bundle; helix 3 is shorter than others; up-and-down |
| α-helix | 4α-helices; bundle; minor mirror variant of up-and-down topology |
| α-helix | 4α-helices; dimer of identical alpha-hairpin subunits; bundle, closed, left-handed twist |
| α-helix | 4α-helices; bundle, closed, right-handed twist |
| α-helix | 4α-helices; bundle, closed, right-handed twist |
| α-helix | 4α-helices; bundle, closed, right-handed twist |
| α-helix | 4α-helices; bundle, closed, left-handed twist |
| α-helix | 4α-helices; bundle, closed, right-handed twist |
| α-helix | 4α-helices; folded leaf, closed |
| α-helix | 4α-helices; orthogonal array |
| α-helix | 4α-helices; the long C-terminal helix protrudes from the domain and binds to DNA |
| α-helix | 4-α-helices; bundle, closed, left-handed twist; 2 crossover connections |
| α-helix | 4α-helices; array of 2 hairpins, opened |
| α-helix | 4α-helices: bundle |
| α-helix | 4α-helices: bundle |
| α-helix | 4α-helices: open bundle; capped by two small 3-stranded beta-sheets duplication: consists of two structural repeats |
| α-helix | 4α-helices: bundle; flanked by two short beta-hairpins duplication: consists of two structural repeats |
| α-helix | 4α-helices; array of 2 hairpins, opened |
| α-helix | 4 helices; bundle, closed, left-handed twist; right-handed super helix |
| α-helix | 4α-helices; bundle, left-handed twist; right-handed super helix |
| α-helix | 4α-helices; bundle, right-handed twist; right-handed super helix |
| α-helix | 4 long α-helices; bundle, left-handed twist (coiled coil); right-handed super helix |
| α-helix | 4α-helices; bundle, left-handed twist; left-handed super helix |
| α-helix | 4α-helices; bundle, right-handed twist; left-handed super helix |
| α-helix | 4α-helices; irregular array |
| α-helix | 2α-helices and adjacent loops |
| α-helix | 4α-helices; irregular array |
| α-helix | 4α-helices; irregular array |
| α-helix | 4α-helices; irregular array, disulfide-linked |
| α-helix | 4α-helices irregular array, disulfide-linked |
| α-helix | 4α-helices; irregular array, disulfide-linked |
| α-helix | 4α-helices; folded leaf; right-handed super helix |
| α-helix | 4α-helices; folded leaf; right-handed super helix |
| α-helix | 4α-helices; bundle |
| α-helix | 4 long α-helices; bundle |
| α-helix | 4 helices; bundle, partly opened |
| α-helix | core: 4α-helices; bundle, partly opened, capped with a beta-sheet |
| α-helix | 4α-helices, bundle |
| α-helix | 4 helices; the three last helices form a bundle similar to that of the RuvA C-domain |
| α-helix | 4α-helices; an orthogonal array |
| α-helix | 4α-helices; an orthogonal array |
| α-helix | 4α-helices; up-and-down bundle |
| α-helix | 4α-helices; open up-and-down bundle; binds alpha-helical peptides |
| α-helix | 4α-helices; open up-and-down bundle; flexible N-terminal tail |

TABLE 1-continued

Exemplary structures adopted by homologous superfamilies of proteins

| Structure | Architecture and/or topology of folds within proteins |
| --- | --- |
| α-helix | 4α-helices; array |
| α-helix | 4α-helices; bundle, closed, left-handed twist |
| α-helix | 4α-helices dimer of identical alpha-hairpin subunits; open bundle |
| α-helix | 4-5α-helices; bundle of two orthogonally packed alpha-hairpins |
| α-helix | 4-5α-helices; right-handed super helix |
| α-helix | 5α-helices; right-handed super helix; swapped dimer with the two long C-terminal helices |
| α-helix | α-helices array; two long helices form a hairpin that dimerizes into a 4-helical bundle |
| α-helix | 5α-helices; bundle, closed, left-handed twist |
| α-helix | 5α-helices; bundle, closed, left-handed twist |
| α-helix | 5α-helices; bundle, closed, left-handed twist; helices 2-5 adopt the Four-helical up-and-down bundle fold |
| α-helix | 5α-helices; bundle, closed, left-handed twist |
| α-helix | 5α-helices; folded leaf, closed |
| α-helix | 5α-helices; folded leaf, closed |
| α-helix | 5α-helices; folded leaf |
| α-helix | 5α-helices; irregular array; left-handed super helix |
| α-helix | 4-5α-helices; bundle; left-handed super helix |
| α-helix | 5α-helices; bundle |
| α-helix | 5α-helices; bundle |
| α-helix | α-helices; bundle |
| α-helix | 5α-helices; bundle |
| α-helix | α-helices; one helix is surrounded by the others |
| α-helix | 5α-helices; one helix is surrounded by the others |
| α-helix | 5α-helices; one helix is surrounded by the others |
| α-helix | 5α-helices; contains one more helix and a beta-hairpin outside the core |
| α-helix | 5α-helices: bundle |
| α-helix | α-helical bundle; up-and-down; right-handed twist |
| α-helix | 5α-helices: orthogonal array |
| α-helix | 5α-helices: orthogonal array |
| α-helix | 5α-helices: irregular array |
| α-helix | 5α-helices: array |
| α-helix | 5α-helices: orthogonal array; folding similarity to the TipA-S domain |
| α-helix | 5α-helices; array |
| α-helix | 6α-helices: bundle; left-handed twist, up-and-down topology |
| α-helix | 6α-helices, homodimer of 3-helical domains |
| α-helix | 6α-helices, homodimer of 3-helical domains |
| α-helix | 6α-helices, homodimer of 3-helical domains |
| α-helix | 6α-helices, heterodimer of 3-helical domains |
| α-helix | dimer of 3α-helical segments; consists of two subdomains: 4-helical bundle and coiled coil |
| α-helix | 6α-helices: closed bundle; greek-key; internal pseudo twofold symmetry |
| α-helix | 6α-helices: closed bundle; greek-key; internal pseudo twofold symmetry |
| α-helix | 6α-helices: bundle; one central helix is surrounded by 5 others |
| α-helix | 6α-helices: bundle; one central helix is surrounded by 5 others |
| α-helix | 6α-helices: array |
| α-helix | 6α-helices: orthogonal array |
| α-helix | irregular array of 6 short α-helices |
| α-helix | 6α-helices; one central helix is surrounded by 5 others |
| α-helix | 6α-helices; one central helix is surrounded by 5 others |
| α-helix | 6α-helices; bundle; one central helix is surrounded by 5 others |
| α-helix | Multiple α-helices |
| α-helix | Multihelical; core: 5-helical bundle |
| α-helix | multihelical; contains compact array of 6 short helices |
| α-helix | multihelical; irregular array of long and short helices |
| α-helix | multihelical; irregular array of long and short helices |
| α-helix | multihelical bundle; contains buried central helix |
| α-helix | multihelical; contains two buried central helices |
| α-helix | multihelical; can be divided into two subdomains |
| α-helix | multihelical; consists of two all-alpha subdomains contains a 4-helical bundle with left-handed twist and up-and-down topology |
| α-helix | multihelical; consists of two all-alpha subdomains each containing a 3-helical bundle with right-handed twist |
| α-helix | multihelical; consists of two all-alpha subdomains; contains a 4-helical bundle with left-handed twist and up-and-down topology |
| α-helix | multihelical; consists of two tightly associated 3-helical bundles with different twists |
| α-helix | multihelical; consists of two all-alpha subdomains; dimer |
| α-helix | multihelical; consists of two all-alpha subdomains |
| A-helix | multihelical; consists of two all-alpha domains |
| A-helix | multihelical; consists of two different 3-helical domains connected by a long, partly helical linker |
| α-helix | multihelical; consists of two different alpha-helical bundles (4-helical and 3-helical) |
| α-helix | multihelical; consists of two different alpha-helical bundles |

TABLE 1-continued

Exemplary structures adopted by homologous superfamilies of proteins

| Structure | Architecture and/or topology of folds within proteins |
|---|---|
| α-helix | multihelical; consists of two different alpha-helical bundles |
| α-helix | multihelical; consists of two different all-alpha subdomains, 4 helices each |
| α-helix | multihelical; consists of two all-alpha domains |
| α-helix | multihelical; consists of two all-alpha domains |
| α-helix | multihelical; consists of two all-alpha subdomains |
| α-helix | multihelical consists of two all-alpha subdomains subdomain 1 (residues 10-100) is a 4-helical bundle |
| α-helix | multihelical |
| α-helix | multihelical; consists of two all-alpha subdomains |
| α-helix | multihelical; common core is formed around two long antiparallel helices related by (pseudo) twofold symmetry |
| α-helix | multihelical |
| α-helix | multihelical; up to seven alpha-hairpins are arranged in closed circular array |
| α-helix | multihelical; consists of two all-alpha domains |
| α-helix | multihelical |
| α-helix | multihelical; forms intertwined dimer of identical 5-helical subunits |
| α-helix | multihelical; intertwined tetramer |
| α-helix | multihelical; intertwined trimer of identical 3-helical subunits |
| α-helix | multihelical; consists of two all-alpha domains |
| α-helix | multihelical; core: 5-helical bundle; binds cofactor at the beginning of third helix |
| α-helix | multihelical; contains a 3-helical bundle surrounded by several shorter helices |
| α-helix | multihelical; contains a 3-helical Hin recombinase-like subdomain and two long dimerisation helices |
| α-helix | multihelical oligomeric protein |
| α-helix | multihelical; consists of a conserved 4-helical core and a variable insert subdomain |
| α-helix | multihelical; consists of 2 all-alpha subdomains |
| α-helix | multihelical; consists of 2 all-alpha subdomains, "rigid" one and "mobile" one |
| α-helix | multihelical; consists of 2 all-alpha subdomains connected by a long helix |
| α-helix | multihelical; array of longer and shorter helices; contains an alpha-hairpin dimerisation subdomain |
| α-helix | multihelical; bundle of longer and shorter helices |
| α-helix | multihelical; three-helical bundle in the core is surrounded by non-conserved helices |
| α-helix | multihelical; consists of two subdomains |
| α-helix | multihelical |
| α-helix | multihelical |
| α-helix | multihelical; can be divided into an alpha-alpha super helix domain and a long alpha-hairpin dimerization domain |
| α-helix | multihelical; can be divided into three subdomains (neck, body and tail) |
| α-helix | multihelical; 2 (curved) layers: alpha/alpha; right-handed super helix |
| α-helix | multihelical |
| α-helix | multihelical; consists of two all-alpha subdomains |
| α-helix | multihelical; interlocked (homo)dimer |
| α-helix | multihelical; interlocked heterodimer with F-box proteins |
| α-helix | multihelical; interlocked heterodimer with the Skp1 dimerisation domain |
| α-helix | multihelical; 3 layers or orthogonally packed helices |
| α-helix | multihelical |
| α-helix | multihelical; consist of two subdomains |
| α-helix | multihelical; open array |
| α-helix | multihelical; 2 layers or orthogonally packed helices |
| α-helix | multihelical bundle; contains buried central helix |
| α-helix | multihelical; consists of two topologically similar alpha-helical bundles |
| α-helix | multihelical; consists of 2 four-helical bundles |
| α-helix | multihelical; one domain consists of two similar disulfide-linked subdomains |
| α-helix | multihelical, consists of three all-alpha domains |
| α-helix | multihelical, consists of three all-alpha domains |
| α-helix | multihelical; core: 8 helices (C-J) are arranged in 2 parallel layers |
| α-helix | multihelical; 8 helices arranged in 2 parallel layers |
| α-helix | multihelical; bundle |
| α-helix | multihelical; core: 6 helices, bundle |
| α-helix | multihelical; forms a boat-shaped protein shell around cofactors |
| α-helix | multihelical; bundle |
| α-helix | multihelical; contains 4-helical bundle and 2-helical arm |
| α-helix | multihelical; array |
| α-helix | multihelical; array |
| α-helix | multihelical; bundle |
| α-helix | multihelical; bundle |
| α-helix | multihelical; bundle |
| α-helix | multihelical; array |
| α-helix | common core: 2 helices, disulfide-linked, and a calcium-binding loop |
| α-helix | 5 helices: irregular disulfide-linked array; also contains a small beta-hairpin |
| α-helix | 5 helices: irregular disulfide-linked array; form homodimer |
| α-helix | 5 helices: irregular disulfide-linked array; topological similarity to the Fungal elicitin fold |
| α-helix | 6 helices: irregular non-globular array; also contains two small b-hairpins |

TABLE 1-continued

Exemplary structures adopted by homologous superfamilies of proteins

| Structure | Architecture and/or topology of folds within proteins |
|---|---|
| α-helix | 3 helices, non-globular array; forms interlocked heterodimers with its targets |
| α-helix | variable number of helices and little beta structure |
| β-sheet | sandwich; 7 strands in 2 sheets; greek-key |
| β-sheet | sandwich; 9 strands in 2 sheet; greek-key; subclass of immunoglobin-like fold |
| β-sheet | sandwich; 7 strands in 2 sheets, greek-key |
| β-sheet | sandwich; 6 strands in 2 sheets |
| β-sheet | sandwich; 6 strands in 2 sheets |
| β-sheet | sandwich; 6 strands in 2 sheets |
| β-sheet | six-stranded beta-sandwich, jelly-roll/greek-key topology |
| β-sheet | sandwich; 7 strands in 2 sheets, greek-key |
| β-sheet | sandwich; 7 strands in 2 sheets, greek-key; permutation of the immunoglobulin-like fold |
| β-sheet | sandwich; 8 strands in 2 sheets; greek-key |
| β-sheet | sandwich; 8 strands in 2 sheets; greek-key |
| β-sheet | sandwich; 8 strands in 2 sheets; meander |
| β-sheet | sandwich; 8 strands in 2 sheets; meander |
| β-sheet | sandwich; 8 strands in 2 sheets; jelly-roll; some members can have additional 1-2 strands |
| β-sheet | sandwich; 8 strands in 2 sheets; greek-key |
| β-sheet | sandwich; 8 strands in 2 sheets; complex topology |
| β-sheet | sandwich; 8 strands in 2 sheets; jelly-roll |
| β-sheet | sandwich; 8 strands in 2 sheets; jelly-roll; similarity to the Nucleoplasmin-like/VP fold |
| β-sheet | sandwich; 8 strands in 2 sheets; jelly-roll |
| β-sheet | sandwich; 8 strands in 2 sheets; jelly-roll |
| β-sheet | sandwich; 8 strands in 2 sheets; greek-key |
| β-sheet | beta-sandwich: 8 strands in 2 sheets |
| β-sheet | sandwich; 8 strands in 2 sheets; complex topology with the crossing loops |
| β-sheet | sandwich; 8 strands in 2 sheets; greek-key: partial topological similarity to immunoglobulin-like folds |
| β-sheet | sandwich; 8 strands in 2 sheets; greek-key: partial topological similarity to immunoglobulin-like folds |
| β-sheet | sandwich; 8 strands in 2 sheets; greek-key: partial topological similarity to immunoglobulin-like folds |
| β-sheet | sandwich; 9 strands in 2 sheets; jelly-roll |
| β-sheet | sandwich; 9 strands in 2 sheets; jelly-roll; form trimers |
| β-sheet | sandwich; 9 strands in 2 sheets; greek-key |
| β-sheet | sandwich; 9 strands in 2 sheets; greek-key |
| β-sheet | sandwich; 9 strands in 2 sheets; greek-key/jelly-roll |
| β-sheet | sandwich; 9 strands in 2 sheets; jelly-roll |
| β-sheet | sandwich; 9 strands in 2 sheets; greek-key; contains a few helices in loop regions |
| β-sheet | sandwich; 9 strands in 2 sheets; unusual topology with 2 crossover loops |
| β-sheet | sandwich, 10 strands in 2 sheets; greek-key |
| β-sheet | sandwich, 10 strands in 2 sheets; jelly-roll |
| β-sheet | sandwich, 10 strands in 2 sheets; jelly-roll |
| β-sheet | sandwich, 10 strands in 2 sheets; "folded meander" |
| β-sheet | sandwich, 10 strands in 2 sheets |
| β-sheet | sandwich; 11 strands in 2 sheets |
| β-sheet | sandwich; 11 strands in 2 sheets; greek-key |
| β-sheet | sandwich; 11 strands in 2 sheets; greek-key |
| β-sheet | sandwich; 14 strands in 2 sheets; greek-key |
| β-sheet | sandwich; 12-14 strands in 2 sheets; complex topology |
| β-sheet | sandwich; 18 strands in 2 sheets |
| β-sheet | duplication: two beta-sandwiches of similar topologies are fused together in a single three beta-sheet domain |
| β-sheet | consists of two beta-sandwich domains of similar topologies |
| β-sheet | consists of two different beta-sandwich domains of partial topological similarity to immunoglobulin-like folds |
| β-sheet | consists of two different beta-sandwich domains unrelated to other beta-sandwich folds |
| β-sheet | consists of two all-beta subdomains: conserved small domain has a rubredoxin-like fold; larger domain consists of 6 beta-stands packed in either sandwich of two 3-stranded sheets or closed barrel (n = 6; S = 8) |
| β-sheet | this fold is formed by three glycine-rich regions inserted into a small 8-stranded beta-sandwich |
| β-sheet | barrel, partly opened; $n^* = 4$, $S^* = 8$; meander |
| β-sheet | contains barrel, partly opened; $n^* = 4$, $S^* = 8$; meander |
| β-sheet | contains barrel, partly opened; $n^* = 4$, $S^* = 8$; meander; capped by alpha-helix |
| β-sheet | core: barrel, in some members open; $n^* = 4$, $S^* = 8$; meander |
| β-sheet | core: barrel, open; $n^* = 4$, $S^* = 8$; meander; SH3-like topology |
| β-sheet | core: barrel, open; $n^* = 4$, $S^* = 8$; meander; SH3-like topology; some similarity to the Sm-like fold |
| β-sheet | core: barrel, open; $n^* = 4$, $S^* = 8$; meander; SH3-like topology; some similarity to the Sm-like fold |
| β-sheet | core: barrel, closed; $n = 4$, $S = 8$; complex topology; helix-containing crossover connection |

TABLE 1-continued

Exemplary structures adopted by homologous superfamilies of proteins

| Structure | Architecture and/or topology of folds within proteins |
|---|---|
| β-sheet | barrel, closed; n = 5, S = 8, meander |
| β-sheet | barrel, closed or partly opened n = 5, S = 10 or S = 8; greek-key |
| β-sheet | core: barrel, partly opened; n* = 5, S* = 8; meander |
| β-sheet | barrel, closed; n = 6, S = 12; and a hairpin triplet; meander |
| β-sheet | barrel, closed; n = 6, S = 10; greek-key |
| β-sheet | barrel, closed; n = 6, S = 10; greek-key |
| β-sheet | barrel; n = 6, S = 10; greek-key |
| β-sheet | core: barrel; n = 6, S = 10; greek-key; topologically similar to the FMN-binding split barrel |
| β-sheet | segment-swapped dimer forming two identical conjoint barrels (n = 6, S = 10) topologically similar to the FMN-binding split barrel |
| β-sheet | barrel, open; n* = 6, S* = 10; greek-key |
| β-sheet | barrel, closed; n = 6, S = 8; greek-key |
| β-sheet | barrel; n = 6, S = 8, greek-key; similar to one trypsin-like protease barrel |
| β-sheet | barrel; n = 6, S = 8, greek-key |
| β-sheet | barrel, closed; n = 6, S = 8; greek-key |
| β-sheet | barrel, closed; n = 6, S = 8, greek-key, partial similarity to the OB-fold |
| β-sheet | barrel, closed; n = 6, S = 10, complex topology |
| β-sheet | core: barrel, closed; n = 6, S = 8; topology is similar to that of the acid proteases barrel |
| β-sheet | barrel, closed; n = 6, S = 8; a crossover loop topology |
| β-sheet | barrel, closed; n = 6, S = 10; complex topology with crossover (psi) loops |
| β-sheet | barrel, closed; n = 6, S = 10; complex topology |
| β-sheet | barrel, closed; n = 6, S = 10; meander; capped at both ends by alpha-helices |
| β-sheet | barrel, partly opened; n* = 6, S* = 12; meander; capped by an alpha-helix |
| β-sheet | barrel, closed; n = 6, S = 12; mixed beta-sheet |
| β-sheet | core: barrel, closed; n = 7, S = 8; complex topology |
| β-sheet | barrel, closed; n = 7, S = 10; complex topology |
| β-sheet | barrel, closed; n = 7, S = 10; order: 1234765; strands 1 and 5 are parallel to each other |
| β-sheet | barrel, closed; n = 7, S = 10; complex topology |
| β-sheet | barrel, closed; n = 7, S = 10; greek-key topology; one overside connection |
| β-sheet | barrel, closed; n = 7, S = 10; complex topology |
| β-sheet | core: barrel, closed; n = 7, S = 12; meander |
| β-sheet | barrel, closed or opened; n = 8, S = 12; meander |
| β-sheet | barrel, closed; n = 8, S = 10; meander |
| β-sheet | barrel, closed; n = 8, S = 10; complex topology |
| β-sheet | barrel, closed; n = 8, S = 10; one overside connection |
| β-sheet | barrel, closed; n = 8, S = 10; mixed sheet; two overside connections |
| β-sheet | barrel, partly open; n* = 8, S* = 10; one psi loop |
| β-sheet | dimer of two non-identical subunits; forms two similar barrels, n = 8, S = 10 each, that are fused together with the formation of third barrel, n = 6, S = 8 |
| β-sheet | consists of four 4-stranded beta-sheet motifs; meander |
| β-sheet | consists of five 4-stranded beta-sheet motifs; meander |
| β-sheet | consists of six 4-stranded beta-sheet motifs; meander |
| β-sheet | consists of seven 4-stranded beta-sheet motifs; meander |
| β-sheet | consists of eight 4-stranded beta-sheet motifs; meander |
| β-sheet | folded sheet; greek-key |
| β-sheet | core: 3-stranded meander beta-sheet |
| β-sheet | small mixed beta-sheet, 4 "generalized" strands |
| β-sheet | coiled antiparallel beta-sheet of 5 strands, order 51324; complex topology, crossing loops |
| β-sheet | twisted meander beta-sheet of 6 strands |
| β-sheet | core: twisted 7-stranded beta-sheet (half-barrel) of complex topology |
| β-sheet | core: twisted 7-stranded beta-sheet (half-barrel) |
| β-sheet | single sheet; 10 strands |
| β-sheet | 11 stranded sheet partly folded in a corner-like structure filled with a few short helices |
| β-sheet | single sheet; 16 strands; meander |
| β-sheet | single sheet formed by beta-hairpin repeats; exposed on both sides in the middle |
| β-sheet | consists of 3 4-stranded sheets; strands are parallel to the 3-fold axis |
| β-sheet | consists of 3 4-stranded sheets; strands are perpendicular to the 3-fold axis |
| β-sheet | superhelix turns are made of parallel beta-strands and (short) turns |
| β-sheet | superhelix turns are made of parallel beta-strands and (short) turns |
| β-sheet | one turn of helix is made by two pairs of antiparallel strands linked with short turns |
| β-sheet | (homo)trimer; each chain donates 3 beta-strands per turn of the helix |
| β-sheet | trimer formed by the interlocking beta-hairpin repeat units |
| β-sheet | trimer; contains two different beta-prism-like domains connected by an linker subdomain of less regular structure |
| β-sheet | Trp-rich beta-hairpin repeat units form helical structures of 3 units per turn |
| β-sheet | sandwich of half-barrel shaped beta-sheets |
| β-sheet | double-stranded ribbon sharply bent in two places; the ribbon ends form incomplete barrel; jelly-roll |
| β-sheet | multisheet protein with a mixture of beta-sandwich and beta-prism features |
| β-sheet | multisheet protein containing partial beta-propeller and beta-sandwich regions |

TABLE 1-continued

Exemplary structures adopted by homologous superfamilies of proteins

| Structure | Architecture and/or topology of folds within proteins |
|---|---|
| β-sheet | multisheet protein with a mixture of beta-sandwich and beta-barrel features |
| β-sheet | complex fold made of five beta-hairpin units and a b-ribbon arc |
| β-sheet | complex fold made of several coiled beta-sheets; contains an SH3-like barrel |
| β-sheet | complex fold made of several coiled beta-sheets |
| β-sheet | complex fold made of several coiled beta-sheets |
| β-sheet | complex fold |
| β-sheet | complex fold; consists of two intertwined subdomains |
| β-sheet | complex fold |
| β-sheet | complex fold made of bifurcated and partly folded beta-sheet |
| β-sheet | complex fold made of bifurcated and coiled beta-sheets |
| β-sheet | complex fold made of bifurcated and coiled b-sheets |
| β-sheet | pseudobarrel; mixed sheet of 7 strand folded upon itself and "buckled" by two beta-turns |
| β-sheet | pseudobarrel; sandwich of two sheets packed at a positive interstrand angle and interconnected with many short turns |
| β-sheet | pseudobarrel; capped on both ends by alpha-helices |
| β-sheet | pseudobarrel; capped at one end by an alpha-helix |
| β-sheet | pseudobarrel; capped on both ends by alpha-helices |
| β-sheet | pseudobarrel; mixed folded sheet of 5 strands; order 13452; strand 1 and 3 are parallel to each other |
| β-sheet | pseudobarrel; some similarity to OB-fold |
| β-sheet | non-globular proline-rich hairpin |
| α/β | contains parallel beta-sheet barrel, closed; n = 8, S = 8; strand order 12345678 |
| α/β | core: 3 layers, a/b/a; parallel beta-sheet of 6 strands, order 321456 |
| α/β | core: 3 layers, b/b/a; central parallel beta-sheet of 5 strands, order 32145; top antiparallel beta-sheet of 3 strands, meander |
| α/β | 3 layers: a/b/a; parallel beta-sheet of 5 strands, order 32145; Rossmann-like |
| α/β | 3 layers: a/b/a; parallel beta-sheet of 5 strands, order 32145; incomplete Rossmann-like fold; binds UDP group |
| α/β | variant of beta/alpha barrel; parallel beta-sheet barrel, closed, n = 7, S = 8; strand order 1234567; some members may have fewer strands |
| α/β | contains: barrel, closed; n = 10, S = 10; accommodates a hairpin loop inside the barrel |
| α/β | 3 layers: b/b/a; the central sheet is parallel, and the other one is antiparallel; there are some variations in topology |
| α/β | 2 layers, a/b; parallel beta-sheet of 3 strands, order 123 |
| α/β | core: 3 layers, a/b/a; parallel beta-sheet of 4 strands, order 1234; structural similarity of the MurF and HprK extends beyond the core. |
| α/β | 2 curved layers, a/b; parallel beta-sheet; order 1234...N; there are sequence similarities between different superfamilies |
| α/β | core: three turns of irregular (beta-beta-alpha)n superhelix |
| α/β | core: 4 turns of a (beta-alpha)n superhelix |
| α/β | core: 4 turns of (beta-beta-alpha)n superhelix |
| α/β | 3 layers, a/b/a; core: parallel beta-sheet of 4 strands, order 2134 |
| α/β | 3 layers, a/b/a; core: parallel beta-sheet of 4 strands, order 2134 |
| α/β | 3 layers, a/b/a; core: parallel beta-sheet of 4 strands, order 2134 |
| α/β | 3 layers, a/b/a; core: parallel beta-sheet of 4 strands, order 2134 |
| α/β | 3 layers, a/b/a; parallel beta-sheet of 4 strands, order 2134 |
| α/β | 3 layers, a/b/a; core: parallel beta-sheet of 4 strands, order 2134 |
| α/β | core: 3 layers: a/b/a; parallel beta-sheet of 4 strands; 2134 |
| α/β | 3 layers, a/b/a; parallel beta-sheet of 4 strands, order 2134 |
| α/β | 3 layers, a/b/a; parallel beta-sheet of 4 strands, order 2134 |
| α/β | 3 layers, a/b/a; core: parallel beta-sheet of 4 strands, order 3214 |
| α/β | 3 layers, a/b/a; core: parallel beta-sheet of 4 strands, order 1423 |
| α/β | 3 layers, a/b/a; parallel beta-sheet of 5 strands, order 21345 |
| α/β | 3 layers, a/b/a; parallel beta-sheet of 5 strands, order 32145 |
| α/β | 3 layers, a/b/a; parallel beta-sheet of 5 strands, order 32145 |
| α/β | core: 3 layers, a/b/a; parallel beta-sheet of 5 strands, order 32145 |
| α/β | 3 layers, a/b/a; parallel beta-sheet of 5 strands, order 32145; Rossmann-like |
| α/β | 3 layers, a/b/a; parallel beta-sheet of 5 strands, order 32145; Rossmann-like |
| α/β | 3 layers: a/b/a, core: parallel beta-sheet of 5 strands, order 43215 |
| α/β | 3 layers, a/b/a, core: parallel beta-sheet of 5 strands, order 32145 |
| α/β | 3 layers: a/b/a, core: parallel beta-sheet of 5 strands, order 21354; topological similarity to a part of the arginase/deacetylase fold |
| α/β | core: 3 layers: a/b/a, parallel beta-sheet of 5 strands, order 21435; contains a deep trefoil knot |
| α/β | 3 layers: a/b/a; parallel or mixed beta-sheet of 4 to 6 strands |
| α/β | 3 layers: a/b/a; parallel beta-sheet of 6 strands, order 321456; Rossmann-like |
| α/β | 3 layers: a/b/a; parallel beta-sheet of 6 strands, order 321456 |
| α/β | 3 layers: a/b/a; parallel beta-sheet of 6 strands, order 321456 |
| α/β | 3 layers: a/b/a; parallel beta-sheet of 6 strands, order 321456; also contains a C-terminal alpha + beta subdomain |
| α/β | 3 layers: a/b/a; parallel beta-sheet of 6 strands, order 321456 |
| α/β | 3 layers: a/b/a; parallel beta-sheet of 6 strands, order 321456 |
| α/β | core: 3 layers: a/b/a; parallel or mixed beta-sheet of 6 strands, order 321456 |
| α/β | 3 layers: a/b/a; parallel beta-sheet of 6 strands, order 321456 |

TABLE 1-continued

Exemplary structures adopted by homologous superfamilies of proteins

| Structure | Architecture and/or topology of folds within proteins |
|---|---|
| α/β | 3 layers: a/b/a; parallel beta-sheet of 6 strands, order 432156 |
| α/β | 3 layers: a/b/a; parallel beta-sheet of 6 strands, order 342156 |
| α/β | 3 layers: a/b/a; parallel beta-sheet of 6 strands, order 213456 |
| α/β | 3 layers: a/b/a; parallel beta-sheet of 6 strands, order 213465 |
| α/β | 3 layers: a/b/a, parallel or mixed beta-sheets of variable sizes |
| α/β | 3 layers: a/b/a, parallel beta-sheet of 6 strands, order 324156 |
| α/β | 3 layers, a/b/a; parallel beta-sheet of 7 strands, order 7165243 |
| α/β | 3 layers: a/b/a, parallel beta-sheet of 7 strands, order 3214567 |
| α/β | 3 layers: a/b/a, parallel beta-sheet of 7 strands, order 4321567 |
| α/β | 3 layers: a/b/a, parallel beta-sheet of 7 strands, order 3421567 |
| α/β | 3 layers: a/b/a, parallel beta-sheet of 7 strands, order 2314567; left-handed crossover connection between strands 2 & 3 |
| α/β | core: 3 layers, a/b/a; parallel beta-sheet of 7 strands, order 2134756 |
| α/β | 3 layers: a/b/a, parallel beta-sheet of 8 strands, order 21387456 |
| α/β | 3 layers: a/b/a; parallel beta-sheet of 8 strands, order 54321678 |
| α/β | beta(2)-(alpha-beta)2-beta; 2 layers, a/b; mixed beta-sheet of 5 strands, order 12345; strands 1 & 5 are antiparallel to the rest |
| α/β | beta(2)-(alpha-beta)2-beta(3); 3 layers, a/b/b; some topological similarity to the N-terminal domain of MinC |
| α/β | core: 2 layers, a/b; mixed beta-sheet of 6 strands, order 324561; strands 3 & 6 are antiparallel to the rest |
| α/β | 3 layers: a/b/a; parallel beta-sheet of 4 strands, order 2134 |
| α/β | core: 3 layers, a/b/a; parallel beta-sheet of 4 strands, order 1423 |
| α/β | 3 layers: a/b/a; parallel beta-sheet of 5 strands, order 32451 |
| α/β | core: 3 layers, a/b/a; mixed beta-sheet of 4 strands, order 4312; strand 3 is antiparallel to the rest |
| α/β | 3 layers: a/b/a; mixed beta-sheet of 4 strands, order 2143, strand 4 is antiparallel to the rest |
| α/β | 3 layers: a/b/a; mixed beta-sheet of 5 strands, order 13245, strand 1 is antiparallel to the rest |
| α/β | 3 layers: a/b/a; mixed beta-sheet of 5 strands, order 32145, strand 5 is antiparallel to the rest |
| α/β | 3 layers: a/b/a; mixed beta-sheet of five strands, order 21345; strand 4 is antiparallel to the rest |
| α/β | core: 3 layers, b + a/b/a; the central mixed sheet of 5 strands: order 21534; strand 2 is antiparallel to the rest |
| α/β | core: 3 layers, a/b/a; mixed beta-sheet of 5 strands, order 12345; strands 2 &, in some families, 5 are antiparallel to the rest |
| α/β | Core: 3 layers: a/b/a; mixed beta-sheet of 5 strands, order 21345; strand 5 is antiparallel to the rest |
| α/β | 3 layers: a/b/a; mixed beta-sheet of 5 strands, order 21345; strand 5 is antiparallel to the rest |
| α/β | 3 layers: a/b/a; mixed beta-sheet of 5 strands, order 32145; strand 2 is antiparallel to the rest |
| α/β | core: 3 layers, a/b/a; mixed sheet of 5 strands: order 21354; strand 4 is antiparallel to the rest; contains crossover loops |
| α/β | 3 layers: a/b/a; mixed beta-sheet of 5 strands; order: 21354, strand 5 is antiparallel to the rest; permutation of the Phosphorylase/hydrolase-like fold |
| α/β | 3 layers: a/b/a; mixed beta-sheet of five strands, order 21345; strand 1 is antiparallel to the rest |
| α/β | 3 layers: a/b/a; mixed beta-sheet of 6 strands; order: 213546, strand 5 is antiparallel to the rest; topological similarity to the MogA-like family fold |
| α/β | 3 layers, a/b/a; core: mixed beta-sheet of 6 strands, order 213456, strand 6 is antiparallel to the rest |
| α/β | 3 layers: a/b/a; mixed beta-sheet of 6 strands, order 165243, strand 3 is antiparallel to the rest |
| α/β | 3 layers: a/b/a; mixed beta-sheet of 6 strands, order 126345; strand 1 is antiparallel to the rest |
| α/β | core: 3 layers, a/b/a; mixed beta-sheet of 6 strands, order 324156; strand 5 is antiparallel to the rest |
| α/β | core: 3 layers, a/b/a; mixed beta-sheet of 6 strands, order 321456; strand 3 is antiparallel to the rest |
| α/β | core: 3 layers, a/b/a; mixed beta-sheet of 6 strands, order 321456; strand 3 is antiparallel to the rest |
| α/β | 3 layers: a/b/a; mixed beta-sheet of 6 strands, order 231456; strand 3 is antiparallel to the rest |
| α/β | 3 layers: a/b/a; mixed beta-sheet of 6 strands, order 251634; strand 6 is antiparallel to the rest |
| α/β | core: 3 layers, a/b/a; mixed beta-sheet of 6 strands, order 432156; strand 4 is antiparallel to the rest |
| α/β | core: 3 layers, a/b/a; mixed sheet of 7 strands, order 1237456; strands 1, 6 and 7 are antiparallel to the rest |
| α/β | 3 layers: a/b/a; mixed beta-sheet of 7 strands, order 3214567; strand 6 is antiparallel to the rest |
| α/β | core: 3 layers, a/b/a; mixed beta-sheet of 7 strands, order 3214576; strand 7 is antiparallel to the rest |

TABLE 1-continued

Exemplary structures adopted by homologous superfamilies of proteins

| Structure | Architecture and/or topology of folds within proteins |
|---|---|
| α/β | 3 layers, a/b/a; mixed beta-sheet of 7 strands, order 3214576; strand 7 is antiparallel to the rest; topological similarity to SAM-dependent methyltransferases |
| α/β | main domain: 3 layers: a/b/a, mixed beta-sheet of 7 strands, order 3245671; strand 7 is antiparallel to the rest |
| α/β | 3 layers: a/b/a; mixed beta-sheet of 7 strands, order 3214657; strand 6 is antiparallel to the rest |
| α/β | 3 layers: a/b/a; mixed beta-sheet of 8 strands, order 32145678; strands 6 and 8 are antiparallel to the rest |
| α/β | core: 3 layers, a/b/a; mixed beta-sheet of 8 strands, order 12435678, strand 2 is antiparallel to the rest |
| α/β | core: 3 layers, a/b/a; mixed beta-sheet of 8 strands, order 32145687; strand 7 is antiparallel to the rest |
| α/β | 3 layers: a/b/a; mixed beta-sheet of 8 strands, order 34251687; strand 8 is antiparallel to the rest |
| α/β | core: 3 layers: a/b/a; mixed beta-sheet of 8 strands, order 21345678, strand 7 is antiparallel to the rest |
| α/β | 3 layers: a/b/a; mixed (mainly parallel) beta-sheet of 8 strands, order 32145678; strand 8 is antiparallel to the rest |
| α/β | 3 layers: a/b/a; mixed (mainly parallel) beta-sheet of 8 strands, order 34215786; strand 8 is antiparallel to the rest |
| α/β | core: 3 layers: a/b/a; mixed beta-sheet of 8 strands, order 45321678, strands 4 and 5 are antiparallel to the rest |
| α/β | core: 3 layers: a/b/a; mixed beta-sheet of 8 strands, order 43516728, strand 7 is antiparallel to the rest |
| α/β | 3 layers: a/b/a; mixed beta-sheet of 8 strands, order 78612354; strands 3, 4 and 8 are antiparallel to the rest |
| α/β | 3 layers: a/b/a; mixed beta-sheet of 9 strands, order 918736452; strands 1, 2 and 8 are antiparallel to the rest |
| α/β | 3 layers: a/b/a; mixed (mostly antiparallel) beta-sheet of 9 strands, order 432159876; left-handed crossover between strands 4 and 5 |
| α/β | 3 layers: a/b/a; mixed beta-sheet of 9 strands, order 342156798; strands 3, 8 and 9 are antiparallel to the rest; left-handed crossover connection between strands 6 and 7 |
| α/β | consists of two intertwined (sub)domains related by pseudo dyad; duplication |
| α/β | possible duplication: the topologies of N- and C-terminal halves are similar; 3 layers: a/b/a; single mixed beta-sheet of 10 strands, order 213549A867 (A = 10); strands from 5 to 9 are antiparallel to the rest |
| α/β | consists of two similar domains related by pseudo dyad; duplication |
| α/β | consists of two similar domains related by pseudo dyad; duplication |
| α/β | 3 layers: a/b/a; parallel beta-sheet of 5 strands, order 21345 |
| α/β | contains of two similar intertwined domains related by pseudo dyad; duplication |
| α/β | consists of two similar domains with 3 layers (a/b/a) each; duplication |
| α/β | consists of three similar domains with 3 layers (a/b/a) each; duplication |
| α/β | consists of three similar domains with 3 layers (a/b/a) each; duplication |
| α/β | consists of two domains of similar topology, 3 layers (a/b/a) each |
| α/β | consists of two non-similar domains, 3 layers (a/b/a) each |
| α/β | consists of two non-similar domains with 3 layers (a/b/a) each |
| α/β | consists of two non-similar alpha/beta domains, 3 layers (a/b/a) each |
| α/β | consists of two non-similar domains, 3 layers (a/b/a) each |
| α/β | consists of two non-similar domains |
| α/β | consists of two non-similar domains |
| α/β | 2 different domains; d1: [core: 3 layers, a/b/a; parallel sheet of 5 strands, order: 2134]; D2: [2 layers, a/b; mixed sheet of 6 strands, order 321645; strands 2 and 6 are antiparallel to the rest] |
| α/β | consists of two non-similar domains |
| α/β | consists of two different alpha/beta domains; (1) of the Flavodoxin-like fold (scop_cf 52171); (2) similar to the Restriction endonuclease-like fold (scop_cf 52979), inserted into domain 1 |
| α/β | contains a P-loop NTP-binding motif; mixed beta-sheet folds into a barrel-like structure with helices packed on one side |
| α/β | contains mixed beta-sheets; topology is partly similar to that of the catalytic C-terminal domain |
| α/β | duplication: tandem repeat of two domains; 3 layers (a/b/a); parallel beta-sheet of 4 strands, order 2134 |
| α/β | consists of two similar intertwined domain with 3 layers (a/b/a) each: duplication |
| α/β | consists of two similar intertwined domain with 3 layers (a/b/a) each: duplication |
| α/β | consists of two similar domains related by pseudo dyad; duplication |
| α/β | consist of two intertwined domains; duplication: contains two structural repeats of alpha-beta-(beta-alpha)3 motif with mixed beta-sheet, order: 1432, strand 1 is antiparallel to the rest |
| α/β | consist of two intertwined domains; contains partial duplication |
| α/β | consist of two different alpha/beta domains; N-terminal domain has a SurE-like topology with a left-handed beta-alpha-beta unit |
| α/β | core: alpha-beta(2)-(alpha-beta)2; 3 layers (a/b/a); mixed beta-sheet of 4 strands, order 2134; strand 2 is antiparallel to the rest |

TABLE 1-continued

Exemplary structures adopted by homologous superfamilies of proteins

| Structure | Architecture and/or topology of folds within proteins |
|---|---|
| α/β | single helix packs against antiparallel beta-sheet |
| α/β | common alpha + beta motif for the active site region |
| α/β | consists of one alpha-helix and 4 strands of antiparallel beta-sheet and contains the catalytic triad Cys-His-Asn |
| α/β | core: (alpha)-beta-omega_loop-beta-alpha; embeded in larger different structures |
| α/β | contains long curved beta-sheet and 3 helices |
| α/β | beta-alpha-beta-alpha(2); antiparallel beta-ribbon |
| α/β | beta-alpha(2)-beta; antiparallel strands |
| α/β | alpha-beta(2)-alpha; antiparallel hairpin |
| α/β | alpha-beta(2)-alpha; 2 layers a/b; antiparallel beta-hairpin |
| α/β | alpha(3)-beta(2); antiparallel hairpin |
| α/β | beta(3)-alpha |
| α/β | beta(3)-alpha; 2 layers: alpha/beta |
| α/β | alpha1-beta3; 2 layers: alpha/beta; order 132 |
| α/β | beta-alpha-beta(2); 2 layers: alpha/beta; antiparallel beta-sheet: order 132 |
| α/β | beta-(alpha)-beta-alpha-beta(2); 3 layers: alpha/beta/alpha; antiparallel beta-sheet: order 1243 |
| α/β | beta-(2)-alpha(2)-beta(2); 2 layers: beta/alpha; antiparallel beta-sheet: order 1243; topological similarity to the common core of ribosomal proteins L23 and L15e |
| α/β | beta-(2)-alpha(3)-beta(2); 2 layers: beta/alpha; mixed beta-sheet: order 1234; stands 2 and 3 a parallel to each other |
| α/β | alpha-beta(3)-alpha-beta(2); 3 layers: alpha/beta/alpha |
| α/β | alpha-beta(3)-alpha-beta(2)-alpha; 2 layers: alpha/beta |
| α/β | beta(2)-alpha(2)-beta; 2 layers: 3-stranded antiparallel beta-sheet, order 213; HTH motif; also includes the extra N-terminal, DNA minor groove-binding helix |
| α/β | alpha-beta(4)-alpha-beta(2)-alpha; 2 layers: alpha/beta |
| α/β | beta(4)-alpha-beta(2)-alpha; 2 layers: alpha/beta; antiparallel beta-sheet, order: 651234 |
| α/β | core: beta(3)-alpha-beta-alpha; 2 layers: alpha/beta; left-handed crossover |
| α/β | core: beta(2)-alpha-beta(2); mixed beta-sheet 2143 |
| α/β | alpha + beta sandwich |
| α/β | Core: alpha-beta(4); helix packs against coiled antiparallel beta-sheet |
| α/β | alpha-beta-alpha-beta-alpha(2)-beta(3); antiparallel beta-sheet; order: 15432 |
| α/β | alpha(2)-beta(4)-alpha, 2 layers: alpha/beta, antiparallel beta sheet, meander |
| α/β | beta(3)-alpha-beta(2)-alpha; 2 layers, alpha/beta; antiparallel beta-sheet, order: 12543 |
| α/β | core: alpha-beta(3)-alpha, 2 layers: alpha/beta, three-stranded antiparallel beta sheet, strand order 123 |
| α/β | core: beta(2)-alpha(2), 2 layers: alpha/beta; long C-terminal helix forms dimeric parallel and tetrameric antiparallel coiled coils |
| α/β | helix-swapped dimer of beta(4)-alpha motifs |
| α/β | beta-BETA(2)-beta-alpha-beta(2); antiparallel sheet: order 2134 packed against helix and BETA-hairpin on the same side; irregular C-terminal tail |
| α/β | Dimeric |
| α/β | alpha-beta(4)-alpha(3); core: meander beta-sheet plus one helix 2 |
| α/β | core: three short helices packed against a barrel-like beta-sheet; some similarity to the SH3-like fold |
| α/β | beta*-alpha-beta(2)-alpha-beta-alpha; mixed beta sheet forms a partly open barrel: (n* = 4, S* = 8) |
| α/β | beta-alpha-beta(4)-alpha-beta(2); contains beta-sheet barrel (n = 5, S = 8) |
| α/β | beta(3)-alpha(2)-beta; 2 layers; mixed beta-sheet, order 4123, strands 1 and 4 are parallel to each other |
| α/β | mixed beta-sheet folds into a barrel (n = 8, S = 14) around the central helix |
| α/β | beta-sheet folds into a barrel (n = 11, S = 14) around the central helix |
| α/β | beta-sheet folds into a barrel (n = 12, S = 12) around the central helix |
| α/β | contains very long N-terminal helix, which end is packed against beta-sheet |
| α/β | core: beta(7)-alpha(2); N- and C-terminal extensions form a coiled coil subdomain |
| α/β | beta(6)-alpha; antiparallel beta-sheet, meander |
| α/β | beta(3)-alpha-beta(3)-alpha; 3 layers a/b/a |
| α/β | alpha(2)-beta(5)-alpha(2); 3 layers a/b/a; meander beta-sheet |
| α/β | core: beta(2)-alpha-beta(2); antiparallel beta-sheet |
| α/β | beta(4)-alpha-beta; 2 layers: alpha/beta; mixed beta-sheet, order: 51234 |
| α/β | alpha-beta-X-beta(2); 2 layers: alpha/beta; mixed beta-sheet, order: 123 |
| α/β | beta-alpha-beta-(alpha)-beta(2); 2 layers: alpha/beta; mixed beta-sheet, order: 1342 |
| α/β | beta(2)-alpha-beta; 2 layers: alpha/beta |
| α/β | beta-alpha-beta(3); 2 layers: alpha/beta |
| α/β | beta-alpha-beta(3); 2 layers: alpha/beta |
| α/β | beta(2)-alpha-beta(3); 2 layers: alpha/beta |
| α/β | multiple repeats of beta(2)-alpha(2) motif |
| α/β | beta(2)-alpha(3)-beta; two layers: alpha/beta; antiparallel sheet: order 213 |
| α/β | beta(4)-alpha(2); two layers: alpha/beta; antiparallel sheet: order 1432 |
| α/β | beta(2)-alpha(2)-beta(2)-alpha-beta; two layers: alpha/beta; antiparallel sheet: order 51234 |

TABLE 1-continued

Exemplary structures adopted by homologous superfamilies of proteins

| Structure | Architecture and/or topology of folds within proteins |
|---|---|
| α/β | beta-alpha(2)-beta(4)-alpha-beta(2); two layers: alpha/beta; bifurcated coiled beta-sheet: order of the first 5 strands: 23154 |
| α/β | beta(4)-alpha(2)-beta(2)-alpha; antiparallel sheet: order 123465 |
| α/β | beta-alpha-beta(6)-alpha(2); antiparallel sheet: order 165432 |
| α/β | beta(3)-alpha(2)-beta-alpha(2)-beta3; 2 layers alpha/beta; antiparallel sheet: order 1234567 |
| α/β | alpha-beta(6)-alpha(2)-beta-alpha(n); 3 layers alpha/beta/alpha; antiparallel sheet: order 1234567 |
| α/β | beta(4)-alpha-beta(2)-alpha(2); mixed, predominately antiparallel beta-sheet, order: 123465, strands 4 and 5 are parallel to each other |
| α/β | core: beta-alpha-beta(4); 2 layers: alpha/beta |
| α/β | core: beta-alpha-beta(4); 2 layers: alpha/beta |
| α/β | core: beta-alpha(2)-beta-X-beta(2); 2 layers: alpha/beta; antiparallel beta-sheet: order 1342 |
| α/β | alpha + beta sandwich; loop across free side of beta-sheet |
| α/β | alpha-beta-loop-beta(3); loop across free side of beta-sheet |
| α/β | core: beta-BETA-alpha-beta-BETA-beta-alpha; contains a beta-hammerhead motif similar to that in barrel-sandwich hybrids |
| α/β | core: beta(2)-alpha(2)-beta(2)-alpha(2); 2 layers a/b; mixed sheet: 2143 |
| α/β | beta(2)-alpha(n)-beta: 2 layers a/b; antiparallel sheet: 123 |
| α/β | alpha-beta(2)-alpha-beta-alpha(2); 3 strands of antiparallel sheet: 213 |
| α/β | beta-alpha(2)-beta-alpha-beta; 2 layers, alpha/beta |
| α/β | beta-alpha-beta(2)-alpha(2); 3 layers, alpha/beta/alpha; antiparallel beta-sheet: order 123 |
| α/β | beta-alpha(2)-beta(2); 2 layers, alpha/beta; antiparallel beta-sheet: order 123 |
| α/β | alpha-beta(3)-alpha(2); 2 layers, alpha/beta |
| α/β | (beta)-alpha-beta(3)-alpha; 2 layers, alpha/beta |
| α/β | alpha-beta(3)-alpha; 2 layers: alpha/beta |
| α/β | duplication: consists of two beta(3)-alpha repeats; 3 layers, beta/alpha/beta |
| α/β | beta-alpha-beta(2)-alpha; 2 layers: alpha/beta |
| α/β | alpha(2)-beta(3)-alpha(3); 2 layers alpha/beta, 3-stranded antiparallel beta-sheet; order 123 |
| α/β | alpha(3)-beta-alpha(2)-beta(2); 2 layers alpha/beta, 3-stranded antiparallel beta-sheet; order 123 |
| α/β | beta-alpha(2)-beta(2)-alpha; 2 layers: alpha/beta |
| α/β | core: alpha-beta(2)-(alpha)-beta; 2 layers: alpha/beta |
| α/β | core: alpha-beta-turn-beta-X-beta-(alpha); mixed beta-sheet, order of core strands: 123 |
| α/β | alpha(2)-beta(4); 2 layers: alpha/beta; antiparallel beta-sheet: order 2143 |
| α/β | alpha-beta(3)-alpha-beta-alpha; bifurcated coiled beta-sheet |
| α/β | beta(3)-alpha(3); meander and up-and-down bundle |
| α/β | beta-alpha(3)-beta(2); 2 layers: alpha/beta; related to the enolase/MLE N-domain fold by a circular permutation |
| α/β | alpha-beta-alpha(3)-beta(2); 2 layers: alpha/beta; |
| α/β | 3-helical bundle packed against 3-stranded mixed beta-sheet |
| α/β | beta(3)-alpha(4); meander beta-sheet packed against array of helices; contains Pro-rich stretch |
| α/β | beta(3)-alpha(5); meander beta-sheet packed against array of helices |
| α/β | beta-alpha-beta(2)-alpha; 2 layers: alpha/beta; mixed sheet 213; crossing loops |
| α/β | alpha-beta(3)-alpha(3); 2 layers, a/b; mixed beta-sheet, order: 132; crossing loops |
| α/β | alpha + beta sandwich with antiparallel beta-sheet; (beta-alpha-beta) × 2 |
| α/β | consists of two alpha + beta subdomains with some similarity to the ferredoxin-like fold |
| α/β | beta-alpha-beta-X-beta(2)-alpha(2)-beta; antiparallel beta-sheet, order 24153; topological similarity to the ferredoxin-like fold (scop_cf 54861) |
| multi | contains a cluster of helices and a beta-sandwich |
| multi | contains a cluster of helices and a beta-sandwich |
| multi | contains a cluster of helices and an alpha + beta sandwich |
| multi | consists of an all-alpha and alpha + beta domains |
| multi | contains a helical bundle with a buried helix and an alpha + beta insert domain |
| multi | consists of an all-alpha and alpha + beta domains connected by antiparallel coiled coil |
| multi | contains a cluster of helices and an alpha/beta domain |
| multi | contains an (8,10) beta-barrel and an all-alpha domain |
| multi | 2 domains: (1) all-alpha: 5 helices; (2) contains an open beta-sheet barrel: n* = 5, S* = 8; complex topology |
| multi | N-terminal domain is an alpha + beta, C-terminal domain is an alpha/beta with mixed beta-sheet |
| multi | divided into morphological domains including "palm", "thumb" and "fingers"; the catalytic "palm" domain is conserved to all members |
| multi | Multidomain subunits of complex domain organization |
| multi | 3 domains: (1&2) alpha + beta, with domain 2 being inserted in domain 1; (3) all-alpha |
| multi | 4 domains: (1) Toprim alpha/beta; (2&4) "winged helix"-like; (3) barrel: n = 6, S = 8 |

TABLE 1-continued

Exemplary structures adopted by homologous superfamilies of proteins

| Structure | Architecture and/or topology of folds within proteins |
|---|---|
| multi | 4 domains: (1) toprim alpha/beta; (2) "winged helix"-like; (3) alpha + beta; (4) all-alpha |
| multi | 2 domains: (1) toprim alpha/beta; (2) "winged helix"-like |
| multi | 2 domains: (1) alpha + beta; (2) toprim alpha/beta |
| multi | consists of three domains: alpha-helical dimerisation domain (res. 1-53) with HhH motif (Pfam 00633); 'treble cleft' C4 zinc-finger domain (54-76; Pfam 02132); and Toprim domain (76-199; segment-swapped dimer; Pfam 01751) |
| multi | 2 domains: alpha + beta and all-beta |
| multi | 2 domains: (1) alpha + beta: beta3-alpha2-beta2; (2) alpha/beta, a part of its mixed sheet forms barrel: n = 6, S = 8 |
| multi | 3 domains: (1) all-alpha; (2&3) alpha + beta |
| multi | 2 domains: (1) alpa/beta; (2) Fe—S cluster-bound |
| multi | 2 domains: (1) alpha/beta of a Rossmann-fold topology, binds NAD (2) multihelical array |
| multi | 4 domains: (1&2) duplication: share the same alpha/beta fold; (3) beta-barrel; (4) alpha + beta |
| multi | 2 domains: (1) alpha + beta; (2) alpha/beta (interrupts domain 1) |
| multi | 4 domains: (1) 3-helical bundle; (2) alpha + beta of ferredoxin-like fold (3 and 4) alpha + beta of dsRDB-like fold |
| multi | 3 domains: (1) 3-helical bundle; (2 and 3) alpha + beta of different folds: domain 3 has a ferredoxin-like fold and is inserted in domain 2 |
| multi | 3 domains: (1) 4-helical bundle; (2) alpha + beta; (3) "winged helix"-like |
| multi | 3 domains: (1 and 2) alpha + beta; (3) mostly alpha, inserted in domain 2 |
| multi | 3 domains: (1) spectrin repeat-like 3-helical bundle; (2 and 3) alpha/beta: Rossmann-fold topology |
| multi | 3 domains: (1) protozoan pheromone-like alpha-helical bundle; (2) rubredoxin-like domain lacking metal-binding site; (3) alpha + beta heterodimerisation domain: alpha-beta(5)-alpha |
| multi | 2 domains: (1) alpha-helical bundle; (2) beta-barrel (n = 5, S = 8) |
| multi | 3 domains: (1) alpha-helical bundle; (2&3) complex all-beta folds |
| multi | 2 closely associated domains: (1) all-alpha, EF-hand like; (2) alpha + beta, Frataxin-like |
| multi | 2 domains; d1: [all-alpha; 3-helical bundle, similar to the immunoglobulin/albumin-binding domain-like fold (scop_cf 46996)]; d2: [alpha/beta; 3 layers, a/b/a; 6-stranded mixed beta-sheet, order: 321456, strand 6 is antiparallel to the rest] |
| multi | 3 domains; d1: alpha + beta [alpha(2)-beta(3); mixed sheet: 213]; d2: alpha/beta of the NAD(P)-binding Rossmann-fold superfamily (scop_sf 51735, most similar to scop_fa 51883 and scop_fa 51736); d3: alpha + beta of the glutamine synthetase/guanido kinase fold (scop_cf 55930); d1 and d3 form a single beta-sheet |
| multi | 2 domains: d1 [alpha/beta; related to the PFK N-terminal domain (scop_sf 53784)]; d2 [all-beta; atypical beta-sandwich made of 4 structural repeats of beta(3) unit] |
| multi | 2 domains; d1 (1-64, 174-335) [alpha/beta; 3 layers, a/b/a; mixed beta sheet of 9 strands, order: 219863457; strands 1, 5 and 8 are antiparallel to the rest]; d2 (65-142) [all-beta; barrel, closed (n = 6, S = 10); greek-key; topologically similar to the split barrel fold (scop_cf 50474) |
| multi | 2 domains; (1) alpha + beta (res 1-192), a circularly permuted rS5 domain 2-like fold (scop_cf 54210); (2) alpha/beta with parallel beta-sheet of 4 strands, order 2134 |
| multi | consists of two domains; d1: alpha + beta (78-190; alpha-beta(4)-alpha-beta-alpha; 3 layers; antiparallel beta-sheet of 5 strands; order 51234); d2: alpha/beta similar to the G-domain fold (191-381; scop_fa 52592) |
| multi | 2 domains: (1) all-alpha, (2) alpha + beta; asymmetric homodimer with each domain intertwining with its counterpart |
| multi | 4 domains: three intertwined predominately alpha domains and one jelly-roll beta-sandwich |
| multi | large protein without apparent domain division; has a number of all-alpha regions and one all beta domain near the C-end |
| multi | large protein without apparent domain division |
| multi | large protein without apparent domain division |
| membrane + surface | multi-helical domains of various folds which unfold in the membrane |
| membrane + surface | core: up-and-down bundle of seven transmembrane helices tilted 20 degrees with respect to the plane of the membrane |
| membrane + surface | five transmembrane helices forming a sheet-like structure |
| membrane + surface | 12 transmembrane helices in an approximate threefold rotational symmetric arrangement |
| membrane + surface | core: 7 transmembrane helices organized into two bundles, one formed by the first two helices and the other by the rest |
| membrane + surface | two antiparallel transmembrane helices |
| membrane + surface | core: up-and-down bundle of four transmembrane helices |

TABLE 1-continued

Exemplary structures adopted by homologous superfamilies of proteins

| Structure | Architecture and/or topology of folds within proteins |
|---|---|
| membrane + surface | core: 8 helices, 2 short helices are surrounded by 6 long transmembrane helices |
| membrane + surface | 11 transmembrane helices; duplication: consist of 2 structural repeats of five helices each plus extra C-terminal helix |
| membrane + surface | 12 transmembrane helices; duplication: the N- and C-terminal halves are structurally similar |
| membrane + surface | core: 18 transmembrane helices |
| membrane + surface | oligomeric transmembrane alpha-helical proteins |
| membrane + surface | oligomeric transmembrane alpha-helical protein |
| membrane + surface | oligomeric transmembrane alpha-helical protein |
| membrane + surface | heteropentameric transmembrane alpha-helical protein; 4 transmembrane helices per subunit |
| membrane + surface | oligomeric fold; 3 transmembrane helices per subunit |
| membrane + surface | oligomeric fold; 3 transmembrane helices per subunit |
| membrane + surface | 9 transmembrane helices |
| membrane + surface | 10 transmembrane helices forming of a gated channel |
| membrane + surface | core: 11 transmembrane helices |
| membrane + surface | core: hairpin of two transmembrane helices |
| membrane + surface | core: three transmembrane helices, bundle |
| membrane + surface | multihelical; complex architecture with several transmembrane helices |
| membrane + surface | multihelical; complex architecture with several transmembrane helices |
| membrane + surface | 12 transmembrane helices; duplication: the N- and C-terminal halves of the whole proteins are structurally similar |
| membrane + surface | core: three transmembrane helices, up-and-down bundle |
| membrane + surface | core: four transmembrane helices, up-and-down bundle, binds one or two heme groups in between the helices |
| membrane + surface | membrane-associated alpha-helical protein; no transmembrane helices |
| membrane + surface | membrane-associated alpha-helical protein; no transmembrane helices |
| membrane + surface | 2 helices, hairpin |
| membrane + surface | core: multihelical; consists of three transmembrane regions of 2, 2 and 6 helices, separated by cytoplasmic domains |
| membrane + surface | membrane all-alpha fold |
| membrane + surface | membrane all-alpha fold; 6-helical "barrel" with internal binding cavity |
| membrane + surface | membrane all-alpha fold; three transmembrane helices |
| membrane + surface | , gathers together transmembrane barrels of different (n, S) |
| membrane + surface | subunit fold contains tandem repeat of alpha-beta hairpin-alpha(2) motif |
| membrane + surface | consists of three domains: beta-barrel (res. 29-38, 170-259; scop_cf 50412); barrel-sandwich hybrid (39-72, 135-169; scop_sf 51230) and long alpha-hairpin (73-134; scop_cf 46556) |
| membrane + surface | subunit fold contains beta-sandwich of Ig-like (grerk-key) topology and a beta-ribbon arm that forms an oligomeric transmembrane barrel |
| membrane + surface | contains several large open beta-sheets |
| membrane + surface | 3 domains: (1) alpha + beta; (2&3) all-beta |
| membrane + surface | 2 domains: (1) alpha + beta; (2) all-beta, similar to the CalB domain fold but the two last strands are transposed |
| membrane + surface | 2 intertwined domains; all-beta and alpha + beta |
| membrane + surface | 2 domains; d1: complexed all-beta fold; d2: coiled-coil (trimeric) helical region |
| membrane + surface | 3 intertwined all-beta domains |
| membrane + | trimer; one subunit consists of an alpha/beta oligomerization subdomain [3- |

TABLE 1-continued

Exemplary structures adopted by homologous superfamilies of proteins

| Structure | Architecture and/or topology of folds within proteins |
|---|---|
| surface membrane + surface | stranded parallel beta-sheet, order 213], and an antiparallel coiled coil 4 domains; I (res. 14-225) and II (226-487) are beta-sandwiches of similar gamma-crystallin like topologies; III (488-594) has a beta-grasp like fold; IV (595-735) has an Ig-like fold |
| Other | nearly all-alpha |
| Other | disulfide crosslinked alpha-helical hairpin |
| Other | disulfide-bound fold; contains beta-hairpin with two adjacent disulfides |
| Other | disulfide-rich fold; all-beta: 3 antiparallel strands |
| Other | disulfide-rich fold; all-beta: 3 antiparallel strands |
| Other | disulfide-rich; alpha + beta: 3 antiparallel strands followed by a short alpha helix |
| Other | disulfide-rich fold: nearly all-beta |
| Other | disulfide-rich alpha + beta fold |
| Other | Disulfide-rich fold, nearly all-beta |
| Other | alpha + beta fold with two crossing loops |
| Other | disulfide-rich fold |
| Other | disulfide-rich calcium-binding fold |
| Other | disulfide-rich alpha + beta fold |
| Other | disulfide-rich fold; nearly all-beta |
| Other | disulfide-rich small alpha + beta fold; topological similarity to the Ovomucoid domain III |
| Other | disulfide-rich fold; common core is alpha + beta with two conserved disulfides |
| Other | disulfide-rich fold; all-beta; duplication: contains two structural repeats |
| Other | disulfide-rich fold; common core is all-beta |
| Other | disulfide-rich all-beta fold |
| Other | disulfide-rich all-alpha fold |
| Other | small disulfide-rich |
| Other | disulfide-rich; nearly all-beta |
| Other | disulfide-rich; nearly all-beta |
| Other | disulfide-rich; alpha + beta |
| Other | duplication: consists of three similar disulfide-rich domains |
| Other | duplication: consists of two similar disulfide-rich domains, alpha + beta |
| Other | disulfide-rich; all-beta: open barrel, 5 strands; OB-fold-like |
| Other | disulfide-rich, all-beta |
| Other | disulfide-rich, alpha + beta |
| Other | disulfide-rich, alpha + beta |
| Other | disulfide-rich, alpha + beta |
| Other | disulfide-rich, alpha + beta |
| Other | disulfide-rich |
| Other | disulfide-rich, all-alpha |
| Other | disulfide-rich; all-alpha |
| Other | disulfide-rich, alpha + beta |
| Other | disulfide-rich |
| Other | disulfide-rich; all-alpha; calcium-binding |
| Other | disulfide-rich |
| Other | disulfide-rich all-beta fold; contains beta sandwich of 5 strands |
| Other | disulfide-rich six-stranded beta-sandwich; jelly-roll |
| Other | bipartite cysteine-rich all-alpha domain; a single helix in the N-terminal part (chain A) is linked by disulfides to the C-terminal part (chain B) [3-helical bundle of the RuvA C-terminal domain-like fold (scop_cf 46928) |
| Other | Calcium ion-bound |
| Other | a few helical turns and a disulfide-crosslinked loop |
| Other | a few helical turns assembled without a hydrophobic core? |
| Other | folds around 4Fe—4S cluster |
| Other | folds around 4Fe—4S cluster |
| Other | alpha + beta metal(zinc)-bound fold: beta-hairpin + alpha-helix |
| Other | all-alpha dimetal(zinc)-bound fold |
| Other | alpha + beta metal(zinc)-bound fold |
| Other | consist of two different zn-binding subdomains, each subdomain resembles a distorted glucocorticoid receptor-like fold |
| Other | metal(zinc)-bound fold |
| Other | metal(zinc or iron)-bound fold; sequence contains two CX(n)C motifs, in most cases n = 2 |
| Other | zinc-bound beta-ribbon motif |
| Other | zinc-bound beta-ribbon motif |
| Other | zinc-bound alpha + beta motif |
| Other | dimetal(zinc)-bound alpha + beta motif; structurally diverse |
| Other | zinc-bound alpha + beta motif |
| Other | metal(iron)-bound fold |
| Other | metal(zinc)-bound alpha + beta fold |
| Other | metal(zinc)-bound alpha + beta fold |
| Other | dimetal(zinc)-bound alpha + beta fold |
| Other | dimetal(zinc)-bound alpha + beta fold |
| Other | metal(zinc)-bound alpha + beta fold |
| Other | metal(zinc)-bound alpha + beta fold |
| Other | metal(zinc)-bound alpha + beta fold |

TABLE 1-continued

Exemplary structures adopted by homologous superfamilies of proteins

| Structure | Architecture and/or topology of folds within proteins |
|---|---|
| Other | Zn-binding, all-alpha fold |
| Other | all-alpha fold; Zn-binding sites are in the loops connecting helices |
| Other | alpha-helical fold with two Zn-binding sites |
| Other | metal(zinc)-bound extended beta-hairpin fold |
| Other | metal(zinc)-bound fold |
| Other | metal(zinc)-bound fold |
| Other | metal(calcium)-bound fold |

Terms used in Table 1 will be apparent to the skilled artisan. However, the following definitions are provided for clarity below.

"Meander" is a simple topology of a beta-sheet where any two consecutive strands are adjacent and antiparallel.

"Up-and-down" is the simplest topology for a helical bundle or folded leaf, in which consecutive helices are adjacent and antiparallel; it is approximately equivalent to the meander topology of a beta-sheet.

"Crossover connection" links secondary structures at the opposite ends of the structural core and goes across the surface of the domain.

"Greek-key" is a topology for a small number of beta sheet strands in which some interstrand connections going across the end of barrel or, in a sandwich fold, between beta sheets.

"Jelly-roll" is a variant of Greek key topology with both ends of a sandwich or a barrel fold being crossed by two interstrand connections.

"All-alpha" class has the number of secondary structures in the domain or common core described as 3-, 4-, 5-, 6- or multi-helical.

"Bundle" is an array of alpha-helices each oriented roughly along the same (bundle) axis. It may have twist, left-handed if each helix makes a positive angle to the bundle axis, or be right-handed if each helix makes a negative angle to the bundle axis.

"Folded leaf" is a layer of alpha-helices wrapped around a single hydrophobic core but not with the simple geometry of a bundle.

"Array" (of hairpins) is an assembly of alpha-helices that can not be described as a bundle or a folded leaf.

"Closed", "partly opened" and "opened" for all-alpha structures describes the extent in which the hydrophobic core is screened by the comprising alpha-helices. "Opened" means that there is space for at least one more helix to be easily attached to the core.

Beta-sheets can be "antiparallel" (i.e. the strand direction in any two adjacent strands are antiparallel), "parallel" (all strands are parallel each other) or "mixed" (there is one strand at least that is parallel to one of its two neighbours and antiparallel to the other).

"All-beta" class includes two major fold groups: sandwiches and barrels. The "sandwich" folds are made of two beta-sheets which are usually twisted and pack so their strands are aligned. The "barrel" fold are made of single beta-sheet that twists and coils upon itself so, in most cases, the first strand in the beta sheet hydrogen bond to the last strand. The strand directions in the two opposite sides of a barrel fold are roughly orthogonal. Orthogonal packing of sheets is also seen in a few special cases of sandwich folds "Barrel structures" are usually closed by main-chain hydrogen bonds between the first and last strands of the beta sheet, in this case it is defined by the two integer numbers: the number of strand in the beta sheet, n, and a measure of the extent the extent to which the strands in the sheet are staggered the shear number, S.

"Partly open barrel" has the edge strands not properly hydrogen bonded because one of the strands is in two parts connected with a linker of more than one residue. These edge strands can be treated as a single but interrupted strand, allowing classification with the effective strand and shear numbers, n* and S*. In the few open barrels the beta sheets are connected by only a few side-chain hydrogen bonds between the edge strands.

It is likely that there exists a bias in nature towards particular folds, simply because of the evolutionary constraints applied to protein structure and function determination. For example, approximately 30% of folds and 50% of protein superfamilies are contained within about 4-5 architectures, in particular αβ-sandwiches (two- and three-layer), αβ-barrel, β-barrel, α-updown structures (see Orengo et al., Ann. Rev. Biochem. 74, 867-900, 2005). Many folds are also reported as sharing common structural motifs due to the recurrence of simple structural motifs e.g., αβ-motifs, ββ-motifs, split βαβ-motifs. Nearly 80 different folds are classified as adopting a three-layer αβ-sandwich architecture, and the most highly-populated fold groups adopt regular architectures (e.g., TIM barrel fold, αβ-barrel, Rossman fold; three-layer, αβ-sandwich; αβ-plait, two-layer αβ-sandwich) that may be more stable when mutated (Orengo et al., ibid.). Recent statistical analyses suggest that more highly-represented folds i.e., "superfolds" support a much broader repertoire of primary sequences than other folds (Shakhnovich et al., J. Mol. Biol. 326, 1-9, 2003). For example, the CATH database provides a hierarchical classification of domains, within protein structures, in the Protein Data Bank (PDB; Berman et al., Nucl. Acids Res. 28, 235-242, 2000). There are about 32 architectures described in the CATH database.

5. Peptide Sources

Methods for producing libraries encoding peptides that correspond to naturally-occurring protein domains and/or sub-domains and/or are capable of forming secondary and/or super-secondary structures are known e.g., as described in International Patent Publication Nos. WO/2004/074479 (International Application No. PCT/AU2004/000214) and WO/2007/097923 (International Application No. PCT/AU2007/097923). The contents of these applications are incorporated herein in their entirety.

For example, nucleic acid fragments comprising genomic DNA, cDNA, or amplified nucleic acid derived from one or two or more well-characterized genomes e.g., a prokaryote genome or a eukaryote having a small genome such as a protist, dinoflagellate, alga, plant, fungus, mould, invertebrate or vertebrate may be employed to produce an expression library. Such nucleic acid fragments are derived, for example, from one or two or more of *Aeropyrum pernix, Aquifex aeolicus, Archaeoglobus fulgidis, Bacillus subtilis, Bordetella per-* tussis, Borrelia burgdorferi, Chlamydia trachomatis, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis PCC 6803, Thermoplasma volcanium and Thermotoga maritima. The nucleic acid fragments are generated using art-recognized methods e.g., mechanical shearing, digestion with a nuclease, digestion with a restriction endonuclease, amplification by polymerase chain reaction (PCR) using random oligonucleotide primers, and combinations thereof.

The nucleic acid fragments are inserted into a suitable expression vector or gene construct in operable connection with a suitable promoter for expression of an encoded peptide in each clone. One approach employs site-specific recombinases to integrate fragments comprising one or two flanking recombination sites into a plasmid vector having compatible recombination sites. Site-specific recombination systems typically comprise one or more proteins that recognize a specific recombination site sequence in a plasmid vector and in the DNA insert, cleave the nucleic acids and ligate them together via cross-over event(s). Several site-specific recombinases are known in the art e.g., the bacteriophage P1 Cre/lox system (Austin et al. Cell 25, 729-736, 1981), the R/RS recombinase system from the pSR1 plasmid of the yeast Zygosaccharomyces rouxii (Araki et al., J. Mol. Biol. 182, 191-203, 1985), the Gin/gix system of phage Mu (Maeser et al., Mol. Gen. Genet. 230, 170-176, 1991), the FLP/FRT recombinase system from the 2 micron plasmid of the yeast Saccharomyces cerevisiae (Broach et al., Cell 29, 227-234, 1982), and the Integrase from bacteriophage Lambda (Landy et al., Ann. Rev. Biochem. 58, 912-949, 1989; Landy et al., Curr. Opin. Genet. Dev. 3, 699-707, 1993; Lorbach et al., J. Mol. Biol. 296, 1175-1181, 2000; and WO 01/16345). The integrase system utilizes attachment sites (attB, attP, attL, attR) to facilitate integration of insert nucleic acid into vector, wherein attB sites recombine with attP sites in a reaction mediated by an integrase enzyme to yield attL and attR sites on resulting "entry" plasmid vectors. The DNA inserts are then mobilized into a suitable "destination" expression plasmid by recombination between attL sites and attR sites in a reaction mediated by an integrase enzyme to yield attB and attP sites.

Serine recombinase systems e.g., Sin resolvase system, are also known in the art to provide for recombination between donor and acceptor sites in DNA for cloning purposes. For example, the *Mycobacterium tuberculosis* prophage-like element ΦRv1 encodes a site-specific recombination system utilizing an integrase of the serine recombinase family, wherein recombination occurs between a putative attP site and the host chromosome, but is unusual in that the attB site lies within a redundant repetitive element (REP13E12) of which there are seven copies in the *M. tuberculosis* genome; and wherein four of these repetitive elements contain attB sites suitable for ΦRv1 integration in vivo. Although the mechanism of directional control of large serine integrases is poorly understood, a recombination directionality factor (RDF) has been identified that is required for ΦRv1 integrase-mediated excisive recombination in vivo. Defined in vitro recombination reactions for both ΦRv1 integrase-mediated integration and excision require the ΦRv1 RDF for excision, but not DNA supercoiling, host factors, or high-energy cofactors (unlike the lambda integrase system). Integration, excision and excise-mediated inhibition of integration require simple substrates sites, indicating that the control of directionality does not involve the manipulation of higher-order protein-DNA architectures as described for the tyrosine integrases.

Generally, the construct used for expression is determined by the system(s) that will be used to display the encoded peptides for screening purposes e.g., by direct display on a physical medium or by phage display or recombinant expression. Such display generally provides for the peptides to assume a secondary or super-secondary structure.

Alternatively, peptide libraries are produced based on source data comprising annotations of primary sequences determined and/or predicted structures for proteins from which the component peptides are derived. For example, source data consisting of protein sequence resources such as PRINTS, Pfam, SMART, Propom, InterPro, TIGRFAMs, ADDA, CHOP, ProtoNet, SYSTERS, iProClass, SWIS-SPROT, COG/KOG, and protein structure family resources such as CAMPASS (Cambridge University, UK), CATH database (University College, London, UK), CE (SDSC, La Jolla, Calif., USA), DHS (University College, London, UK), ENTREZ/MMDB (NCBI, Bethesda Md., USA), Structural Classification of Protein Database (SCOP) (Andreeva et al., Nucl. Acid Res. 32:D226-D229, 2004), or the Protein Data Bank (PDB) (Berman et al., Nucleic Acid Res. 28: 235, 2000) are used to determine amino acid sequences capable of independently-forming secondary structures and/or assemblies of secondary structures and/or folds suitable for practical application in drug screening. In such an approach, synthetic peptides are produced having the sequences that are capable of forming those secondary structures and super-secondary structures, or alternatively, nucleic acid encoding the amino acid sequences are synthesized and cloned into suitable expression vectors as described herein above. As with libraries produced from genomic fragments, peptide libraries produced using bioinformatics data must be displayed for the purposes of screening to ascertain their bioactivity. Again, display generally provides for the peptides to assume a secondary or super-secondary structure.

In the foregoing methods, each clone of the library encodes, on average, a monomeric peptide.

Suitable display methods for peptide libraries include e.g., arraying the peptides on a solid surface, e.g., a microarray, or on a plurality of solid surfaces, e.g., a plurality of beads, or in microwells. The peptides may be synthesized directly onto a solid surface or immobilized on a solid surface. For example, a parallel array or pool of peptides can be produced by synthetic means and arrayed in a multi-well plate for high-throughput screening. Peptides can also be displayed using recombinant means e.g., by virtue of being expressed on the surface of a phage or a cell or by ribosome display or by in vitro display or within cells. In such methods, peptides are generally displayed (and subsequently screened) as monomers.

Modulators of CD40/CD40L Signaling

Monoclonal antibodies that block the interaction of CD40L with its cognate CD40 receptor to prevent allograft rejection in primates have been described e.g., Kirk et al., Nature Med. 5, 686-693 (1999). Such immunotherapy has also been reported for therapy of animal models of diabetes e.g., Kover et al., Diabetes 49, 1666-1670 (2000) and atherosclerosis e.g., Mach et al., Nature 394, 200-203 (1998). CD40L immunotherapy carries a high incidence of adverse consequences such as thromboembolic complications e.g., Boumpas et al., Arthrtitis Rheum. 48, 719-727 (2003), possibly due to the induction of Fc-mediated platelet aggregation e.g., Langer et al., Thromb Haemost 93, 1137-1146 (2005); Mirabet et al., Mol. Immunol. 45, 937-944 (2008).

A peptide derived from the native CD40-CD40L interface i.e., residues 181-205 of CD40L and a retro-inverso peptide analog thereof are described by Allen et al., J. Peptide Res. 65, 591-604 (2005). The term "native interface" or "native CD40-CD40L interface" or similar means that the peptide comprises a linear sequence of one of the binding partners i.e., CD40 or CD40L that is involved in their interaction, or a reverse sequence thereof e.g., a sequence of a retro-inverted analog. For example, the peptide described by Allen et al. (2005) comprises R203 of CD40L known to be involved in binding to CD40 and flanking sequence. The peptide and its chiral analog were reported to block T-cell proliferation in vitro, and to reduce incidence and severity of experimental encephalomyelitis (EAE) when administered to mice. There are a limited number of primary or secondary or tertiary structure permutations derivable the native interaction interface of CD40 and CD40L, thereby limiting the range of available therapeutics for ameliorating the adverse consequences of CD40-signaling through CD40L.

More recently, phage-expressed 7-mer peptide aptamers that had been disulfide-constrained by cyclization through their N-terminal and C-terminal cysteine residues, have also been described to bind to CD40L in vitro, and a single peptide thereof shown to inhibit CD40-mediated B-cell activation, Ig switching, endothelial cell migration and angiogenesis e.g., Deambrosis et al., J. Mol. Med. 87, 181-197 (2009). As with strategies for peptidomimetics based on the native CD40-CD40L interface, strategies employing disulfide-constrained aptamers of fixed length form a limited number of secondary or tertiary structure permutations, thereby limiting the range of available therapeutics for ameliorating the adverse consequences of CD40-signaling through CD40L. This conclusion is supported by the low primary hit rate in aptamer screens for binding activity and/or high attrition rate of aptamers tested for inhibitory activity.

There is an ongoing need for compounds that ameliorate the adverse effects of CD40L signaling events, including those events mediated by CD40 and/or Mac-1. Inverse agonists and antagonists of CD40L would be particularly useful for providing such benefits.

General

Conventional techniques of molecular biology, microbiology, virology, recombinant DNA technology, peptide synthesis in solution, solid phase peptide synthesis, and immunology are described, for example, in the following texts that are incorporated by reference:

Sambrook, Fritsch & Maniatis, Molecular Cloning: A Laboratory Manual, Cold Spring Harbor Laboratories, New York, Second Edition (1989), whole of Vols I, II, and III;

DNA Cloning: A Practical Approach, Vols. I and II (D. N. Glover, ed., 1985), IRL Press, Oxford, whole of text;

Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;

Animal Cell Culture: Practical Approach, Third Edition (John R. W. Masters, ed., 2000), ISBN 0199637970, whole of text;

Perbal, B., A Practical Guide to Molecular Cloning (1984);

Methods In Enzymology (S. Colowick and N. Kaplan, eds., Academic Press, Inc.), whole of series;

J. F. Ramalho Ortigão, "The Chemistry of Peptide Synthesis" In: Knowledge database of Access to Virtual Laboratory website (Interactiva, Germany);

Barmy, G. and Merrifield, R. B. (1979) in The Peptides (Gross, E. and Meienhofer, J. eds.), vol. 2, pp. 1-284, Academic Press, New York.

Bodanszky, M. (1984) Principles of Peptide Synthesis, Springer-Verlag, Heidelberg.

Bodanszky, M. & Bodanszky, A. (1984) The Practice of Peptide Synthesis, Springer-Verlag, Heidelberg.

Bodanszky, M. (1985) Int. J. Peptide Protein Res. 25, 449-474.

Golemis (2002) Protein-Protein Interactions: A Molecular Cloning Manual (Illustrated), Cold Spring Harbor Laboratory, New York, ISBN 0879696281.

Smith et al., (2002) Short Protocols in Molecular Biology: A Compendium of Methods from Current Protocols in Molecular Biology, 5th Edition (Illustrated), John Wiley & Sons Inc., ISBN 0471250929.

Sambrook and Russell (2001) Molecular Cloning, Cold Spring Harbor Laboratory, New York, ISBN 0879695773.

SUMMARY OF INVENTION

1. Introduction

The present invention provides peptidyl and non-peptidyl compositions that bind to CD40L (CD154) and/or prevent, reduce or inhibit CD40L from interacting with CD40 and/or modulate CD40 signaling and/or modulate CD40L signalling. The invention also relates to the use of such compositions in medicine. In one example, a composition of the present invention is for use in a method of diagnosis and/or prognosis and/or prophylaxis and/or therapy of the human or animal body. In another example, a composition of the present invention is for use or in an ex vivo method of diagnosis and/or prognosis and/or prophylaxis and/or therapy of the human or animal body. In another example, a composition of the present invention is for use in an in vivo or ex vivo method, such as a method of diagnosis and/or prognosis and/or prophylaxis and/or therapy, to ameliorate one or more adverse effects or consequences of CD40L signaling and/or CD40 signaling.

The present invention is based in part upon the identification by the inventors of compositions e.g., peptides and derivatives and analogs thereof that bind to CD40L e.g., at $IC_{50}$ less than about 500 nM, and/or competitively antagonize or inhibit the interaction between CD40L and its cognate receptor CD40, and/or selectively inhibit or reduce CD40L-mediated expression of CD86 on primary B-cells and/or selectively antagonize or inhibit CD40L-mediated T-cell proliferation.

The peptides of the present invention are expressed from fragments of prokaryotic and compact eukaryotic genomes, not all of which are native open reading frames of those genomes. The peptides of the present invention are also not aptamers or peptide fragments derived from the native CD40-CD40L interface. For example, the peptides may have no known function or be derived from proteins having functions distinct from CD40 or CD40L. Accordingly, the peptides of the invention do not modulate CD40L-mediated events e.g., when expressed in their native contexts i.e., in the proteins in which they are expressed in nature. Alternatively, or in addition, the peptides of the present invention do not comprise N-terminal and C-terminal flanking cysteine residues, e.g., for conformational stability, as distinct from peptide aptamers. For example, the peptides of the present invention have lengths sufficient to form a secondary structure or super-secondary structure e.g., autonomously, such as without the need for flanking N-terminal and C-terminal cysteines to achieve their cyclization.

As used herein, the term "CD40L antagonist", "CD40L peptidyl inhibitor" or "CD40L peptide inhibitor" or "CD40L inhibitor" or similar term shall be taken to mean a composition of the invention that binds to CD40L and inhibits or reduces or delays one or more CD40L-dependent effects in vitro or in vivo, e.g., a peptidyl inhibitor that binds to CD40L and inhibits one or more CD40L-mediated effects such as CD40L-mediated signaling, including CD40-CD40L costimulatory effects such as downstream effect(s) of CD40L-dependent CD40-mediated signaling.

The present invention is also based on the inventors' understanding that, in general, the serum half-life of a peptide of less than about 50-100 amino acids in length may be short, and that such a peptide may have lower affinity than desirable for pharmaceutical applications. The inventors reasoned that the half-life and/or the affinity of binding between a small peptide and its target may be enhanced inter alia by producing peptide derivatives and analogs such as: (i) a derivative having enhance entropy (e.g., PEGylated and/or HESylated and/or polyglycinated and/or multimeric forms of one or more base peptides having a desired activity); and/or (ii) a derivative comprising a "serum protein moiety" e.g., albumin or ferritin or transferrin or immunoglobulin or immunoglobulin fragment e.g., domain antibody (dAb) or modified Fc component of immunoglobulin lacking effector function or Fc-disable immunoglobulin such as a CovXBody; and/or (iii) a derivative comprising a "serum protein-binding moiety" e.g., albumin-binding peptide, albumin-binding domain (ABD or Affybody) or serum albumin-binding antibody domain (AlbudAb) that binds to albumin or immunoglobulin (Ig) or Ig fragment such as Fc; and/or (iv) an analog comprising D-amino acids e.g., a retro-peptide analog or retro-inverso analog of one or more base peptides and/or derivatives according to any example hereof and having a desired activity. For example, a derivatives or analog of a CD40L peptide inhibitor may have enhanced CD40L inhibitory activity and/or serum half-life compared to a corresponding base peptide from which it has been derived.

Accordingly, one example of the present invention provides a PEGylated peptidyl inhibitor of CD40L-dependent signaling. In another example, the present invention provides a HESylated peptidyl inhibitor of CD40L-dependent signaling. In another example, the present invention provides a polyglycinated peptidyl inhibitor of CD40L-dependent signaling. In another example, the present invention provides a composition comprising a peptidyl inhibitor of CD40L-dependent signalling as described according to any example hereof and a serum protein moiety as described according to any example hereof. In another example, the present invention provides a composition comprising a peptidyl inhibitor of CD40L-dependent signalling as described according to any example hereof and a peptidyl serum protein-binding moiety as described according to any example hereof. In another example, the present invention provides a composition comprising a peptidyl inhibitor of CD40L-dependent signalling as described according to any example hereof and a non-peptidyl serum protein-binding moiety as described according to any example hereof e.g., a hapten that binds to an Fc-disabled antibody, polyethylene glycol, hydroxyethyl starch (HES), polyglycine, a 4,4-diphenylcyclohexyl moiety or 4-phenylbutanoic acid moiety.

Another example of the present invention provides a PEGylated chiral analog of a peptidyl inhibitor of CD40L-dependent signalling as described according to any example hereof. In another example, the present invention provides a HESylated chiral analog of a peptidyl inhibitor of CD40L-dependent signaling as described according to any example hereof. In another example, the present invention provides a polyglycinated chiral analog of a peptidyl inhibitor of CD40L-dependent signaling as described according to any example hereof. In another example, the present invention provides a composition comprising a chiral analog of a peptidyl inhibitor of CD40L-dependent signalling as described according to any example hereof and a serum protein moiety as described according to any example hereof wherein the serum protein moiety may itself be a chiral analog such as by comprising D-amino acids, or it may comprise L-amino acids. In another example, the present invention provides a composition comprising a chiral analog of a peptidyl inhibitor of CD40L-dependent signalling as described according to any example hereof and a peptidyl serum protein-binding moiety as described according to any example hereof, wherein the serum protein-binding moiety may itself be a chiral analog such as by comprising D-amino acids, or it may comprise L-amino acids. In another example, the present invention provides a composition comprising a chiral analog of a peptidyl inhibitor of CD40L-dependent signalling as described according to any example hereof and a non-peptidyl serum protein-binding moiety e.g., a hapten that binds to Fc, polyethylene glycol, hydroxyethyl starch (HES), polyglycine, a 4,4-diphenylcyclohexyl moiety or 4-phenylbutanoic acid moiety e.g., conjugated to D-lysine.

The present invention also provides compositions comprising cysteine-free peptidyl inhibitors of CD40L-dependent signalling, wherein the peptidyl inhibitor moiety lacks cysteine residues e.g., by virtue of substitution of cysteine for another amino acid such as serine. Such compositions may be PEGylated, HESylated, polyglycinated, multimerized, or comprise serum protein moiety or serum protein-binding moiety with or without intervening spacer as described according to any example hereof, and they may be chiral analogs according to any example hereof e.g., retroinverted analogs.

The present invention also provides a multimeric peptidyl inhibitor of CD40L-dependent signaling. As used in this context, the term "multimeric peptidyl inhibitor" shall be taken to mean that the composition comprises two or more peptidyl inhibitors that each inhibit CD40L-dependent signalling in their monomeric form. In one example, homodimers and heterodimers have enhanced inhibitory activity compared to a monomeric peptide from which it is derived e.g., with respect to CD40L binding to CD40 and/or inhibition of CD40L binding to a cognate binding partner such as CD40 or Mac-1 and/or inhibition of one or more CD40L-dependent effects such as B-cell proliferation or T-cell proliferation. For example, the effect of multimerization is more than the additive effect of either base peptide. A multimeric peptidyl inhibitor of CD40L-dependent signaling may be PEGylated, HESylated, polyglycinated, multimerized, or comprise a serum protein moiety or a serum protein-binding moiety with or without intervening spacer as described according to any example hereof, and may be a chiral analog according to any example hereof e.g., a retroinverted analog.

More particularly, another example of the present invention provides a PEGylated peptidyl inhibitor of CD40L-dependent signalling or a PEGylated multimeric peptidyl inhibitor of CD40L-dependent signaling, wherein the peptidyl inhibitor lacks cysteine residues e.g., by virtue of substitution of cysteine for another amino acid such as serine, or comprises a single N-terminal or C-terminal cysteine residue. In yet another example, the present invention provides a PEGylated chiral analog of a peptidyl inhibitor of CD40L-dependent signaling, wherein the peptidyl inhibitors lack cysteine residues e.g., by virtue of substitution of cysteine for another amino acid such as serine.

The present invention also extends to the production and/or use of recombinant combinatorial proteins comprising pluralities of the peptides, derivatives and analogs described according to any example of the invention herein, e.g., recombinantly-produced peptidomimetics comprising one or more protein sub-domains, domains, folds, secondary structures or super-secondary structures.

The present invention also extends to pharmaceutical compositions comprising the synthetic and recombinant peptide-based i.e., "peptidyl" CD40L-binding compositions described according to any examples hereof, and to the use of such compositions in medicine and/or pharmacy. For example, the peptides and any analogs or derivatives thereof may be formulated with a suitable carrier or excipient e.g., for injection or inhalation or oral administration.

The present invention also extends to non-peptidyl equivalents of the exemplified peptides, peptidyl analogs and peptidyl derivatives provided herein, and to compositions comprising same and methods for their production and/or use in medicine and/or pharmacy. For example, the non-peptidyl equivalents may be formulated with a suitable carrier or excipient e.g., for injection or inhalation or oral administration.

The present invention also extends to diagnostic, prognostic, prophylactic, therapeutic and research applications of the peptides and compositions of the invention described herein.

2. General

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein, which are intended for the purpose of exemplification only. Functionally-equivalent products, compositions and methods are clearly within the scope of the invention, as described herein.

3. Specific Examples

The scope of the invention will be apparent from the claims as filed with the application, which are hereby incorporated into the description. The scope of the invention will also be apparent from the following specific examples.

One example of the present invention provides a composition comprising one or more peptides, wherein a peptide of the composition comprises a sequence of amino acids other than a sequence of CD40, wherein the peptide binds to CD40 ligand (CD40L) and partially or completely inhibits interaction of CD40 with CD40L and one or more CD40-CD40L costimulatory effects. The peptide that binds to CD40L and partially or completely inhibits interaction of CD40 with CD40L and one or more CD40-CD40L costimulatory effects is a peptidomimetic or other composition not derived from the sequence of CD40 or other binding partner of CD40L e.g., Mac-1, and does not comprise a sequence of CD40 or other binding partner. For example, the peptide is not derived from the native Cd40-Cd40L interface and does not comprise a sequence thereof. In one example, the peptide comprises a sequence encoded by a nucleic acid fragment of a prokaryote genome or a compact eukaryote genome e.g., the peptide comprises a sequence of a natural open reading frame of a prokaryote genome or a compact eukaryote genome.

In another example, the peptide that binds to CD40L and partially or completely inhibits interaction of CD40 with CD40L and one or more CD40-CD40L costimulatory effects does not comprise both N-terminal and C-terminal cysteine residues for achieving conformational stability e.g., by virtue of disulfide bridge formation leading to cyclic peptide formation, which cyclic peptide formation may be advantageous for aptamer functionality. In another example, the peptide of the present invention comprises a single C-terminal or N-terminal cysteine residue. In another example, the peptide is cysteine-free.

In another example, the peptide that binds CD40L and partially or completely inhibits interaction of CD40 with CD40L and one or more CD40-CD40L costimulatory effects comprises one or more non-naturally-occurring amino acids e.g., one or more D amino acids. For example, the peptide is an isostere or a chiral analog such as a retroinverso-peptide analog (i.e., a retro-inverted peptide).

In another example, the peptide that binds to CD40L and partially or completely inhibits interaction of CD40 with CD40L and one or more CD40-CD40L costimulatory effects is a peptidyl-fusion. As used herein, the term "peptidyl fusion" means a peptide comprising two or more peptidyl moieties or sub-units linked covalently or non-covalently, with or without intervening linker or spacer moieties separating the peptidyl moieties. Preferred peptidyl fusions comprise two or more peptidyl moieties linked covalently e.g., by means of oxime chemistry or peptide synthesis or recombinant protein synthesis. For example, the peptidyl fusion may comprise a plurality of smaller peptides that each bind CD40L, wherein the peptidyl-fusion has a higher affinity for CD40L and/or enhanced inhibitory activity than a single peptide of the peptidyl-fusion. These smaller peptides that each bind CD40L may be the same or comprise the same sequence or secondary structure, or they may be structurally different e.g., with respect to their primary amino acid sequences or with respect to their secondary structures. For example, the peptidyl-fusion may be a dimer e.g., a homodimer or heterodimer comprising two peptides that each bind CD40L and partially or completely inhibits interaction of CD40 with CD40L and one or more CD40-CD40L costimulatory effects. In another example, a peptidyl-fusion is between a peptide that binds CD40L and a serum protein-binding moiety, or between a peptide that binds CD40L and a protein transduction domain, or between a peptide that binds CD40L and a serum protein-binding moiety. Peptidyl fusions comprising any combination of one or more peptides of the invention that bind CD40L and one or more other moieties e.g., a serum protein-binding moiety and/or a protein transduction domain and/or a serum protein-binding moiety, are also encompassed by the invention. As with base peptides, peptidyl fusions of the present invention may include one or more D-amino acids, and be isosteres or chiral analogs of peptides comprising L-amino acids.

Peptides, peptidyl fusions, isosteres and chiral analogs of the invention as described according to any example hereof may further comprise a polyethylene glycol (PEG) residue i.e., they may be PEGylated compositions. For example, the invention provides a peptide that binds to CD40L and partially or completely inhibits interaction of CD40 with CD40L and one or more CD40-CD40L costimulatory effects, wherein the peptide comprises a PEGylated peptide having L-amino acids or a PEGylated chiral analog thereof wherein all amino acids other than glycine have been substituted for D-amino acids. The PEGylated peptides and analogs may lack N-terminal and C-terminal cysteines or they may be cysteine-free.

In another example, the present invention provides a composition comprising a peptide that binds to CD40L and partially or completely inhibits interaction of CD40 with CD40L and one or more CD40-CD40L costimulatory effects, wherein the peptide comprises a sequence selected individually or collectively from the group consisting of:

(i) a sequence set forth in any one of SEQ ID NOs: 1 to 34 or 44;
(ii) the sequence of a functional fragment of any one of SEQ ID NOs: 1 to 34 or 44;
(iii) the sequence of a peptidyl fusion comprising a plurality of sequences at (i) or (ii), optionally wherein at least one of said plurality is separated by a spacer or linker molecule;
(iv) the sequence of (i) or (ii) or (iii) additionally comprising a protein transduction domain, e.g., a HIV tat basic region or a retroinverted analog thereof and/or a serum protein-binding moiety, optionally wherein said peptide is separated from the protein transduction domain and/or serum protein-binding moiety by a spacer or said protein transduction domain and/or serum protein-binding moiety are separated by one or more spacers; and
(v) an analog of any one of (i) to (iv) selected from the group consisting of (a) the sequence of any one of (i) to (iv) comprising one or more non-naturally-occurring amino acids; (b) the sequence of any one of (i) to (iv) comprising one or more non-naturally-occurring amino acid analogs; (c) an isostere of any one of (i) to (iv); (d) a retro-peptide analog of any one of (i) to (iv); and (e) a retro-inverted peptide analog of any one of (i) to (iv).

For the purposes of nomenclature, the sequences set forth in SEQ ID Nos: 1 to 44 are representative peptides of the present invention that bind to CD40L and inhibit the interaction of CD40 with a cognate receptor e.g., CD40, and inhibit downstream signaling from CD40L including costimulatory CD40-CD40L signaling e.g., B-cell proliferation such as determined by CD86 expression levels, and T-cell proliferation. It will also be apparent from Example 1 hereof that such peptidyl inhibitors include specific examples of cysteine-free peptides and peptidyl fusions, and retroinverted peptides, in both unmodified form and as PEGylated peptides and peptidyl fusions.

A further example of the present invention provides a phagemid vector or cell capable of expressing a peptide or peptidyl fusion of the present invention as described according to any example hereof comprising naturally-occurring amino acids or otherwise capable of being expressed by cellular translational machinery.

A still further example of the present invention provides an isolated nucleic acid comprising a sequence that encodes a peptide or peptidyl fusion of the present invention as described according to any example hereof.

In another example, the composition of the present invention is suitable for administration to a human or non-human animal. For example, the composition is formulated so as to comprise the active peptidyl agent and a pharmaceutically acceptable carrier and/or excipient.

In one example, the composition is a liquid pharmaceutical formulation comprising a buffer in an amount to maintain the pH of the formulation in a range of about pH 5.0 to about pH 7.0. In a further example, the pharmaceutical composition comprises an isotonizing agent in an amount to render same composition near isotonic. Exemplary isotonizing agents include sodium chloride e.g., present in said formulation at a concentration of about 50 mM to about 300 mM, or at a concentration of about 150 mM. Exemplary buffers are selected from the group consisting of succinate, citrate, and phosphate buffers e.g., at a concentration of about 1 mM to about 50 mM. For example, a sodium succinate or sodium citrate buffer at a concentration of about 5 mM to about 15 mM may be employed. In another example, the formulation further comprises a surfactant in an amount from about 0.001% to about 1.0% e.g., polysorbate 80 which may be present in said formulation in an amount from about 0.001% to about 0.5%.

Pharmaceutical compositions may be formulated for administration by injection, inhalation, ingestion or topically.

In one example, the formulation is for inhalation and the subject peptide is present in an amount suitable for administration by inhalation and the carrier or excipient is one suitable for inhalation. Inhalable formulations e.g., comprising an alkyl-saccharide transmucosal delivery-enhancing excipient such as Intraveil (Aegis Therapeutics) are preferred for prophylactic applications e.g., for administration to an asymptomatic subject at risk of developing a condition associated with CD40L signaling or a complication associated therewith e.g., an asymptomatic subject having one or more risk factors for a condition associated with CD40L signaling supra, and/or an asymptomatic subject exposed to an infectious agent, poison, allergen or irritant of the airways that is a risk factor for development of a condition associated with CD40L signaling.

By "asymptomatic subject" is meant a subject that does not exhibit one or more symptoms of a condition associated with CD40L signaling.

In another example, the formulation is for injection and the subject peptide is present in an amount suitable for administration by injection e.g., subcutaneously, intravenously, intraperitoneally or intramuscularly, and the carrier or excipient is one suitable for injection e.g., subcutaneously, intravenously, intraperitoneally or intramuscularly. Injectable formulations are preferred for acute phase a condition associated with CD40L signaling or complications associated therewith or where the subject has difficulty inhaling.

It is to be understood that it is a preferred embodiment for the peptidyl formulations of the present invention to have CD40L signaling inhibitory activity conferred by the peptide component or peptide analog component of such formulations.

The formulation may be packaged for multiple administrations e.g., it may be packaged as multiple injectable ampoules, capsules, etc. for repeated administration or repeated dosing.

The CD40L signaling inhibitor may be a peptidyl or non-peptidyl composition. Suitable peptidyl compounds will be any one or more of the peptides described herein above, or alternatively a different peptide or antibody composition that inhibits CD40L signaling e.g., as described in the ensuing Detailed Description. Suitable non-peptidyl compounds will be apparent to the skilled artisan based on the description herein, and include, for example, a nucleic acid, or a small molecule.

Again, the present invention clearly encompasses formulations comprising mixtures of peptides or peptide analogs.

In one example, a peptide or analog as described herein above or a peptidyl CD40L signaling inhibitor, is conjugated to or fused to a protein transduction domain. A suitable protein transduction domain will be apparent to the skilled artisan based on the description herein and includes a HIV-tat basic region peptide or a retroinverted analog thereof. Another suitable protein transduction domain is a Kaposi fibroblast growth factor (FGF) hydrophobic peptide protein transduction domain or a retro-inverted analog thereof.

The skilled artisan will be aware that an amount of the active ingredient will vary, e.g., as a result of variation in the bioactivity of an inhibitor, and/or the severity of the condition being treated. Accordingly, the term "amount" is not to be construed to limit the invention to a specific quantity, e.g., weight of active ingredient.

As used herein, the term "suitable carrier or excipient" shall be taken to mean a compound or mixture thereof that is suitable for use in a formulation albeit not necessarily limited in use to that context. In contrast, the term "a carrier or excipient" is compound or mixture thereof that is described in the art only with reference to a use in a formulation. The term "carrier or excipient for inhalation" shall be taken to mean a compound or mixture thereof that is suitable for use in a formulation to be administered to a subject by inhalation e.g., a formulation comprising an alkyl-saccharide transmucosal delivery-enhancing excipient such as Intraveil (Aegis Therapeutics). The term "carrier or excipient for injection" shall be taken to mean a compound or mixture thereof that is suitable for use in a formulation to be administered to a subject by injection.

A carrier or excipient useful in the formulation of the present invention will generally not inhibit to any significant degree a relevant biological activity of the active compound e.g., the carrier or excipient will not significantly inhibit the activity of the active compound with respect to reducing neutrophilic inflammation. Alternatively, or in addition, the carrier or excipient comprises a compound that enhances uptake and/or delivery and/or efficacy of the active compound.

Alternatively, or in addition, the carrier or excipient comprises a compound that enhances the activity of a peptide or analog as described herein above or, more generally, an CD40L signaling inhibitor and/or reduces inhibition of said peptide or analog or CD40L signaling inhibitor by degradative enzymes in the site of administration and/or en route to the site of action of a subject and or at the site of action. For example, the carrier or excipient may comprise a protease inhibitor and/or a DNase inhibitor and/or an RNase inhibitor to thereby enhance the stability of a peptide or analog as described herein above or a peptidyl CD40L signaling inhibitor.

In one example, the formulation as described herein according to any embodiment comprises an additional compound, such as, for example, a corticosterioid to further enhance the efficacy of the peptide or analog e.g., in anti-inflammatory applications. Suitable additional compounds will be apparent to the skilled artisan based on the description herein.

The present invention also provides a method for producing a formulation described herein according to any embodiment. For example, such a method comprises mixing or otherwise combining a peptide or analog as described herein above or CD40L signaling inhibitor in an amount sufficient to reduce or prevent a CD40L-mediated signaling event with a suitable carrier or excipient e.g., a carrier or excipient for inhalation or injection. In one example, the method additionally comprises producing or obtaining said peptide or analog or CD40L signaling inhibitor. For example, a peptide or analog or CD40L signaling inhibitor is produced synthetically or recombinantly, using a method known in the art and/or described herein.

The composition of the invention is suitable for use in medicine e.g., in a method of treatment of the human or animal body by prophylaxis or therapy, or for use in research e.g., in a method of drug screening, drug development or clinical trial. For example, a composition of the invention according to any example hereof is for competitively antagonizing or inhibiting interaction between CD40L and CD40 in medicine and/or for research. In another example, a composition of the invention according to any example hereof is for modulating CD40L-dependent signaling mediated by CD40L and/or CD40, including costimulatory CD40-CD40L signaling. In another example, a composition of the invention according to any example hereof is for modulating CD40L-dependent signaling mediated by CD40L and/or Mac-1, including costimulatory CD40-Mac-1 signaling. In another example, a composition of the invention according to any example hereof is for use in a method of prophylaxis and/or therapy of one or more adverse effects or consequences of CD40L-dependent signaling mediated by CD40L and/or CD40 and/or Mac-1. In another example, a composition of the invention according to any example hereof is inhibiting or reducing expression of CD86 on B-cells and/or downstream signaling from CD86. In another example, a composition of the invention according to any example hereof is for antagonizing or inhibiting or reducing proliferation or differentiation of B-cells and/or antibody production by B-cells. In another example, a composition of the invention according to any example hereof is for antagonizing or inhibiting or reducing proliferation or differentiation of T-cells and/or T-cell-mediated humoral immunity. In another example, a composition of the invention according to any example hereof is for use in the prophylaxis or therapy of inflammation. In another example, a composition of the invention according to any example hereof is for use in the prophylaxis or therapy of an autoimmune disease. In another example, a composition of the invention according to any example hereof is for use in the attenuation or alleviation or amelioration of an inappropriate or adverse humoral immune response in a subject. In another example, a composition of the invention according to any example hereof is for use in preventing or attenuating humoral immunity against one or more therapeutic proteins e.g., clotting agent(s) and/or cytokine(s).

In related examples, the present invention provides for use of a composition of the invention according to any example hereof in medicine and/or in the preparation of a medicament for antagonizing or inhibiting or reducing B-cell proliferation and/or antibody production and/or for antagonizing or inhibiting or reducing T-cell proliferation and/or for use in the prophylaxis or therapy of inflammation and/or for use in the prophylaxis or therapy of autoimmunity and/or for use in preventing or attenuating humoral immunity against one or more clotting factors in the treatment of hemophilia and/or for use in preventing or attenuating humoral immunity against one or more cytokines in the treatment of a viral infection and/or for use in preventing or attenuating humoral immunity against one or more cytokines in the treatment of a cancer or metastatic disease.

The present invention also provides a method of preventing or treating one or more adverse consequences of CD40L-dependent signaling in a subject, said method comprising administering an amount of a composition of the invention according to any example hereof for a time and under conditions sufficient to inhibit aberrant or inappropriate CD40L-dependent signaling. In one example, this invention provides a method of preventing or treating inflammation in a subject, said method comprising administering an amount of a composition of the invention according to any example hereof for a time and under conditions sufficient to ameliorate one or more adverse effects of CD40L-dependent signaling that contribute to an inflammatory response in a subject. In another example, the invention provides a method of preventing or treating autoimmunity in a subject, said method comprising administering an amount of a composition of the invention according to any example hereof for a time and under conditions sufficient to ameliorate one or more adverse effects of CD40L-dependent signaling that contribute to autoimmunity in a subject. In another example, this invention provides a method of preventing or treating cancer or metastatic disease in a subject, said method comprising administering an amount of a composition of the invention according to any example hereof for a time and under conditions sufficient to ameliorate one or more adverse effects of CD40L-dependent signaling that contribute to cancer in a subject.

The present invention also provides a method of treatment of any disease or condition involving a humoral immune response, said method comprising administering an amount of a composition of the invention according to any example hereof for a time and under conditions sufficient to attenuate or reduce humoral immunity against a therapeutic protein administered to the subject for treatment or prevention of the disease or condition. In such applications, the compositions may be administered concomitantly with or before or after administering the therapeutic protein to the subject. For example, this invention provides a method of treating a viral infection in a subject, said method comprising administering an amount of the composition for a time and under conditions sufficient to attenuate or reduce humoral immunity against a cytokine administered to the subject. In another example, the invention provides a method of treating hemophilia, said method comprising administering an amount of the composition for a time and under conditions sufficient to attenuate or reduce humoral immunity against a clotting factor administered to the subject.

In a related example, the present invention provides a method for inhibiting, reducing or delaying or otherwise preventing one or more CD40L-mediated events or phenotypes in a cell or a subject, said method comprising providing to the cell or subject a peptide that binds specifically to a CD40L to thereby ameliorate or inhibit or reduce or antagonize one or more CD40L-mediated events or phenotypes according to any example hereof.

In a related example, the present invention provides a method for inhibiting or otherwise modulating a CD40L-mediated signaling pathway in a cell, said method comprising contacting said cell with an effective amount of one or more CD40L peptide inhibitors of the present invention according to any embodiment hereof. In one example, the CD40L-mediated event is binding of CD40L to CD40. In another example, the CD40L-mediated event is binding of CD40L to Mac-1. In another example, the CD40L-mediated event is a cellular process mediated by CD40L binding to CD40. In another example, the CD40L-mediated event is a cellular process mediated by CD40L binding to Mac-1. In another example, the CD40L-mediated event is an inflammatory response e.g., in the vascular system, gastrointestinal system, respiratory system, nervous system, or other organ system of an animal subject e.g., as determined by a cellular response ex vivo in a cell derived from an animal subject. In accordance with this example, the method of the invention may be employed to treat or prevent an inflammatory response characterized by interaction of CD40L with CD40 and/or Mac-1 in one or more of said organs or a cell or tissue thereof, wherein an effective amount of a CD40L peptide inhibitor of the invention or an analog or derivative thereof according to any example hereof is administered to a subject in need thereof. In another example, the CD40L-mediated event is a development or complication of atherosclerosis, or formation of an atherosclerotic lesion, or aggravation or complication of an atherosclerotic lesion. In accordance with this example, the method of the invention may be employed to treat or prevent atherosclerosis or an atherosclerotic lesion or to promote a vascular repair process e.g., by inhibiting angiogenesis and/or neovascularization process(es) characterized by interaction of CD40L with CD40 and/or Mac-1, wherein an effective amount of a CD40L peptide inhibitor of the invention or an analog or derivative thereof according to any example hereof is administered to a subject in need thereof. In another example, the CD40L-mediated event is carcinogenesis or metastasis associated therewith. For example, the method of the invention may be employed to treat or prevent one or more cancers, characterized by interaction of CD40L with CD40, wherein an effective amount of a CD40L peptide inhibitor of the invention or an analog or derivative thereof according to any example hereof is administered to a subject in need thereof. Exemplary cancers the treatment of which the invention may be useful are selected from the group consisting of a non-Hodgkins lymphoma, chronic lymphocytic leukemia, multiple myeloma, B cell lymphoma, high-grade B cell lymphoma, intermediate-grade B cell lymphoma, low-grade B cell lymphoma, B cell acute lympohoblastic leukemia, myeloblastic leukemia, and Hodgkin's disease.

In a related example, the present invention provides a method for inhibiting, reducing or delaying growth or differentiation of a B-cell e.g., a normal human B-cell, said method comprising contacting said B-cell with an effective amount of one or more CD40L peptide inhibitors of the present invention according to any embodiment hereof. In one example, the present invention provides a method for inhibiting, reducing or delaying proliferation of a B-cell e.g., a normal human B cell wherein said proliferation is augmented by the interaction of a CD40 ligand with CD40 expressed on the surface of said B-cell, said method comprising contacting said B-cell with an effective amount of one or more CD40L peptide inhibitors of the present invention according to any embodiment hereof. In a further example, the present invention provides a method for inhibiting, reducing or delaying antibody production by B cells in a human patient, said method comprising administering to the subject an effective amount of one or more CD40L peptide inhibitors of the present invention according to any embodiment hereof. In a further example, the present invention provides a method for inhibiting, reducing or delaying growth of a cancer cell of B cell lineage, said method comprising contacting said B-cell with an effective amount of one or more CD40L peptide inhibitors of the present invention according to any embodiment hereof. Exemplary cancers the treatment of which the invention may be useful are selected from the group consisting of a non-Hodgkins lymphoma, chronic lymphocytic leukemia, multiple myeloma, B cell lymphoma, high-grade B cell lymphoma, intermediate-grade B cell lymphoma, low-grade B cell lymphoma, B cell acute lympohoblastic leukemia, myeloblastic leukemia, and Hodgkin's disease.

In a further related example, the present invention provides a method for inhibiting or preventing an autoimmune disease in a subject or reducing the severity of an autoimmune disease in a subject, said method comprising administering to a subject in need thereof an effective amount of one or more CD40L peptide inhibitors of the present invention according to any embodiment hereof. The autoimmune disease may be selected e.g., from the group consisting of systemic lupus erythematosus, autoimmune thrombocytopenic purpura, rheumatoid arthritis, multiple sclerosis, ankylosing spondylitis, myasthenia gravis, and pemphigus vulgaris.

DETAILED DESCRIPTION OF THE INVENTION

CD40 and/or CD40L Signaling Inhibitors

Figure 1:
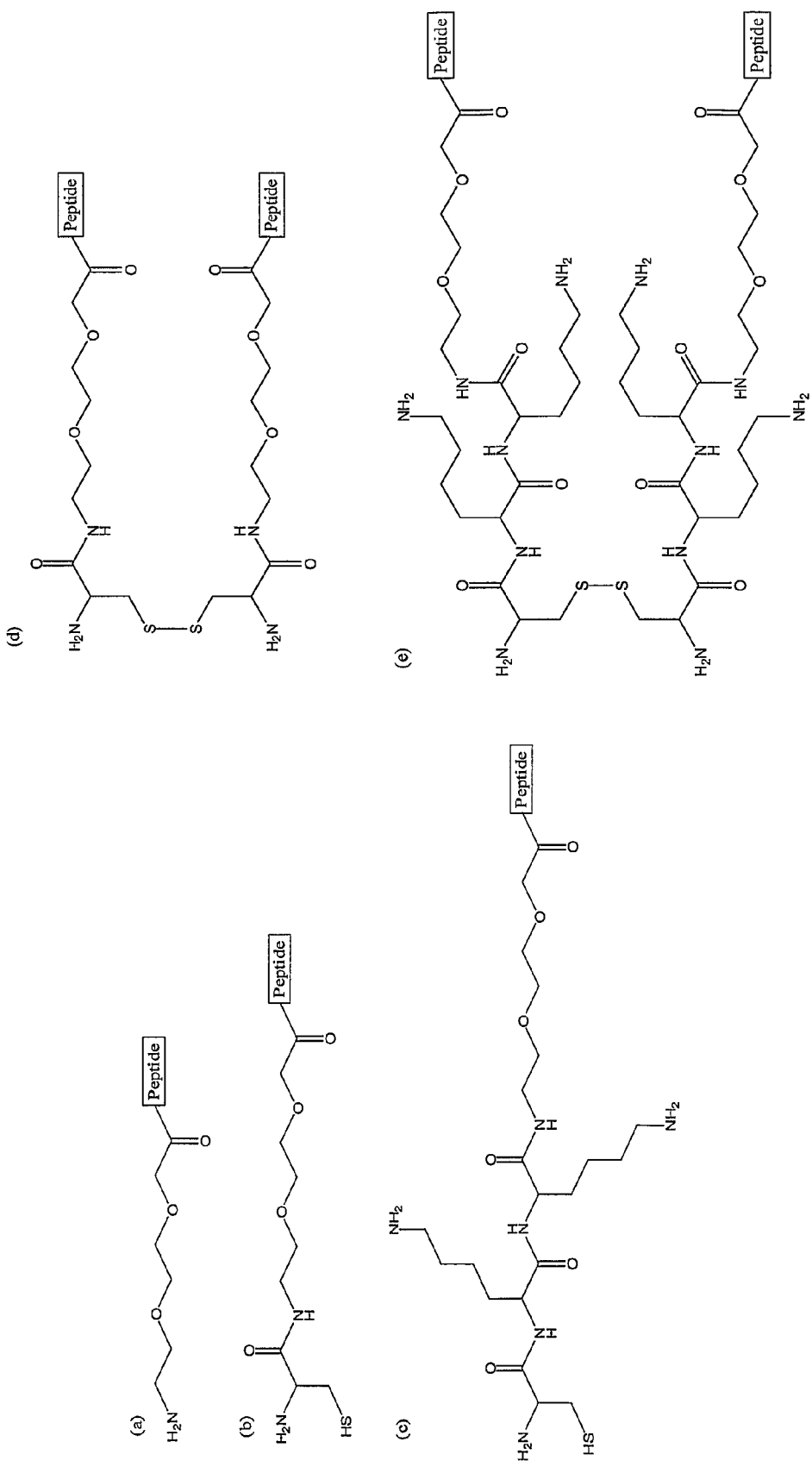
FIG. 1a is a schematic representation showing a CD40L peptide inhibitor derivative comprising a CD40L peptide inhibitor of the invention bound to 8-amino-3,6-dioxaoctanyl linker or spacer molecule.
FIG. 1b is a schematic representation showing a CD40L peptide inhibitor derivative comprising the derivative of FIG. 5a wherein the linker or spacer moiety additionally comprises N-terminal cysteine.
FIG. 1c is a schematic representation showing a CD40L peptide inhibitor derivative comprising the derivative of FIG. 5a wherein the linker or spacer moiety additionally comprises the N-terminal peptide sequence Cys-Lys-Lys (i.e., CKK).
FIG. 1d is a schematic representation showing a CD40L peptide inhibitor derivative comprising a dimer produced between two CD40L peptide inhibitors as shown in FIG. 1b wherein the monomers are linked chemically by disulfide bridge formation between N-terminal cysteine residues.
FIG. 1e is a schematic representation showing a CD40L peptide inhibitor derivative comprising a dimer produced between two CD40L peptide inhibitors as shown in FIG. 1c wherein the monomers are linked chemically by disulfide bridge formation between N-terminal cysteine residues.
Figure 2:
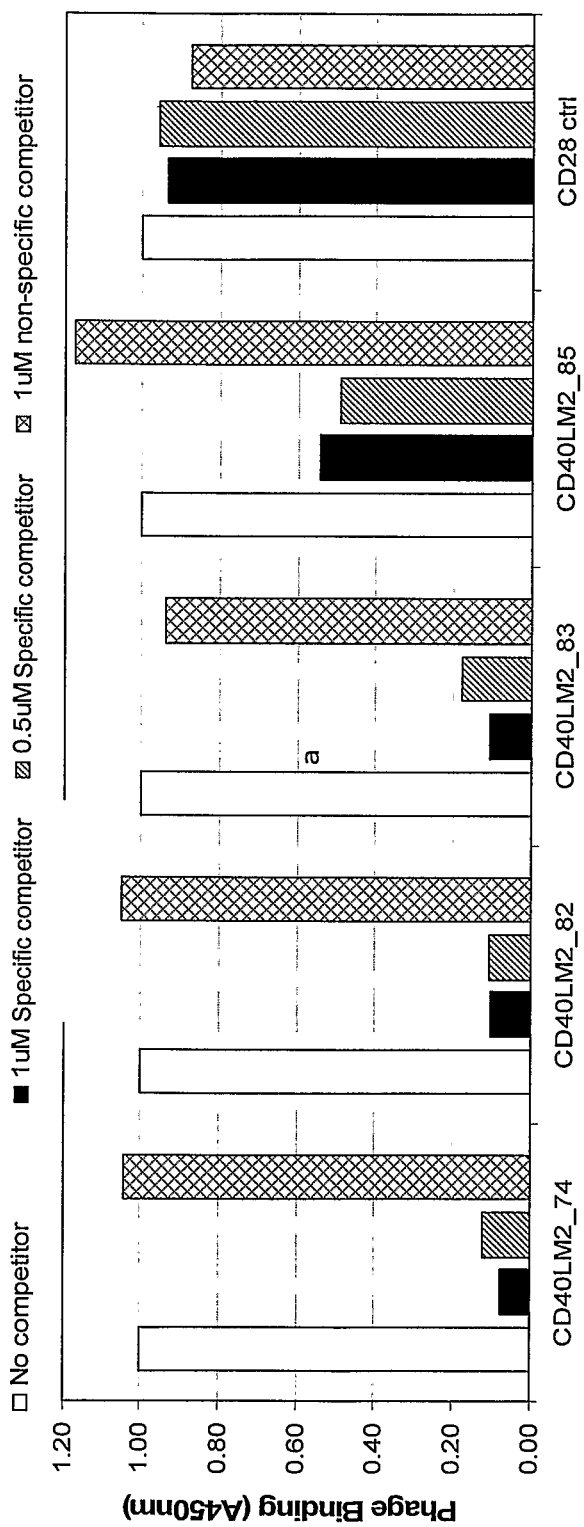
FIG. 2 is a graphical representation showing the effect of a specific competitor comprising a soluble CD40L protein, or a non-specific competitor, on binding of the phage expressing peptide inhibitors of CD40L signaling shown on the x-axis to immobilized CD40L in a multiwell assay format. Data indicate specific binding of all phage indicated other than the CD28 control phage, to CD40L.
Figure 3:
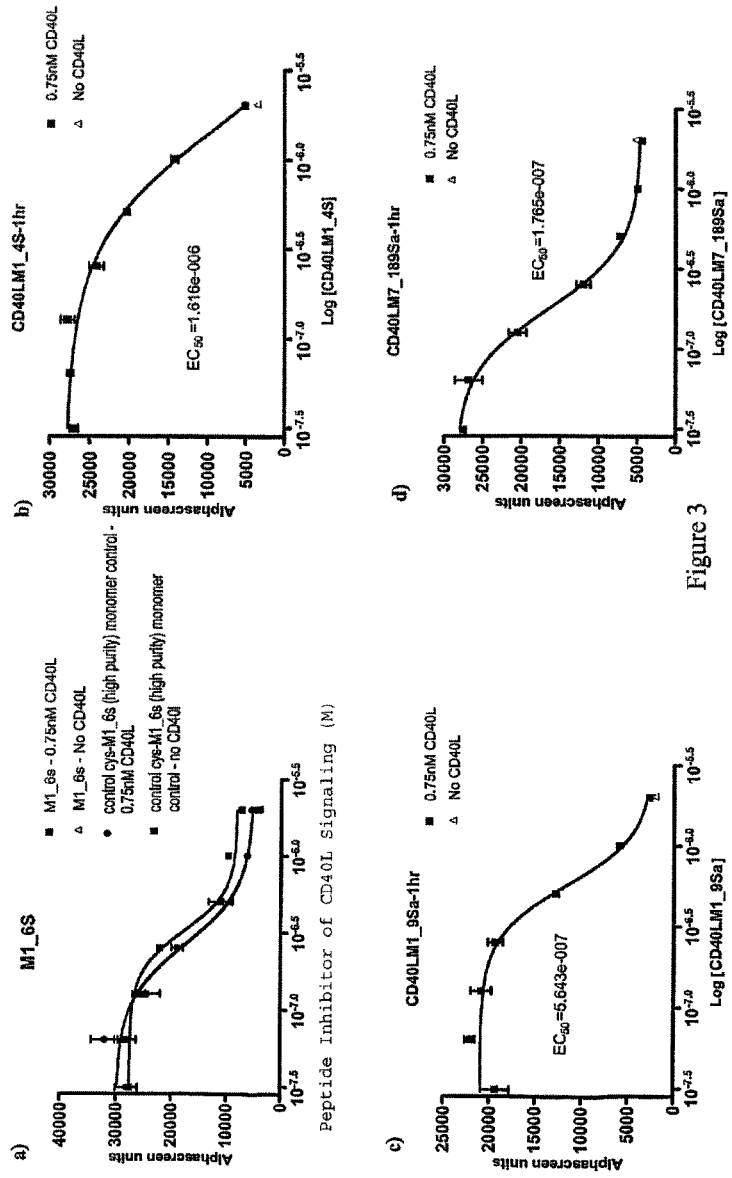
FIG. 3a is a graphical representation showing inhibition of the interaction between CD40L and 0040 by the peptide inhibitor of CD40L signaling M1_6 and a derivative thereof comprising an N-terminal cysteine residue (Cys-M1_6S) by Alphascreen proximity assay (Perkin Elmer, USA).
FIG. 3b is a graphical representation showing inhibition of the interaction between CD40L and 0040 by the peptide inhibitor of CD40L signaling M1_4S by Alphascreen proximity assay (Perkin Elmer, USA).
FIG. 3c is a graphical representation showing inhibition of the interaction between CD40L and CD40 by the peptide inhibitor of CD40L signaling M1_9Sa by Alphascreen proximity assay (Perkin Elmer, USA).
FIG. 3d is a graphical representation showing inhibition of the interaction between CD40L and CD40 by the peptide inhibitor of CD40L signaling M1_189Se by Alphascreen proximity assay (Perkin Elmer, USA).

The compositions as described herein according to any embodiment may comprise any one or more peptidyl or non-peptidyl CD40 signaling inhibitors and/or CD40L signaling inhibitors.

By "peptidyl inhibitor" is meant a composition that reduced or antagonizes the activity or effect of a stated integer e.g., CD40L or CD40 or downstream signaling from CD40L or CD40, wherein the active agent having such an inhibitory activity is a peptide.

By "non-peptidyl inhibitor" is meant a composition that reduced or antagonizes the activity or effect of a stated integer e.g., CD40L or CD40 or downstream signaling from CD40L or CD40, wherein the active agent having such an inhibitory activity is not a peptide.

For example, a peptidyl or non-peptidyl inhibitor of the present invention binds to or interacts with CD40L and inhibits CD40L-mediated activity. The peptidyl or non-peptidyl inhibitor may prevent or reduce the ability of CD40L to bind to CD40 and mediate one or more CD40-dependent signaling events. For example, a peptidyl inhibitor capable of binding to CD40L and reducing or preventing CD40-CD40L interaction will inhibit CD40-mediated Cd86 expression and/or one or more downstream CD86-mediated events. In another example, a peptidyl inhibitor capable of binding to CD40L and reducing or preventing CD40-CD40L interaction will inhibit or reduce CD40L-mediated T-cell proliferation.

As used herein, the term "CD40 signaling" shall be taken to mean one or more downstream pathway steps or effects mediated by CD40 and dependent on CD40L binding to CD40. The term "CD40L-dependent CD40-mediated" also refers to CD40 signaling as defined herein. For example, a peptidyl inhibitor of the present invention may modulate e.g., antagonize CD40 signaling by virtue of preventing CD40 from binding to CD40L.

The term "CD40L signaling" shall be taken to mean one or more downstream pathway steps or effects mediated by CD40L whether or not binding to the cognate CD40 receptor is involved. For example, a peptidyl inhibitor of the present invention may modulate e.g., antagonize CD40L signaling that does not involve CD40, by virtue of binding directly to CD40L, or alternatively, a peptidyl inhibitor of the present invention may modulate e.g., antagonize CD40L signaling that does involve CD40, by virtue of preventing CD40 from binding to CD40L.

1. Peptidyl Inhibitors of CD40 and/or CD40L Signaling

A peptidyl inhibitor described herein may be a base peptide or derivative or analog according to any example hereof, that functions as a CD40 signaling inhibitor and/or a CD40L signaling inhibitor.

The term "base peptide" refers to a peptide in an unmodified form that possesses a stated inhibitory activity or binding activity, especially CD40L-binding activity and/or CD40L-signaling inhibitory activity and/or CD40-signaling inhibitory activity e.g., by virtue or preventing an interaction between CD40L and CD40 that activates the CD40:CD40L costimulatory pathway.

The term "derivative" or "analog" in the context of a peptidyl inhibitor refers broadly to a peptide in a modified form that possesses a stated inhibitory activity or binding activity, especially CD40L-binding activity and/or CD40L-signaling inhibitory activity and/or CD40-signaling inhibitory activity e.g., by virtue or preventing an interaction between CD40L and CD40 that activates the CD40:CD40L costimulatory pathway.

Peptide Synthesis

A peptide or an analog or derivative thereof is preferably synthesized using a chemical method known to the skilled artisan. For example, synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, J. Am. Chem. Soc., 85:2149-2154, 1963, or the base-labile Nα-amino protected 9-fluorenylmethoxycarbonyl (Fmoc) amino acids described by Carpino and Han, J. Org. Chem., 37:3403-3409, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of a peptide of the present invention or an analog or derivative thereof.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

A peptide, analog or derivative as described herein can also be chemically prepared by other methods such as by the method of simultaneous multiple peptide synthesis. See, e.g., Houghten Proc. Natl. Acad. Sci. USA 82: 5131-5135, 1985 or U.S. Pat. No. 4,631,211.

As will be apparent to the skilled artisan based on the description herein, an analog or derivative of a peptide of the invention may comprise D-amino acids, a combination of D- and L-amino acids, and various unnatural amino acids (e.g., α-methyl amino acids, Cα-methyl amino acids, and Nα-methyl amino acids, etc) to convey special properties. Synthetic amino acids include ornithine for lysine, fluorophenylalanine for phenylalanine, and norleucine for leucine or isoleucine. Methods for the synthesis of such peptides will be apparent to the skilled artisan based on the foregoing description.

Recombinant Peptide Production

A peptide or analog or derivative thereof or fusion protein may be produced as a recombinant protein. To facilitate the production of a recombinant peptide or fusion protein nucleic acid encoding same is preferably isolated or synthesized. Typically the nucleic acid encoding the recombinant protein is/are isolated using a known method, such as, for example, amplification (e.g., using PCR or splice overlap extension) or isolated from nucleic acid from an organism using one or more restriction enzymes or isolated from a library of nucleic acids. Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For expressing protein by recombinant means, a protein-encoding nucleic acid is placed in operable connection with a promoter or other regulatory sequence capable of regulating expression in a cell-free system or cellular system. For example, nucleic acid comprising a sequence that encodes a peptide is placed in operable connection with a suitable promoter and maintained in a suitable cell for a time and under conditions sufficient for expression to occur. Nucleic acid encoding a peptide inhibitor of CD40L-dependent signaling, including CD40L-dependent CD40-mediated signaling event(s), is described herein or is derived from the publicly available amino acid sequence.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid (e.g., a transgene), e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid (e.g., a transgene and/or a selectable marker gene and/or a detectable marker gene) to which it is operably linked. Preferred promoters can contain additional copies of one or more specific regulatory elements to further enhance expression and/or alter the spatial expression and/or temporal expression of said nucleic acid.

As used herein, the term "in operable connection with", "in connection with" or "operably linked to" means positioning a promoter relative to a nucleic acid (e.g., a transgene) such that expression of the nucleic acid is controlled by the promoter. For example, a promoter is generally positioned 5' (upstream)

to the nucleic acid, the expression of which it controls. To construct heterologous promoter/nucleic acid combinations (e.g., promoter/nucleic acid encoding a peptide), it is generally preferred to position the promoter at a distance from the gene transcription start site that is approximately the same as the distance between that promoter and the nucleic acid it controls in its natural setting, i.e., the gene from which the promoter is derived. As is known in the art, some variation in this distance can be accommodated without loss of promoter function.

Should it be preferred that a peptide or fusion protein of the invention is expressed in vitro a suitable promoter includes, but is not limited to a T3 or a T7 bacteriophage promoter (Hanes and Plückthun *Proc. Natl. Acad. Sci. USA*, 94 4937-4942 1997).

Typical expression vectors for in vitro expression or cell-free expression have been described and include, but are not limited to the TNT T7 and TNT T3 systems (Promega), the pEXP1-DEST and pEXP2-DEST vectors (Invitrogen).

Typical promoters suitable for expression in bacterial cells include, but are not limited to, the lacz promoter, the Ipp promoter, temperature-sensitive λL or λR promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, and include, for example, PKC30 (Shimatake and Rosenberg, *Nature* 292, 128, 1981); pKK173-3 (Amann and Brosius, *Gene* 40, 183, 1985), pET-3 (Studier and Moffat, *J. Mol. Biol.* 189, 113, 1986); the pCR vector suite (Invitrogen), pGEM-T Easy vectors (Promega), the pL expression vector suite (Invitrogen) the pBAD/TOPO or pBAD/thio—TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer Inc., CT, USA); the pQE series of expression vectors (QIAGEN, CA, USA), or the pL series of expression vectors (Invitrogen), amongst others.

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (e.g., 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSRαtkneo (Muller et al., *Mol. Cell. Biol.*, 11, 1785, 1991).

A wide range of additional host/vector systems suitable for expressing a peptide or fusion protein of the present invention are available publicly, and described, for example, in Sambrook et al (In: Molecular cloning, A laboratory manual, second edition, Cold Spring Harbor Laboratory, Cold Spring Harbor, N.Y., 1989).

In other examples, the peptidyl inhibitor, especially any base peptide, is expressed on by phage display, cell display, or in vitro display.

For in vitro display, the expressed peptide is linked to the nucleic acid from which it was expressed such that said peptide is presented in the absence of a host cell. For example, the peptide is displayed by ribosome display, which directly links mRNA encoded by an expression construct to the peptide that it encodes. To display a nascent polypeptide in vitro, nucleic acid encoding it is cloned downstream of an appropriate promoter (e.g., bacteriophage T3 or T7 promoter) and a ribosome binding sequence, optionally including a translatable spacer nucleic acid (e.g., encoding amino acids 211-299 of gene III of filamentous phage M13 mp19) that stabilizes the expressed fusion protein within the ribosomal tunnel. Ribosome complexes are stabilized against dissociation from the peptide and/or its encoding mRNA by the addition of reagents such as, for example, magnesium acetate or chloroamphenicol.

For phage display, the expressed peptide is displayed on the surface of a bacteriophage, as described e.g., in U.S. Pat. No. 5,821,047 and U.S. Pat. No. 6,190,908. In general, nucleic acid comprising a sequence encoding the peptide is fused N-terminally or C-terminally to nucleic acid comprising a sequence encoding a phage coat protein e.g., M13 protein-3 (p3), M13 protein-7 (p7), or M13, protein-8 (p8).

In one example, a peptidyl inhibitor of the present invention is expressed C-terminally in a Fos fusion peptide i.e., as Fos-peptidyl inhibitor fusion in the phagemid vector pJuFo. The vector pJuFo also expresses p3 C-terminally in a c-Jun fusion peptide i.e., as c-Jun-p3. By virtue of the interaction between c-Jun and Fos, the inhibitory peptide of the present invention is displayed from pJuFo in trans as a dimer between the Fos-peptidyl inhibitor and c-Jun-p3 fusion peptides.

Alternatively, a peptidyl inhibitor of the present invention is expressed N-terminally as a p3 or p7 or p8 fusion peptide wherein the C-terminus of the peptide is fused to the N-terminus of p3 or p7 or p8. Nucleic acid encoding the peptidyl inhibitor is cloned into an insertion site in a suitable vector e.g., an EcoRI site or other restriction site, positioned such that the encoded peptidyl inhibitor is expressed as an in-frame fusion with the p3 or p7 or p8 protein.

A leader sequence e.g., PelB, comprising a translation start codon is generally positioned upstream of the insertion site. Preferably, the vector is configured so as to provide for expression of natural open reading frames in the introduced nucleic acid encoding the peptidyl inhibitor e.g., by ensuring the absence of intervening stop codons between the leader sequence and the p3 or p7 or p8 protein. The introduced nucleic acid may also be cloned in different reading frames to achieve this read-through.

Optionally, the peptidyl inhibitor-p3 or peptidyl inhibitor-p7 or peptidyl inhibitor-p8 fusion peptide is also a fusion with an intervening haemagglutinin (HA) tag moiety e.g., upstream of the p3/p7/p8 sequence and downstream of the peptidyl inhibitor in the fusion peptide. The nucleic acid encoding the HA tag moiety is generally modified to remove the amber stop codon to thereby permit translational read-through from the 5'-end of sequence encoding the peptidyl inhibitor to the p3 or p7 or 8 moiety.

Optionally, the fusion peptide comprises a cysteine residue positioned e.g., at the N-terminus of the peptidyl inhibitor moiety or at the C-terminus of the peptidyl inhibitor moiety or at the N-terminus of the p3 or p7 or p8 moiety or at the N-terminus of a HA-p3 or HA-p7 or HA-p8 moiety. In one example, the phagemid vector is engineered to provide a terminal cysteine residue or internal cysteine residue for the fusion peptide, preferably a single terminal cysteine residue or single internal cysteine residue e.g., introduced by mutation at the 5'-end of the coding sequence of p3 or p7 or p8. The presence of a single cysteine permits the expressed inhibitory peptide to form an intramolecular disulfide bridge between a sulfhydryl residue in the expressed inhibitory peptide, if present, and the N-terminal sulfhydryl residue of the p3 moiety or the p7 moiety or the p8 moiety or the HA-p3 moiety or the HA-p7 moiety or the HA-p8 moiety. Alternatively, the inclusion of a cysteine at the N-terminus or C-terminus of the peptidyl inhibitor permits the expressed inhibitory peptide to form an intramolecular disulfide bridge between the sulfhydryl residue of that cysteine and a sulfhydryl residue in the expressed inhibitory peptide, if present. It is not preferred for the phagemid vector to encode multiple cysteines in that portion of the p3 or p7 or p8 fusion peptide lacking the peptidyl inhibitor, and/or for a peptidyl inhibitor per se to comprise multiple cysteines when the phagemid vector encodes a cysteine residue in that portion of the p3 or p7 or p8 fusion peptide lacking the peptidyl inhibitor. Accordingly, in another example, the phagemid vector encodes a single cysteine in that portion of the p3 or p7 or p8 fusion peptide lacking the peptidyl inhibitor, and/or a peptidyl inhibitor comprises a single cysteine e.g., when the phagemid vector encodes a cysteine residue in that portion of the p3 or p7 or p8 fusion peptide lacking the peptidyl inhibitor.

The sequence encoding a fusion peptide according to any example hereof is displayed from an appropriate vector, e.g., a vector capable of replicating in bacterial cells. Suitable host cells e.g., *E. coli*, are then transformed with the recombinant vector. Said host cells are also infected with a helper phage particle encoding an unmodified form of the coat protein to which a nucleic acid fragment is operably linked. Transformed, infected host cells are cultured under conditions suitable for forming recombinant phagemid particles comprising more than one copy of the fusion protein on the surface of the particle. This system has been shown to be effective in the generation of virus particles such as, for example, a virus particle selected from the group comprising λ phage, T4 phage, M13 phage, T7 phage and baculovirus. Such phage display particles are then screened to identify a displayed protein having a conformation sufficient for binding to a target protein or nucleic acid.

Means for introducing the isolated nucleic acid molecule or a gene construct comprising same into a cell for expression are well-known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

In another example, the peptide derivative comprises an N-terminal and/or C-terminal cysteine residue e.g., to facilitate intramolecular cross-linking or intermolecular cross-linking with another peptide such as the same or a different peptidyl inhibitor e.g., to form a multimeric peptide, or to facilitate intermolecular cross-linking with a different moiety e.g., phage p3 protein, phage p8 protein, PEG, serum protein-binding peptide. In another example, the peptide derivative comprises an N-terminal cysteine residue. In another example, the peptide derivative comprises a C-terminal cysteine residue. In another example, the peptide derivative does not comprise both an N-terminal and a C-terminal cysteine residue e.g., because the peptide autonomously forms a stable conformation thereby avoiding the need for cyclization mediated via disulfide bond/bridge formation between N-terminal and C-terminal cysteine residues. In another example, the peptide derivative is not capable of forming or does not form intramolecular disulfide bonds/bridges or cross-links e.g., because the peptide autonomously forms a stable conformation not requiring intramolecular disulfide constraint.

Preferred CD40- and/or CD40L-signaling inhibitory peptides for use in the treatment or prophylaxis of one or more CD40L-mediated effects, especially one or more adverse consequences of aberrant CD40L-mediated signaling or CD40-mediated signaling are mimetic peptides that do not merely comprise a sequence corresponding to a fragment of a native protein that they inhibit to prevent it binding to its cognate partner or substrate e.g., they are not dominant negative mutants such as fragments of the native CD40-CD40L interface.

Protein Transduction Domains

To facilitate entry into a cell, a peptidyl inhibitor described herein, including a base peptide or derivative or analog according to any example hereof, may be conjugated to a protein transduction domain, synthesized to include a protein transduction domain, or expressed recombinantly as a fusion protein comprising a protein transduction domain. As used herein, the term "protein transduction domain" shall be taken to mean a peptide or protein that is capable of enhancing, increasing or assisting penetration or uptake of a compound conjugated to the protein transduction domain into a cell either in vitro or in vivo. Those skilled in the art will be aware that synthetic or recombinant peptides can be delivered into cells through association with a protein transduction domain such as the TAT sequence from HIV or the Penetratin sequence derived from the Antennapaedia homeodomain protein (see, for example, Temsamani and Vidal, *Drug Discovery Today* 9: 1012-1019, 2004, for review).

A suitable protein transduction domain will be known to the skilled artisan and includes, for example, HIV-1 TAT fragment, signal sequence based peptide 1, signal sequence based peptide 2, transportan, amphiphilic model peptide, polyarginine, or a Kaposi fibroblast growth factor (FGF) hydrophobic peptide protein transduction domain. Additional suitable protein transduction domains are described, for example, in Zhao and Weisledder *Medicinal Research Reviews*, 24: 1-12, 2004 and Wagstaff and Jans, *Current Medicinal Chemistry*, 13: 1371-1387, 2006.

A protein transduction domain is covalently attached to the N-terminus or C-terminus of a peptidyl inhibitor of the present invention, and may be a chiral analog e.g., a retroinverso peptidyl moiety or PEGylated moiety. For example, a peptidyl fusion comprising a protein transduction domain positioned N-terminal to a peptidyl inhibitor of the present invention may be produced by standard peptide synthesis means or recombinant means without the exercise of undue experimentation based on the disclosure herein. Retroinverted peptide analogs comprising a protein transduction domain positioned N-terminal to a peptidyl inhibitor of the present invention, wherein the complete sequence is retroinverted are particularly preferred and produced without inventive effort based on the disclosure herein. Peptidyl fusions comprising a protein transduction domain and a peptidyl inhibitor of the present invention may comprise a spacer or linker moiety separating protein transduction domain and peptidyl inhibitor. Alternatively, the protein transduction domain and peptidyl inhibitor may be adjacent or juxtaposed in the peptidyl fusion.

Serum Protein Moieties

As used herein, the term "serum protein moiety" shall be taken to refer to any serum protein, protein fragment or peptide having a long half life e.g., serum albumin, immunoglobulin, antibody fragment, transferrin, ferritin or other serum protein, having a long half life. By "long half life" is meant a half life in serum approximately the same as an albumin protein e.g., human serum albumin. In this respect, it is preferred for a serum protein moiety to confer on a peptidyl inhibitor of the present invention administered to a subject, including any base peptide or derivative or analog thereof, a half-life that is at least about 25% or 50% or 75% or 90% or 95% or 99% the half-life of an endogenous serum albumin protein e.g., a murine animal or primate such as a human. For example, human serum albumin has a half life in humans of 19 days e.g., Peters et al., Adv. Protein Chem. 37, 161-245 (1985), and a half-life in mice of about 35 hours e.g., Chaudhury et al., J. Exp. Med. 197, 315-322 (2003).

A preferred serum protein moiety is an immunoglobulin fragment. By "immunoglobulin fragment" is meant any derivative of an immunoglobulin wherein the undesired effector function of Fc has been disabled or deleted, and wherein the fragment has a long half life. For example, an immunoglobulin fragment may be an Fc-disabled antibody, immunoglobulin isotype not producing undesirable side-effects, or a modified Fc not producing undesirable Fc effector function. One preferred example of an Fc-disabled antibody is a CovXBody comprising a hapten linker and Fc-disabled antibody (CovX Research LLC, San Diego Calif. 92121, USA). The peptidyl inhibitor of the present invention may be linked to a CovXBody via the hapten linker moiety of the CovXBody according to the manufacturer's instructions.

A serum protein moiety is generally covalently attached to the N-terminus or C-terminus of a peptidyl inhibitor of the present invention. For example, a peptidyl fusion comprising a serum protein moiety positioned N-terminal or C-terminal to a peptidyl inhibitor of the present invention may be produced by standard peptide synthesis means or recombinant means without the exercise of undue experimentation based on the disclosure herein. Peptidyl fusions comprising a serum protein moiety and a peptidyl inhibitor of the present invention may comprise a spacer or linker moiety separating serum protein moiety and peptidyl inhibitor. Alternatively, the serum protein moiety and peptidyl inhibitor may be adjacent or juxtaposed in the peptidyl fusion.

Particularly preferred serum protein moieties for use in the present invention are retro-inverted peptides e.g., comprising a retroinverted analog of one or more serum protein moieties.

Serum Protein-Binding Moieties

As used herein, the term "serum protein-binding moiety" shall be taken to refer to any peptide or protein having the ability to bind to a serum protein e.g., serum albumin or Fc region of an antibody or transferrin or ferritin or other serum protein having a long half life, to thereby enhance the half-life of a protein, especially a peptidyl inhibitor of the present invention. By "long half life" is meant a half life in serum approximately the same as an albumin protein e.g., human serum albumin. In this respect, it is preferred for a serum protein-binding moiety to confer on a peptidyl inhibitor of the present invention administered to a subject, including any base peptide or derivative or analog thereof, a half-life that is at least about 25% or 50% or 75% or 90% or 95% or 99% the half-life of an endogenous serum albumin protein e.g., a murine animal or primate such as a human. For example, human serum albumin has a half life in humans of 19 days e.g., Peters et al., Adv. Protein Chem. 37, 161-245 (1985), and a half-life in mice of about 35 hours e.g., Chaudhury et al., J. Exp. Med. 197, 315-322 (2003).

Peptides and proteins that comprise an amino acid sequence capable of binding to serum albumin and increase the half-life of therapeutically relevant proteins and polypeptides are known in the art. Bacterial and synthetic serum protein-binding peptides are described e.g., in International Patent Publication Nos. WO1991/01743, WO2001/45746 and WO2002/076489. International Patent Publication No. WO2004/041865 describes "nanobodies" directed against serum albumin that can be linked to a protein to increase its half-life. Chaudhury et al., The J. Exp. Med. 3, 315-322 (2003) describe the neonatal Fc receptor (FcRn) or "Brambell receptor" as an pH-dependent serum protein-binding moiety. US Pat. Publication 20070269422 (Ablynx N.V.) discloses nanobodies or domain antibodies (dAbs) of about 115 amino acids in length and comprising framework regions i.e., FR1 to FR4 and complementarity-determining regions i.e., CDR1 to CDR3, and which have serum half-life of at least about 50% the natural half-life of serum albumin in a primate.

Preferred serum protein-binding moieties comprise peptides that consist of or comprise an albumin-binding domain (ABD) or albumin-binding domain antibody (dAb) e.g., as described by Nguyen et al., Protein Eng, Design Sel. 19, 291-297 (2006); Holt et al., Protein Eng, Design Sel. 21, 283-288 (2008); Johnsson et al., Protein Eng, Design Sel. 21, 515-527 (2008), and US Pat. Publication No. 20070202045 (Genentech, Inc.), each of which is incorporated herein by reference.

Particularly preferred peptidyl serum protein-binding moieties for use in the present invention are retro-inverted peptides e.g., comprising a retroinverted analog of one or more serum protein-binding peptidyl moieties described in US Pat. Publication No. 20070202045 or US Pat. Publication 20070269422.

Non-peptidyl serum protein-binding moieties include e.g., clofibrate, clofibric acid, Tolmetin, Fenoprofen, Diflunisal, Etodolac, Naproxen, Nambutone, Ibuprofen, Chlorothiazide, Gemfibrozil, Nalidixic Acid, Methyldopate, Ampicillin, Cefamandole Nafate, N-(2-Nitrophenyl)-anthranilic Acid, N-Phenylanthranilic Acid and Quinidine Gluconate. The peptidyl inhibitors of the present invention may also be myristoylated, and/or modified by addition of a 4,4-diphenylcyclohexyl moiety e.g., Kurtzhals et al., Biochem. J. 312 (1995); Zobel et al., Bioorg. Med. Chem. Lett. 13, 1513 (2003).

Particularly preferred non-peptidyl serum protein-binding moieties for use in the present invention include 4-phenylbutanoic acid moieties having hydrophobic substituents on the phenyl ring and conjugated to an amino acid such as a D-amino acid e.g., 4-(p-iodophenyl)butyric acid conjugated to D-lysine through the ε-amino group e.g., Dumelin et al., Agnew. Chem. Int. Ed. 47, 3196-3201 (2008) incorporated herein by reference, and any one of a series of similar conjugates comprising 4-phenylbutanoic acid moieties. Free 4-(p-iodophenyl)butyric acid, or 4-(p-iodophenyl)butyric acid conjugated to D-lysine, is readily conjugated to a peptidyl inhibitor of the invention by condensation between hydrogen of an α-amino or ε-amino group on the peptidyl inhibitor and the hydroxyl group of the 4-(p-iodophenyl)butyric acid moiety.

A serum protein-binding moiety is generally covalently attached to the N-terminus or C-terminus of a peptidyl inhibitor of the present invention, and may be a chiral analog e.g., a retroinverso peptidyl moiety or PEGylated moiety. For example, a peptidyl fusion comprising a serum protein-binding moiety positioned N-terminal or C-terminal to a peptidyl inhibitor of the present invention may be produced by standard peptide synthesis means or recombinant means without the exercise of undue experimentation based on the disclosure herein. Retroinverted peptide analogs comprising a serum protein-binding moiety positioned N-terminal or C-terminal to a peptidyl inhibitor of the present invention, wherein the complete sequence is retroinverted are particularly preferred and produced without inventive effort based on the disclosure herein. Other peptidomimetic strategies include e.g., peptoids, N-methylated peptides etc., which are also encompassed by the present invention. Peptidyl fusions comprising a serum protein-binding moiety and a peptidyl inhibitor of the present invention may comprise a spacer or linker moiety separating serum protein-binding moiety and peptidyl inhibitor. Alternatively, the serum protein-binding moiety and peptidyl inhibitor may be adjacent or juxtaposed in the peptidyl fusion. Such configurations are readily modified by the inclusion of a protein transduction domain as described herein.

Spacers and Linkers

Each of the components of a peptidyl inhibitor described herein, including a base peptide or derivative or analog and any protein transduction domain, PEG moiety, serum protein-binding moiety according to any example hereof, may optionally be separated by a spacer or linker moiety. The spacer or linker moiety facilitates the independent folding of each of peptidyl inhibitor component, and/or provides for an appropriate steric spacing between plural peptide components and between peptidyl and non-peptidyl components. A suitable linker will be apparent to the skilled artisan. For example, it is often unfavorable to have a linker sequence with high propensity to adopt α-helix or β-strand structures, which could limit the flexibility of the protein and consequently its functional activity. Rather, a more desirable linker is a sequence with a preference to adopt extended conformation. In practice, most currently designed linker sequences have a high content of glycine residues that force the linker to adopt loop conformation. Glycine is generally used in designed linkers because the absence of a β-carbon permits the polypeptide backbone to access dihedral angles that are energetically forbidden for other amino acids.

Preferably, the linker is hydrophilic, i.e. the residues in the linker are hydrophilic.

In another example, a linker is a glycine residue or polyglycine moiety or polyserin moiety. Linkers comprising glycine and/or serine have a high freedom degree for linking of two proteins, i.e., they enable the fused proteins to fold and produce functional proteins. Robinson and Sauer *Proc. Natl. Acad. Sci.* 95: 5929-5934, 1998 found that it is the composition of a linker peptide that is important for stability and folding of a fusion protein rather than a specific sequence.

In one example, linkers join identical peptide target binding moieties to form homodimers. In another example, linkers join different peptide target binding moieties to form heterodimers. In another example, the linker separates a peptidyl inhibitor of the invention from a protein transduction domain. In another example, the linker separates a peptidyl inhibitor of the invention from a PEG moiety. In another example, the linker separates a peptidyl inhibitor of the invention from a HES moiety. In another example, the linker separates a peptidyl inhibitor of the invention from a polyglycine moiety. In another example, the linker separates a peptidyl inhibitor of the invention from a serum protein moiety. In another example, the linker separates a peptidyl inhibitor of the invention from a serum protein-binding moiety. In another example, the linker separates a protein transduction domain from a PEG moiety, HED moiety, polyglycine moiety, serum protein moiety or serum protein-binding moiety.

Peptidyl linkers may also be derivatized or analogs prepared there from according to standard procedures described herein.

Base Peptides

In one example, a base peptide comprises an amino acid sequence set forth in any one of SEQ ID NOs: 1 to 18 or 44.

Peptide Derivatives

The present invention also encompasses a derivative of a peptide inhibitor of CD40 and/or CD40L signaling.

As used herein the term "derivative" shall be taken to mean a peptide that is derived from an inhibitory peptide of the invention as described herein e.g., a fragment or processed form of the peptide, wherein the active portion of the base peptide is not modified e.g., a functional fragment.

As used herein the term "functional fragment" shall be taken to mean a fragment of a peptide or analog thereof that is capable of binding to CD40L and/or reducing or preventing CD40L binding to CD40 and/or reducing or preventing CD40-mediated signaling and/or CD40L-mediated signaling. In this respect, the activity of a functional fragment need not equivalent to the based peptide (or an analog) from which it is derived. For example, the fragment may have slightly enhanced or reduced activity compared to the peptide or analog from which it is derived by virtue of the removal of flanking sequence.

The term "derivative" also encompasses fusion proteins comprising a peptide of the invention. For example, the fusion protein comprises a label, such as, for example, an epitope, e.g., a FLAG epitope or a V5 epitope or an HA epitope. For example, the epitope is a FLAG epitope. Such a tag is useful for, for example, purifying the fusion protein. Alternatively, or in addition, a derivative in this context may comprise a peptidyl protein transduction domain and/or serum protein-binding peptide or domain.

The term "derivative" also encompasses a derivatized peptide, such as, for example, a peptide modified to contain one or more-chemical moieties other than an amino acid. The chemical moiety may be linked covalently to the peptide e.g., via an amino terminal amino acid residue, a carboxyl terminal amino acid residue, or at an internal amino acid residue. Such modifications include the addition of a protective or capping group on a reactive moiety in the peptide, addition of a detectable label, and other changes that do not adversely destroy the activity of the peptide compound. For example, a derivative may comprise a PEG moiety, radionuclide, colored latex, etc.

A derivative generally possesses or exhibits an improved characteristic relative to a e.g., enhanced protease resistance and/or longer half-life and/or enhanced transportability between cells or tissues of the human or animal body and/or reduced adverse effect(s) and/or enhanced affinity for CD40L and/or enhanced CD40L-signaling inhibitory activity and/or enhanced CD40-signaling inhibitory activity.

The following examples of peptide derivatives may be employed separately or in combination using standard procedures known to the skilled artisan.

In one example, a peptide derivative comprises a polyethylene glycol (PEG) moiety e.g., having a molecular mass of about 5 kDa or about 12 kDa or about 20 kDa or about 30 kDa or about 40 kDa. The PEG moiety may comprise a branched or unbranched molecule. A PEG moiety may be added to the N-terminus and/or to the C-terminus of a peptidyl inhibitor of the invention, including a peptide, derivative or analog thereof as described according to any example herein. A PEG moiety may enhance serum half-life of the peptidyl inhibitor e.g., by protecting the peptide from degradation. A PEG moiety may be separated from the N-terminus and/or C-terminus of the peptidyl inhibitor by a spacer e.g., comprising up to 6 or 7 or 8 or 9 or 10 carbon atoms such as an 8-amino-3,6-dioxaoctanoyl spacer. For example, a spacer may reduce steric hindrance of the inhibition of CD40 or CD40L signaling or reduce steric hindrance of inhibition of the CD40-CD40L interaction. Maleimide chemistry may be employed to conjugate a PEG moiety to the peptide e.g., via cysteine residues located either within or at the N-terminal end of the peptide. For peptides that are refractory to conjugation in this manner e.g., by virtue of intramolecular disulfide bridge formation, a variety of other chemistries known to the skilled artisan may be employed to ligate PEG moieties onto the N-terminal and/or C-terminal ends of the peptides.

In another example, a peptide derivative comprises a hydroxyethyl starch (HES) moiety i.e., the peptidyl inhibitor is "HESylated". The HES moiety may comprise a branched or unbranched molecule. A HES moiety may be added to the N-terminus and/or to the C-terminus of a peptidyl inhibitor of the invention, including a peptide, derivative or analog thereof as described according to any example herein. A HES moiety may enhance serum half-life of the peptidyl inhibitor e.g., by protecting the peptide from degradation. A HES moiety may be separated from the N-terminus and/or C-terminus of the peptidyl inhibitor by a spacer e.g., comprising up to 6 or 7 or 8 or 9 or 10 carbon atoms such as an 8-amino-3,6-dioxaoctanoyl spacer. For example, a spacer may reduce steric hindrance of the inhibition of CD40 or CD40L signaling or reduce steric hindrance of inhibition of the CD40-CD40L interaction. Maleimide chemistry may be employed to conjugate a HES moiety to the peptide e.g., via cysteine residues located either within or at the N-terminal end of the peptide. For peptides that are refractory to conjugation in this manner e.g., by virtue of intramolecular disulfide bridge formation, a variety of other chemistries known to the skilled artisan may be employed to ligate HES moieties onto the N-terminal and/or C-terminal ends of the peptides.

In another example, a peptide derivative comprises a polyglycine moiety e.g., comprising two or three or four or five or six or seven or eight or nine or ten glycine residues covalently linked. A polyglycine moiety may be added to the N-terminus and/or to the C-terminus of a peptidyl inhibitor of the invention, including a peptide, derivative or analog thereof as described according to any example herein, to produce a "polyglycinated" peptide. A polyglycine moiety may enhance serum half-life of the peptidyl inhibitor e.g., by protecting the peptide from degradation. A polyglycine moiety may be further separated from the N-terminus and/or C-terminus of the peptidyl inhibitor by a spacer e.g., comprising up to 6 or 7 or 8 or 9 or 10 carbon atoms such as an 8-amino-3,6-dioxaoctanoyl spacer. Standard recombinant means, oxime chemistry or peptide synthetic means are employed to add a polyglycine moiety to a peptidyl inhibitor of the present invention. A polyglycine moiety may also be used in conjunction with another moiety to extend the half-life of a peptidyl inhibitor of the present invention as described according to any example hereof, wherein the polyglycine moiety itself may serve further as a spacer between the peptidyl inhibitor and the other moiety.

In another example, a peptide derivative comprises a serum protein moiety or serum protein-binding moiety as described according to any example hereof, which may be added to the N-terminus and/or to the C-terminus of a peptidyl inhibitor of the invention, including a peptide, derivative or analog thereof as described according to any example herein. A serum protein moiety or serum protein-binding moiety may enhance serum half-life of the peptidyl inhibitor or translocation of the peptide in serum. A serum protein moiety or serum protein-binding moiety may be separated from the N-terminus and/or C-terminus of the peptidyl inhibitor by a spacer e.g., comprising up to 6 or 7 or 8 or 9 or 10 carbon atoms such as an 8-amino-3,6-dioxaoctanoyl spacer. For example, a spacer may reduce steric hindrance of the inhibition of CD40 or CD40L signaling or reduce steric hindrance of inhibition of the CD40-CD40L interaction.

In another example, a peptide derivative comprises a moiety e.g., a peptide, capable of inhibiting binding to Fc and/or otherwise reducing adverse consequences of activating CD40. Such a moiety may be added to the N-terminus and/or to the C-terminus of a peptidyl inhibitor of the invention, including a peptide, derivative or analog thereof as described according to any example herein. Such a moiety may be separated from the N-terminus and/or C-terminus of the peptidyl inhibitor by a spacer e.g., comprising up to 6 or 7 or 8 or 9 or 10 carbon atoms such as an 8-amino-3,6-dioxaoctanoyl spacer. For example, a spacer may reduce steric hindrance of the inhibition of CD40 or CD40L signaling or reduce steric hindrance of inhibition of the CD40-CD40L interaction.

In another example, the peptide derivative comprises an N-terminal and/or C-terminal cysteine residue e.g., to facilitate intramolecular cross-linking or intermolecular cross-linking with another peptide such as the same or a different peptidyl inhibitor e.g., to form a multimeric peptide, or to facilitate intermolecular cross-linking with a different moiety e.g., phage p3 protein, phage p8 protein, serum protein moiety or serum protein-binding moiety. In another example, the peptide derivative comprises an N-terminal cysteine residue. In another example, the peptide derivative comprises a C-terminal cysteine residue. In another example, the peptide derivative does not comprise both an N-terminal and a C-terminal cysteine residue e.g., because the peptide autonomously forms a stable conformation thereby avoiding the need for cyclization mediated via disulfide bond/bridge formation between N-terminal and C-terminal cysteine residues. In another example, the peptide derivative is not capable of forming or does not form intramolecular disulfide bonds/bridges or cross-links e.g., because the peptide autonomously forms a stable conformation not requiring intramolecular disulfide constraint.

In another example, the peptide derivative comprises a plurality of peptides of the present invention. Such "chain-extended" variants may bind to CD40L with higher affinity than the monomeric base peptide e.g., by virtue of the larger ligand binding to CD40L over a larger surface area but within the same proximity as the monomeric base peptide. Such chain extended variants may also exhibit increased affinity for CD40L over their monomeric constituent sequences by virtue of increasing local inhibitor concentration and/or by concurrent binding to adjacent CD40L subunits or adjacent sites on the same subunit, thereby benefiting from an avidity effect.

Methods for producing multimeric proteins include conventional peptide synthesis and recombinant expression means.

In one preferred example, the ligand-binding interface with CD40L is extended by directed evolution to achieve multimerization. In this example, a second peptidyl inhibitor is positioned downstream of a first peptidyl inhibitor, wherein said positioning is adjacent or spaced apart e.g., by one or more amino acids or other linker/spacer molecule as described herein.

Alternatively, multimeric proteins are produced by expression in a single phagemid vector having one or more recombination sites for a site-specific recombinase e.g., one or more attachment sites selected from the group consisting of lox, RS, gix, frt, attB, attP, attL and attR. The phagemid vector may be a modified form of any phagemid vector suitable for phage display methodology, the only requirement being the addition of one or more attachment sites for a site-specific recombinase. For example, the filamentous phage may be a single stranded DNA bacteriophage vector, a modified phagemid pIII (syn. P3) or PVIII (syn. P8) display vector comprising one or more attachment sites for a site-specific recombinase, a modified phagemid gIII display vector comprising one or more attachment sites for a site-specific recombinase, a modified pJUFO vector comprising one or more attachment sites for a site-specific recombinase, or a modified pLUCK vector comprising one or more attachment sites for a site-specific recombinase. A preferred form of a suitable phagemid vector for expressing multimeric peptide comprises:
(i) one or more recombination sites for a site-specific recombinase positioned so as to provide for recombination between said vector and a nucleic acid molecule encoding one or more amino acid sequences to be expressed from said vector wherein said recombination provides for expression of a fusion protein between said one or more amino acid sequences and a filamentous phage protein e.g., p3 or p8;
(ii) a promoter e.g., a lambda PL promoter, positioned so as to be capable of regulating transcription of nucleic acid encoding the fusion protein at (i);
(iii) at least one sequence capable of terminating transcription of nucleic acid encoding the fusion protein at (i);
(iv) a replication origin derived from a filamentous phage;
(v) a plasmid replication origin; and
(vi) at least one selection marker.

In one example, the phagemid vector comprises two recombination sites for a site-specific recombinase wherein each of said recombination sites is positioned so as to provide for recombination between said vector and a nucleic acid molecule encoding one or more amino acid sequences to be expressed from said vector wherein said recombination provides for expression of a fusion protein between said one or more amino acid sequences and a filamentous phage protein e.g., p3 or p8.

Isolated nucleic acid encoding one or more amino acid sequences for multimerization are sub-clones into the phagemid vector, wherein said nucleic acid comprises one or more recombination sites for a site-specific recombinase compatible with one or more recombination sites for the same site-specific recombinase on the phagemid vector. For example, the isolated nucleic acid may encode one or more amino acid sequences wherein each of said amino acid sequences is capable of forming secondary structures and/or super-secondary structures, e.g., a peptidyl inhibitor of the invention, or secondary structure as shown in Table 1 hereof, a fold, or an assembly of secondary structures. Exemplary nucleic acids encode peptide inhibitors of one or more protein-protein interaction(s) and/or one or more biological phenotypes attributable to said protein-protein interaction(s) e.g., nucleic acid encoding one or more CD40L peptide inhibitors of the present invention as described according to any example hereof. Wherein the isolated nucleic acid encodes a single amino acid sequence, the recombination site(s) will generally be positioned at one end or so as to flank the sequence encoding the amino acid sequence being introduced to the vector. Wherein the isolated nucleic acid encodes a plurality of amino acid sequences to be expressed by phage display, the recombination sites will generally be positioned at one end or so as to flank each nucleotide sequence encoding an amino acid sequence being introduced to the vector, or alternatively, flanking the nucleic acid encoding all of the amino acid sequences being introduced to the vector.

The isolated nucleic acid introduced to the vector may comprise a spacer nucleotide sequence, e.g., encoding an amino acid spacer such as a GS linker, to provide for spatial separation between amino acid sequences of interest in the expressed multimeric protein and/or to provide for spatial separation between the nucleotide sequence encoding amino acid sequences of interest and recombination sites e.g., to prevent spurious recombination of functionally-important coding sequence.

In a further example, a plurality of peptides is expressed in a single phagemid vector, by a method comprising:
(i) providing a phagemid vector having one or more recombination sites for a site-specific recombinase said sites being positioned so as to provide for recombination between said vector and a nucleic acid molecule encoding one or more amino acid sequences to be expressed from said vector;
(ii) providing isolated nucleic acid encoding one or more amino acid sequences and wherein said nucleic acid comprises one or more recombination sites for a site-specific recombinase compatible with one or more recombination sites for the same site-specific recombinase on the phagemid vector to which said nucleic acid is to be introduced;
(iii) causing recombination to occur between said one or more recombination sites for a site-specific recombinase at (i) and said one or more recombination sites for a site-specific recombinase at (ii) to thereby produce a phagemid vector capable of expressing of a fusion protein between said one or more amino acid sequences at (ii) and a filamentous phage protein e.g., p3 or p8;
(iv) providing the phagemid vector produced at (iii) and isolated nucleic acid encoding one or more amino acid sequences, wherein said isolated nucleic acid comprises one or more recombination sites for a site-specific recombinase compatible with one or more recombination sites for the same site-specific recombinase on the phagemid vector produced at (iii); and
(v) causing recombination to occur between recombination sites for a site-specific recombinase at (iv) to thereby produce a phagemid vector capable of expressing of a fusion protein between a plurality of amino acid sequences and a filamentous phage protein e.g., p3 or p8.

An integrase e.g., a tyrosine integrase, or serine recombinase may be employed to facilitate recombination events, the only requirements being compatibility of the site-specific recombination sites between the phagemid vector and nucleic acid to be introduced, and the enzyme(s) or enzyme complex(es) used to promote excision and ligation events. Such compatible recombinase systems are known to those skilled in the art when provided with suitable site-specific recombination systems, or described herein, including Sin resolvase, ΦRv1 integrase, lambda integrase, Cre recombinase, R recombinase, Gin recombinase and FLP recombinase, amongst others.

Two or three or four or five or six or more peptides may be recombined into the same fusion protein for expression with a filamentous phage protein. A limitation to the number of monomers that are introduced into the phage vector may be provided by stability considerations from highly repetitive sequences in the case of homomeric proteins, and the number of units provided in the isolated nucleic acid being introduced.

Another example of the present invention provides an isolated phagemid vector having one or more recombination sites for a site-specific recombinase said sites being positioned so as to provide for recombination between said vector and a nucleic acid molecule encoding one or more amino acid sequences to be expressed from said vector. In one example, the isolated phagemid vector comprises one or more recombination sites for a site-specific recombinase positioned so as to provide for recombination between said vector and a nucleic acid molecule encoding one or more amino acid sequences to be expressed from said vector wherein said recombination provides for expression of a fusion protein between said one or more amino acid sequences and a filamentous phage protein e.g., p3 or p8. In another example, the isolated phagemid vector comprises:

(i) one or more recombination sites for a site-specific recombinase positioned so as to provide for recombination between said vector and a nucleic acid molecule encoding one or more amino acid sequences to be expressed from said vector wherein said recombination provides for expression of a fusion protein between said one or more amino acid sequences and a filamentous phage protein e.g., p3 or p8;
(ii) a promoter e.g., a lambda PL promoter, positioned so as to be capable of regulating transcription of nucleic acid encoding the fusion protein at (i);
(iii) at least one sequence capable of terminating transcription of nucleic acid encoding the fusion protein at (i);
(iv) a replication origin derived from a filamentous phage;
(v) a plasmid replication origin; and
(vi) at least one selection marker.

The phagemid vector may comprise one or more recombination sites for a site-specific recombinase wherein a recombination site is selected from the group consisting of lox, RS, gix, frt, attB, attP, attL and attR.

In one example, the phagemid vector is a single stranded DNA bacteriophage vector. In another example, the phagemid vector is a modified phagemid p3 or p8 display vector comprising one or more attachment sites for a site-specific recombinase. In a further example, the phagemid vector is a modified phagemid gIII display vector comprising one or more attachment sites for a site-specific recombinase. In a further example, the phagemid vector is a modified pJUFO vector comprising one or more attachment sites for a site-specific recombinase. In another example, the phagemid vector is a modified pLUCK vector comprising one or more attachment sites for a site-specific recombinase.

In a further example, the present invention provides for the use of a phagemid vector of the present invention in the expression of a synthetic multimeric protein by phage display. In one example, a combinatorial protein will comprise a plurality of peptide monomers each monomer having the same binding affinity and/or substrate specificity and/or or functionality. The peptide monomers may be closely-related by sequence or divergent e.g., variants of the same base peptide sequence or derived from different peptides. In another example, a combinatorial protein will comprise a plurality of peptide monomers each monomer having a different binding affinity and/or substrate specificity and/or or functionality e.g., wherein the peptide monomers are divergent at the sequence level and/or derived from different peptides.

It will be apparent to the skilled artisan that means for derivation of a peptide apply equally to any peptidyl inhibitor of the invention, an analog thereof, and any additional peptidyl components of a fusion peptide e.g., a protein transduction domain and/or peptidyl linker or spacer and/or serum protein moiety and/or serum protein-binding moiety to which the peptidyl inhibitor(s) and/or analog(s) is/are attached.

Peptide Analogs

In another example of the invention, a CD40 and/or CD40L signaling inhibitor is a peptide analog.

As used herein, the term "analog" shall be taken to mean a peptide wherein the active portion is modified e.g., to comprise one or more naturally-occurring and/or non-naturally- occurring amino acids, provided that the peptide analog is capable of inhibiting or reducing CD40 and/or CD40L signaling. For example, the term "analog" encompasses an inhibitory peptide comprising one or more conservative amino acid changes. In another example, an "analog" comprises one or more D-amino acids.

An analog generally possesses or exhibits an improved characteristic relative to a base peptide from which it is derived e.g., enhanced protease resistance and/or longer half-life and/or enhanced transportability between cells or tissues of the human or animal body and/or reduced adverse effect(s) and/or enhanced affinity for CD40L and/or enhanced CD40L-signaling inhibitory activity and/or enhanced CD40-signaling inhibitory activity.

Suitable peptide analogs include, for example, a peptide comprising one or more conservative amino acid substitutions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

It also is contemplated that other sterically similar compounds may be formulated to mimic the key portions of the peptide structure. Such compounds, which may be termed peptidomimetics, may be used in the same manner as a CD40 and/or CD40L signaling peptide inhibitor or derivative thereof. The generation of such an analog may be achieved by the techniques of modeling and chemical design known to those of skill in the art. It will be understood that all such sterically similar peptide analogs fall within the scope of the present invention.

An example of an analog of a peptide of the invention comprises one or more non-naturally occurring amino acids or amino acid analogs. For example, a peptide inhibitor as described herein comprises one or more naturally occurring non-genetically encoded L-amino acids, synthetic L-amino acids or D-enantiomers of an amino acid. For example, the peptide comprises only D-amino acids. For example, the analog comprises one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenylalanine, 2-fluorophenylalanine, 3-fluorophenylalanine, 4-fluorophenylalanine, penicillamine, 1,2,3,4-tetrahydro-tic isoquinoline-3-carboxylic acid β-2-thienylalanine, methionine sulfoxide, homoarginine, N-acetyl lysine, 2,4-diamino butyric acid, ρ-aminophenylalanine, N-methylvaline, homocysteine, homoserine, ϵ-amino hexanoic acid, δ-amino valeric acid, 2,3-diaminobutyric acid and mixtures thereof.

Other amino acid residues that are useful for making the peptides and peptide analogs described herein can be found, e.g., in Fasman, 1989, CRC Practical Handbook of Biochemistry and Molecular Biology, CRC Press, Inc., and the references cited therein.

The present invention additionally encompasses an isostere of a peptide described herein. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets.

Other modifications include, for example, an N-alkyl (or aryl) substitution (ψ [CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In another example, a peptide analog is a retro-peptide analog (see, for example, Goodman et al., *Accounts of Chemical Research*, 12:1-7, 1979). A retro-peptide analog comprises a reversed amino acid sequence of a peptide inhibitor described herein. For example, a retro-peptide analog of a peptide inhibitor comprises a reversed amino acid sequence of a sequence set forth in any one of SEQ ID NOs: 35 to 43 or a reversed sequence of any one of SEQ ID NOs: 1 to 34 or 44. Optionally, the peptide analog comprises an additional feature, such as, for example, a protein transduction domain and/or serum protein moiety and/or serum protein-binding moiety, each of which may also be a retro-peptide analog. The retro-peptide analog according to any example hereof may be PEGylated.

In a further example, an analog of a peptide described herein is a retro-inverso peptide (as described, for example, in Sela and Zisman, *FASEB J.* 11:449, 1997). Evolution has ensured the almost exclusive occurrence of L-amino acids in naturally occurring proteins. As a consequence, virtually all proteases cleave peptide bonds between adjacent L-amino acids. Accordingly, artificial proteins or peptides composed of D-amino acids are preferably resistant to proteolytic breakdown. Retro-inverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids, e.g., Jameson et al., *Nature*, 368, 744-746 (1994); Brady et al., *Nature*, 368, 692-693 (1994). The net result of combining D-enantiomers and reverse synthesis is that the positions of carbonyl and amino groups in each amide bond are exchanged, while the position of the side-chain groups at each alpha carbon is preserved. An advantage of retro-inverso peptides is their enhanced activity in vivo due to improved resistance to proteolytic degradation, i.e., the peptide has enhanced stability. (e.g., Chorev et al., *Trends Biotech.* 13, 438-445, 1995).

Retro-inverso peptide analogs may be complete or partial. Complete retro-inverso peptides are those in which a complete sequence of a peptide descried herein is reversed and the chirality of each amino acid in a sequence is inverted, other than glycine, because glycine does not have a chiral analog. Partial retro-inverso peptide analogs are those in which only some of the peptide bonds are reversed and the chirality of only those amino acid residues in the reversed portion is inverted. For example, one or two or three or four or five or six or seven or eight or nine or ten or eleven or twelve or thirteen or fourteen or fifteen or sixteen or seventeen or eighteen or nineteen or twenty or twenty one or twenty two or twenty three or twenty four or twenty five or twenty six or twenty seven or twenty eight or twenty nine or thirty or thirty one or thirty two or thirty three or thirty four or thirty five or thirty six or thirty seven or thirty eight amino acid residues are D-amino acids. The present invention clearly encompasses both partial and complete retro-inverso peptide analogs.

In this respect, such a retroinverso peptide analog may optionally include an additional component, such as, for example, a protein transduction domain, which may also be retroinverted.

For example, a retro-inverso peptide analog comprises an amino acid sequence set forth in any one of SEQ ID NOs: 35 to 43, or a retro-inverso peptide analog of any one of SEQ ID NOs: 1 to 34 or 44. Optionally, a retro-inverso peptide analog comprises an additional feature, such as, for example, a protein transduction domain and/or serum protein moiety and/or serum protein-binding moiety, each of which may also be a retro-peptide analog. The retro-inverso peptide analog according to any example hereof may also be PEGylated, HESylated or polyglycinated.

In yet another example, a base peptide is mutated to thereby improve the bioactivity of the peptide, e.g., the affinity with which the peptide binds to a target molecule and/or the specificity with which a peptide binds to a target molecule. Methods for mutating a peptide will be apparent to the skilled artisan and/or are described herein an include e.g., affinity maturation. For example, diverse amino acid sequences may be derived from a base peptide and peptides produced, by synthetic or recombinant means.

For affinity maturation employing synthetic means, the amino acid sequences of a peptide inhibitor is modified in silico e.g., so as to retain secondary structure characteristics of the base peptide, a data set of related sequences is produced, and the peptides are synthesized and screened for activity.

For affinity maturation employing recombinant means, it is necessary to mutate nucleic acids encoding a diverse set of amino acid sequences by site-directed or random mutagenesis approaches. For example, nucleic acid may be amplified using mutagenic PCR such as by (i) performing the PCR reaction in the presence of manganese; and/or (ii) performing the PCR in the presence of a concentration of dNTPs sufficient to result in misincorporation of nucleotides. Methods of inducing random mutations using PCR are known in the art and are described, for example, in Dieffenbach (ed) and Dveksler (ed) (In: PCR Primer: A Laboratory Manual, Cold Spring Harbour Laboratories, NY, 1995). Furthermore, commercially available kits for use in mutagenic PCR are obtainable, such as, for example, the Diversify PCR Random Mutagenesis Kit (Clontech) or the GeneMorph Random Mutagenesis Kit (Stratagene). For example, a PCR reaction is performed in the presence of at least about 200 μM manganese or a salt thereof, more preferably at least about 300 μM manganese or a salt thereof, or even more preferably at least about 500 μM or at least about 600 μM manganese or a salt thereof. Such concentrations manganese ion or a manganese salt induce from about 2 mutations per 1000 base pairs (bp) to about 10 mutations every 1000 bp of amplified nucleic acid (Leung et al *Technique* 1, 11-15, 1989).

Alternatively, nucleic acid is mutated by inserting said nucleic acid into a host cell that is capable of mutating nucleic acid. Such host cells are deficient in one or more enzymes, such as, for example, one or more recombination or DNA repair enzymes, thereby enhancing the rate of mutation to a rate that is rate approximately 5,000 to 10,000 times higher than for non-mutant cells. Strains particularly useful for the mutation of nucleic acids carry alleles that modify or inactivate components of the mismatch repair pathway. Examples of such alleles include alleles selected from the group consisting of mutY, mutM, mutD, mutT, mutA, mutC and mutS. Bacterial cells that carry alleles that modify or inactivate components of the mismatch repair pathway are known in the art, such as, for example the XL-1Red, XL-mutS and XL-mutS-Kan$^r$ bacterial cells (Stratagene).

It will also be apparent to the skilled artisan that unitary analogs may be produced from any peptidyl inhibitor of the invention, with or without any other peptidyl moieties covalently attached to the inhibitor e.g., as an analog of a fusion peptide comprising e.g., one or more peptidyl inhibitors and an element selected from a protein transduction domain and/or peptidyl linker or spacer and/or serum protein moiety and/or serum protein-binding peptide moiety to which the peptidyl inhibitor(s) is/are attached. Such unitary analogs may be derivatized as described herein.

2. Non-Peptidyl Inhibitors of CD40 and/or CD40L Signaling

A non-peptidyl inhibitor described herein may be a nucleic acid or small molecule or a derivative or analog thereof according to any example hereof, that functions as a CD40 signaling inhibitor and/or a CD40L signaling inhibitor. Preferred non-peptidyl inhibitors of the present invention are functional equivalents of a peptidyl inhibitor of the present invention, however they preferably possess enhanced inhibitory activity or affinity for CD40L, or enhanced pharmaceutical properties e.g., longer half-life, enhanced uptake and/or transportability between cells or tissues of the animal body and/or suitability for a particular mode of administration e.g., injectability, inhalability or modified solubility characteristic. Antibody inhibitors are less preferred.

As with peptidyl inhibitors, a non-peptidyl inhibitor of the present invention will reduce or prevent CD40L-binding activity and/or CD40L-signaling inhibitory activity and/or CD40-signaling inhibitory activity e.g., by virtue or preventing an interaction between CD40L and CD40 that activates the CD40:CD40L costimulatory pathway.

The term "derivative" or "analog" in the context of a non-peptidyl inhibitor refers broadly to a non-peptidyl composition in a modified form compared to the inhibitory molecule from which it is derived and retains inhibitory activity or possesses enhanced inhibitory activity with respect to CD40L-binding and/or CD40L-signaling and/or CD40-signaling e.g., by virtue or preventing an interaction between CD40L and CD40 that activates the CD40:CD40L costimulatory pathway. A derivative or analog need not possess equivalent inhibitory activity compared to the molecule (or peptide) from which it is derived.

In one example of the invention, a non-peptidyl inhibitor of CD40 and/or CD40L signaling comprises nucleic acid that reduces or prevents the interaction between CD40 and CD40L e.g., by binding to CD40L at or near the interaction interface or other site required for CD40 and/or CD40L signaling.

In one example, a CD40L-signaling inhibitor or CD40-signaling inhibitor is a small molecule. The present invention thus includes a small molecule inhibitor and/or uses thereof for the treatment and/or prophylaxis of one or more conditions associated with aberrant CD40L-signaling or aberrant CD40-signaling and complications thereof. For example, a small molecule inhibitor is used in the preparation of a medicament for the treatment or prophylaxis of one or more conditions associated with aberrant CD40L-signaling or aberrant CD40-signaling and/or complications thereof.

A suitable small molecule inhibitor is identified from a library of small molecules. Techniques for synthesizing small organic compounds will vary considerably depending upon the compound, however such methods will be well known to those skilled in the art. In one embodiment, informatics is used to select suitable chemical building blocks from known compounds, for producing a combinatorial library. For example, QSAR (Quantitative Structure Activity Relationship) modeling approach uses linear regressions or regression trees of compound structures to determine suitability. The software of the Chemical Computing Group, Inc. (Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and logP (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens, can be used to expand the list of compounds being screened to thereby identify highly active compounds.

Assays to Identify and Isolate Therapeutic and Prophylactic Compounds

Any assay described herein for identifying binding activity to CD40L and/or an interaction between CD40L and CD40 and/or a functionality of CD40L signaling such as CD40L-induced expression of CD86 and/or CD40L-mediated T cell proliferation and/or CD40L-dependent and CD40-mediated signaling, may be employed to identify a peptidyl or non-peptidyl inhibitor of the present invention. Alternatively, or in addition, one or more accepted animal models of CD40L-dependent signaling (i.e., CD40-mediated event and/or CD40L-dependent CD40-mediated event) may be employed e.g., a murine model of acute airways inflammation, a primate model of allograft rejection, a murine model of diabetes, a murine model of atherosclerosis, a murine model of angiogenesis, a murine EAE model of multiple sclerosis, a rodent model of graft-versus-host-disease, a rodent model of mercuric chloride-induced glomerulonephritis, and a rodent model of inflammatory bowel disease, each of which is known to the skilled artisan. For example, screens for inhibition of CD40L are described herein which can distinguish between peptide inhibitors with distinct modes of action. In one example, competitive inhibitors of the interaction between CD40L and its cognate receptor CD40 are identified. In another example, allosteric inhibitors which alter the conformation of CD40L upon binding, thereby blocking its activity, are identified.

For example, a compound library or mixture may be screened e.g., to isolate a compound that antagonizes the interaction between CD40L and CD40 and/or antagonizes CD40L signaling or CD40 signaling or CD40L-induced expression of CD86 or inhibits CD40L-mediated T cell proliferation. This may require repeated screening of pools of compounds in vitro or in vivo to eventually purify the compound free or substantially free of contaminants.

Alternatively, a previously-isolated compound not known to have the ability to antagonize the interaction between CD40L and CD40 and/or antagonize CD40L signaling or CD40 signaling or CD40L-induced expression of CD86 or to inhibit CD40L-mediated T cell proliferation, is screened by one or more of the foregoing assays to determine whether or not it has the required property.

It is to be understood that the foregoing assays can be utilized in separately or collectively and in any order determined empirically to identify or isolate the desired product at a level of purity and having a suitable activity ascribed to it e.g., for therapy. The activity and purity of the compounds determined by these assays make the compound suitable of formulations e.g., injectable and/or inhalable medicaments and/or oral formulations for treatment and/or prophylaxis.

The present invention encompasses the use of any in silico or in vitro analytical method and/or industrial process for carrying the screening methods described herein into a pilot scale production or industrial scale production of a compound identified in such screens. This invention also provides information for such production method(s). Accordingly, the present invention also provides a process for identifying or determining a compound supra, said method comprising:
(i) performing a method as described herein according to any embodiment to thereby identify a compound;
(ii) optionally, determining the amount of the compound;
(iii) optionally, determining the structure of the compound; and
(iv) providing the compound or the name or structure of the compound such as, for example, in a paper form, machine-readable form, or computer-readable form.

As used herein, the term "providing the compound" shall be taken to include any chemical or recombinant synthetic means for producing said compound (with or without derivitization) or alternatively, the provision of a compound that has been previously synthesized by any person or means.

In one example, the compound or the name or structure of the compound is provided with an indication as to its use e.g., as determined by a screen described herein.

The present invention additionally provides a process for identifying or determining a compound or modulator supra, said method comprising:
(i) performing a method as described herein according to any embodiment to thereby identify or determine a compound;
(ii) optionally, determining the amount of the compound;
(iii) optionally, determining the structure of the compound;
(iv) optionally, providing the name or structure of the compound such as, for example, in a paper form, machine-readable form, or computer-readable form; and
(v) providing the compound.

In the case of a peptide, the method optionally further comprises providing a chemical derivative of the peptide by protection of the amino- or carboxyl-terminus, cyclization of the peptide or construction of the peptide as a retroinverso peptide. The method also optionally involves identifying and/or validating one or more peptidyl compounds such as by displaying a peptide in vitro or on a bacteriophage particle, e.g., using lytic T7-based or non-lytic M13-based phage display, identifying the sequence of the peptide, making the compound by recombinant means or peptide chemistry, and testing the ability of the peptide to produce a desired effect such as reduced or prevented neutrophilic inflammation or inhibition of a specific protein interaction involved in a neutrophilic inflammatory response. Preferably, the peptide is displayed within a protein-based scaffold e.g., a scaffold structure derived from lipocalin, ankyrin repeats, fibronectin, kunitz domains, A-domains, affibodies etc. Alternatively the inhibitory peptide can be grafted into such a protein based scaffold in order to enhance stability or improve stability.

In one example, the compound or the name or structure of the compound is provided with an indication as to its use e.g., as determined by a screen described herein.

The present invention also provides a method of manufacturing a compound identified by a screening method described herein according to any embodiment for use in medicine comprising:
(i) performing a method as described herein according to any embodiment to thereby identify or determine a compound; and
(ii) using the compound in the manufacture of a therapeutic for use in medicine.

In one example, the method comprises the additional step of isolating the compound. Alternatively, a compound is identified and is produced for use in the manufacture of a compound for use in medicine.

Formulations

The present invention provides for the use of an inhibitor of the present invention as described according to any example hereof in the preparation of a medicament for treatment of a subject in need thereof e.g., for attenuation or alleviation or amelioration of an inappropriate or adverse humoral immune response, such as an immune response associated with or causative of an autoimmune disease. Alternatively, or in addition, the invention provides for use of an inhibitor of the present invention as described according to any example hereof in the preparation of a medicament for treatment for preventing or reducing an immune response against an antigen having a therapeutic or adaptive benefit to a subject. Alternatively, or in addition, the invention provides for use of an inhibitor of the present invention as described according to any example hereof in the preparation of a medicament for preventing or reducing a counter-adaptive immune response in a subject.

A compound of the invention as described herein according to any embodiment is formulated for therapy or prophylaxis with a carrier or excipient e.g., suitable for inhalation or injection.

The term "carrier or excipient" as used herein, refers to a carrier or excipient that is conventionally used in the art to facilitate the storage, administration, and/or the biological activity of an active compound. A carrier may also reduce any undesirable side effects of the active compound. A suitable carrier is, for example, stable, e.g., incapable of reacting with other ingredients in the formulation. In one example, the carrier does not produce significant local or systemic adverse effect in recipients at the dosages and concentrations employed for treatment. Such carriers and excipients are generally known in the art. Suitable carriers for this invention include those conventionally used, e.g., water, saline, aqueous dextrose, dimethyl sulfoxide (DMSO), and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, one or more alkylsaccharides, and the like.

The skilled artisan will be aware of a suitable carrier or excipient. For example, a carrier or excipient does not inhibit the anti-inflammatory activity of a CD40L-dependent signaling inhibitor. In one example, the carrier or excipient permits the inhibitor to inhibit or reduce inflammation.

The formulations can be subjected to conventional pharmaceutical expedients, such as sterilization, and can contain a conventional pharmaceutical additive, such as a preservative and/or a stabilizing agent and/or a wetting agent and/or an emulsifying agent and/or a salt for adjusting osmotic pressure and/or a buffer and/or other additives known in the art. Other acceptable components in the composition of the invention include, but are not limited to, isotonicity-modifying agents such as water and/or saline and/or a buffer including phosphate, citrate, succinate, acetic acid, or other organic acids or their salts.

In an example, a formulation includes one or more stabilizers, reducing agents, anti-oxidants and/or anti-oxidant chelating agents. The use of buffers, stabilizers, reducing agents, anti-oxidants and chelating agents in the preparation of compositions, is known in the art and described, for example, in Wang et al. *J. Parent. Drug Assn.* 34:452-462, 1980; Wang et al. *J. Parent. Sci. Tech.* 42:S4-S26 (Supplement), 1988. Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. Suitable salts and isotonicifiers include sodium chloride, dextrose, mannitol, sucrose, trehalose, or the like. Where the carrier is a liquid, it is preferred that the carrier is hypotonic or isotonic with oral, conjunctival, or dermal fluids and has a pH within the range of 4.5-8.5. Where the carrier is in powdered form, it is preferred that the carrier is also within an acceptable non-toxic pH range.

In another example, a formulation as described herein according to any embodiment additionally comprises a compound that enhances or facilitates uptake of a compound. Suitable dermal permeation enhancers are, for example, a lipid disrupting agent (LDA), a solubility enhancer, or a surfactant.

LDAs are typically fatty acid-like molecules proposed to fluidize lipids in the human skin membrane. Suitable LDAs are described, for example, in Francoeur et al., *Pharm. Res.*, 7: 621-627, 1990 and U.S. Pat. No. 5,503,843. For example, a suitable LDA is a long hydrocarbon chain with a cis-unsaturated carbon-carbon double bond. These molecules have been shown to increase the fluidity of the lipids, thereby increasing drug transport. For example, oleic acid, oleyl alcohol, decanoic acid, and butene diol are useful LDAs.

Solubility enhancers act by increasing the maximum concentration of drug in a composition, thus creating a larger concentration gradient for diffusion. For example, a lipophilic vehicle isopropyl myristate (IPM) or an organic solvent ethanol or N-methyl pyrrolidone (NMP) or dimethyl sulfoxide (DMSO) are suitable solubility enhancers (Liu et al., *Pharm. Res.* 8: 938-944, 1991; and Yoneto et al., *J. Pharm. Sci.* 84: 853-860, 1995).

Surfactants are amphiphilic molecules capable of interacting with the polar and lipid groups in the skin. These molecules have affinity to both hydrophilic and hydrophobic groups, which facilitate in traversing complex regions of the dermis. Suitable surfactants include, for example, an anionic surfactant lauryl sulfate (SDS) or a nonionic surfactant polysorbate 80 (Tween 80). Suitable surfactants are described, for example, in Sarpotdar et al., *J. Pharm. Sci.* 75: 176-181, 1986)

In another example, the formulation is a microemulsion. Microemulsion systems are useful for enhancing transdermal delivery of a compound. Characteristics of such microemulsion systems are sub-micron droplet size, thermodynamic stability, optical transparency, and solubility of both hydrophilic and hydrophobic components. Microemulsion systems have been shown to be useful for transdermal delivery of compounds and to exhibit improved solubility of hydrophobic drugs as well as sustained release profiles (Lawrence, et. al. *Int. Journal of Pharmaceutics* 111: 63-72, 1998).

In another example, a formulation comprises a peptidyl moiety conjugated to a hydrolysable polyethylene glycol (PEG) essentially as described by Tsubery et al., *J. Biol. Chem.* 279 (37) pp. 38118-38124. Alternatively, the formulation comprises a peptidyl moiety conjugated to hydroxyethyl starch (HES) or polyglycine or serum protein moiety or serum protein-binding moiety. Without being bound by any theory or mode of action, such formulations provide for extended or longer half-life of the peptide moiety in circulation.

In another example, a formulation comprises a nanoparticle comprising the peptide moiety or other active ingredient bound to it or encapsulated within it. Without being bound by any theory or mode of action, delivery of a peptidyl composition from a nanoparticle may reduce renal clearance of the peptide(s).

In another example, a formulation comprises a liposome carrier or excipient to facilitate uptake of an inhibitor into a cell. Liposomes are considered to interact with a cell by stable absorption, endocytosis, lipid transfer, and/or fusion (Egerdie et al., *J. Urol.* 142:390, 1989). For example, liposomes comprise molecular films, which fuse with cells and provide optimal conditions for wound healing (K. Reimer et al., *Dermatology* 195 (*suppl.* 2):93, 1999). Generally, liposomes have low antigenicity and can be used to encapsulate and deliver components that cause undesirable immune responses in patients (Natsume et al., *Jpn. J. Cancer Res.* 91:363-367, 2000)

For example, anionic or neutral liposomes often possess excellent colloidal stability, since substantially no aggregation occurs between the carrier and the environment. Consequently their biodistribution is excellent, and their potential for irritation and cytotoxicity is low.

Alternatively, cationic liposomal systems, e.g. as described in Mauer et al., *Molecular Membrane Biology*, 16: 129-140, 1999 or Maeidan et al., *BBA* 1464: 251-261, 2000 are useful for delivering compounds into a cell. Such cationic systems provide high loading efficiencies. Moreover, PEGylated cationic liposomes show enhanced circulation times in vivo (Semple *BBA* 1510, 152-166, 2001).

Amphoteric liposomes are a recently described class of liposomes having an anionic or neutral charge at pH 7.4 and a cationic charge at pH 4. Examples of these liposomes are described, for example, in WO 02/066490, WO 02/066012 and WO 03/070735. Amphoteric liposomes have been found to have a good biodistribution and to be well tolerated in animals and they can encapsulate nucleic acid molecules with high efficiency.

U.S. Ser. No. 09/738,046 and U.S. Ser. No. 10/218,797 describe liposomes suitable for the delivery of peptides or proteins into a cell.

Injectable Formulations

Injectable formulations comprising peptide(s) of the invention or other active ingredient and a suitable carrier or excipient preferably have improved stability and/or rapid onset of action, and are for intravenous, subcutaneous, intradermal or intramuscular injection.

For parenteral administration, the peptidyl component or other active ingredient, may be administered as injectable doses of a solution or suspension in a physiologically acceptable diluent with a pharmaceutical carrier which can be a sterile liquid such as water or oil e.g., petroleum, animal, vegetable or synthetic oil including any one or more of peanut oil, soybean oil, mineral oil, etc. Surfactant and other pharmaceutically acceptable adjuvants or excipients may be included. In general, water, saline, aqueous dextrose or other related sugar solution, ethanol or glycol e.g., polyethylene glycol or propylene glycol, is a preferred carrier.

The injectable formulations may also contain a chelator e.g., EDTA, and/or a dissolution agent e.g., citric acid. Such components may assist rapid absorption of the active ingredient into the blood stream when administered by injection.

One or more solubilizing agents may be included in the formulation to promote dissolution in aqueous media. Suitable solubilizing agents include e.g., wetting agents such as polysorbates, glycerin, a poloxamer, non-ionic surfactant, ionic surfactant, food acid, food base e.g., sodium bicarbonate, or an alcohol. Buffer salts may also be included for pH control.

Stabilizers are used to inhibit or retard drug decomposition reactions in storage or in vivo which include, by way of example, oxidative reactions, hydrolysis and proteolysis. A number of stabilizers may be used e.g., protease inhibitors, polysaccharides such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphospahtidylserine; phosphatidylglycerols; phosphatidylinositols; cardiolipins; sphingomyelins. In one example, the stabilizer may be a combination of glycerol, bacteriostatic agents and isotonic agents.

In one example, the peptidyl component or other active ingredient of an injectable formulation is provided as a dry powder in a sterile vial or ampoule. This is mixed with a pharmaceutically acceptable carrier, excipient, and other components of the formulation shortly before or at the time of administration. Such an injectable formulation is produced by mixing components such as a carrier and/or excipient e.g., saline and/or glycerol and/or dissolution agent and/or chelator etc to form a solution to produce a "diluent", and then and sterilizing the diluent e.g., by heat or filtration. The peptidyl component or other active agent is added separately to sterile water to form a solution, sterile-filtered, and a designated amount is placed into each of a number of separate sterile injection bottles. The peptide or other active agent solution is then lyophilized to form a powder and stored e.g., separately from the diluent to retain its stability. Prior to administration, the diluent is added to the injection bottle containing the dried peptidyl component or other active agent. After the predetermined amount of formulation is injected into the patient, the remaining solution may be stored, e.g., frozen or refrigerated.

In another example, the formulation is prepared as a frozen mixture ready for use upon thawing. For example, the peptidyl component or other active agent is combined with the diluent, sterile filtered into multi-use injection bottles or ampoules and frozen prior to use.

Intranasal Formulations

For intranasal administration, powdery preparations having improved absorbability have been proposed. They are prepared e.g., by adsorbing physiologically active linear peptides onto a polyvalent metal compound such as hydroxyapatite or calcium carbonate (e.g., EP 0 681 833 A2). Peptides can be cyclized to improve their stability and resistance to peptidases in the nasal mucosa e.g., by synthesis as a continuous cyclotide or by oxidation of flanking cysteine residues. Alternatively, peptides may be stabilized in a particular conformation by means of artificially 'stapling' using chemical linkers e.g., Walensky et al., Science 305, 1466-1470 (2004).

Preferably, the peptide is dispersed homogeneously in and adsorbed homogeneously onto a physiologically acceptable particulate carrier, which can be a physiologically acceptable powdery or crystalline polyvalent metal carrier and/or organic carrier, whose mean particle size is in the range of 20 to 500 microns. In a preferred form, the peptidyl inhibitor according to any example hereof is formulated for intranasal delivery an alkyl-saccharide transmucosal delivery-enhancing excipient such as Intraveil (Aegis Therapeutics).

Suitable polyvalent metal component of the carrier include physiologically acceptable metal compounds having more than 2 valency, and may include, for example, aluminum compounds, calcium compounds, magnesium compounds, silicon compounds, iron compounds and zinc compounds. Such metal compounds are commonly used as excipients, stabilizers, filing agents, disintegrants, lubricants, adsorbents and coating agents for medical preparations.

Preferred aluminum compounds include, for example, dry aluminum hydroxy gel, aluminum hydroxychloride, synthetic aluminum silicate, light aluminum oxide, colloidal aluminum silicate hydrate, aluminum magnesium hydroxide, aluminum hydroxide, aluminum hydroxide gel, aluminum sulfate, dihydroxyaluminum aminoacetate, aluminum stearate, natural aluminum silicate, aluminum monostearate and potassium aluminum sulfate. Among them, the preferable aluminum compound is aluminum hydroxide.

Preferred calcium compounds include, for example, apatite, hydroxyapatite, calcium carbonate, calcium disodium EDTA, calcium chloride, calcium citrate, calcium glycerophosphate, calcium gluconate, calcium silicate, calcium oxide, calcium hydroxide, calcium stearate, calcium phosphate tribasic, calcium lactate, calcium pantothenate, calcium oleate, calcium palmitate, calcium D-pantothenate, calcium alginate, calcium phosphate anhydride, calcium hydrogenphosphate, calcium primary phosphate, calcium acetate, calcium saccharate, calcium sulfate, calcium secondary phosphate, calcium para-aminosalicylate and bio-calcilutite compounds. Bio-calcilutite compounds such as crystalline calcium pyrophosphate, calcium secondary phosphate, octacalcium phosphate, tricalcium phosphate and crystalline calcium oxalate are analogous to hydroxyapatite and may also be used as a physiologically acceptable powdery or crystalline carrier. Preferable calcium compounds are hydroxyapatite, calcium carbonate or calcium lactate.

Preferred magnesium compound components of the physiologically acceptable powdery or crystalline carrier include, for example, magnesium L-aspartate, magnesium chloride, magnesium gluconate, magnesium aluminate silicate, magnesium silicate, magnesium oxide, magnesium hydroxide, magnesium stearate, magnesium carbonate, magnesium aluminate metasilicate, magnesium sulfate, sodium magnesium silicate and synthetic sodium magnesium silicate. Among them, preferable magnesium compound is magnesium stearate.

Other metal compounds with more than 2 valency may be silicon compounds such as silicon oxide hydrate, light silicic anhydride, synthetic hydrotalcite, diatomaceous earth and silicon dioxide; iron compounds such as ferrous sulfate; and zinc compounds such as zinc chloride, zinc stearate and zinc sulfate.

Particulate organic carriers may be a fine powder from grain, preferably of rice, wheat, buck wheat, barley, soybean, corn, millet, foxtail millet and the like.

Such formulations may optionally comprise an absorption enhancer. Preferred absorption enhancers which may be one of the components of the nasally administrable composition is a pharmaceutically acceptable natural (e.g. cellulose, starch and their derivatives) or unnatural polymer material. A preferred embodiment of the cellulose and its derivatives is microcrystalline cellulose, methyl cellulose, ethyl cellulose, hydroxypropyl cellulose, hydroxypropylmethyl cellulose, hydroxypropylmethyl cellulose phthalate, cellulose acetate, cellulose acetate phthalate, carboxymethyl cellulose, low carboxymethyl cellulose sodium, carboxymethylethyl cellulose and the like. A preferable embodiment of the starch and its derivatives is corn starch, potato starch, rice starch, glutinous rice starch, wheat starch, pregelatinized starch, dextrin, sodium carboxymethyl starch, hydroxypropyl starch, pullulan and the like. Other natural polymers such as agar, sodium alginate, chitin, chitosan, egg yolk lecithin, gum arabic, tragacanth, gelatine, collagen, casein, albumin, fibrinogen, and fibrin may also be used as absorption enhancer. A preferable embodiment of the unnatural polymer is sodium polyacrylate, polyvinyl pyrrolidone, and the like. Preferred absorption enhancers are fine powder of rice, glutinous rice, starch, gelatine, dextrin, hydroxypropyl cellulose, hydroxypropylmethyl cellulose, polyvinyl pyrrolidone, egg yolk lecithin, gum arabic, tragacanth or a mixture thereof. More preferable absorption enhancers are fine powder of glutinous rice, starch, gelatine, hydroxypropyl cellulose, hydroxypropylmethyl cellulose, polyvinyl pyrrolidone, tragacanth or a mixture thereof. Even more preferable absorption enhancers are fine powder of glutinous rice or hydroxypropyl cellulose. Most preferable absorption enhancer is fine powder of glutinous rice. The mean particle size of the absorption enhancer is preferably not more than 250 microns, more preferably from 20 to 180 microns.

The above absorption enhancers may be used alone or in combination of two or more absorption enhancers in the physiologically acceptable powdery or crystalline carrier.

Water-soluble carriers are preferred to increase adsorption of the active substance in the nasal mucosa. Alternatively, this is achieved by homogeneous dispersion of the active substance in a water-insoluble carrier e.g., hydroxyapatite, calcium carbonate, calcium lactate, aluminum hydroxide or magnesium stearate, preferably in the presence of an absorption enhancer, and homogeneously adsorbing the active substance there onto.

Calcium carbonate, calcium lactate, aluminum hydroxide or magnesium stearate is usually used as a stabilizer, lubricant, agent to add lustre, excipient, dispersing agent or coating agent for a pharmaceutical preparation; however, it has been found that these compounds having a mean particle size of not more than 500 microns can be used as a carrier for the intranasal formulations, and promote absorption of a physiologically active substances into the body by nasal administration.

Additional Components

In another example of the invention, a formulation comprises an additional component or compound e.g., a cytokine or growth factor, such as, for example, an interleukin e.g., IL-2 or IL-8, IL-10, IL-13 or IL-17 and/or an interferon molecule e.g., IFN-$\alpha$ or IFN-$\beta$ or IFN-$\gamma$ or IFN-$\lambda$ and/or transforming growth factor $\beta$ and/or platelet derived growth factor and/or nerve growth factor and/or heparin binding epidermal growth factor and/or epidermal growth factor and/or keratinocyte growth factor and/or platelet derived activating factor and/or platelet derived epithelial growth factor and/or a fibroblast growth factor an/or a keratinocyte growth factor. For example, Puolakkainen et al., *J. Surg. Res.,* 58: 321-329, 1995 describe formulations comprising transforming growth factor $\beta$; compositions comprising platelet derived growth factor have been described by Lepisto et al., *J. Surg. Res.,* 53: 596-601, 1992; formulations comprising fibroblast growth factor are described, for example, in Brown et al., *Surg.,* 121: 372-380, 1997; formulations comprising nerve growth factor are described in, for example, Matsuda et al., *J. Exp. Med.,* 187: 297-306, 1998.

Modes of Administration

The present invention contemplates any mode of administration of a medicament or formulation as described herein, however one or a plurality of intranasal and/or injected and/or oral doses is preferred. Combinations of different administration routes are also encompassed e.g., intranasal and/or intravenous and/or oral.

Compositions according to the present invention are administered in an aqueous solution as a nasal or pulmonary spray and may be dispensed in spray form by a variety of methods known to those skilled in the art. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering the solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien Ed., Elsevier Publishers, New York, 1985; and in U.S. Pat. No. 4,778,810 (each incorporated herein by reference). Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Nasal and pulmonary spray solutions of the present invention typically comprise the drug or drug to be delivered, optionally formulated with a surface active agent, such as a nonionic surfactant (e.g., polysorbate-80), and one or more buffers. In some embodiments of the present invention, the nasal spray solution further comprises a propellant. The pH of the nasal spray solution is optionally between about pH 6.8 and 7.2, but when desired the pH is adjusted to optimize delivery of a charged macromolecular species (e.g., a therapeutic protein or peptide) in a substantially non-ionized state. The pharmaceutical solvents employed can also be a slightly acidic aqueous buffer (pH 4-6). Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, benzylalkonimum chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, mucosal formulations are administered as dry powder formulations comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5 micron mass median equivalent aerodynamic diameter (MMEAD), commonly about 1 micron MMEAD, and more typically about 2 micron MMEAD. Maximum particle size appropriate for deposition within the nasal passages is often about 10 micron MMEAD, commonly about 8 micron MMEAD, and more typically about 4 micron MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI) which rely on the patient's breath, upon pulmonary or nasal inhalation, to disperse the power into an aerosolized amount. Alternatively, the dry powder may be administered via air assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the biologically active agent is lower than this amount, the powdered active agent will typically be combined with a pharmaceutical dry bulking powder to provide the required total powder mass. Preferred dry bulking powders include sucrose, lactose, dextrose, mannitol, glycine, trehalose, human serum albumin (HSA), starch e.g., hydroxyethyl starch (HES). Other suitable dry bulking powders include cellobiose, dextrans, maltotriose, pectin, sodium citrate, sodium ascorbate, and the like.

Standard methods are used to administer injectable formulations of the present invention.

Medical Indications

The invention can be used for treatment or prophylaxis of any mammalian subject in need of, or already receiving, therapy for one or more consequences of aberrant or inappropriate CD40L-dependent signaling, including CD40L-dependent CD40-mediated signaling or CD40L-mediated signaling.

In one example, an inhibitor of the present invention as described according to any example hereof is for treatment or therapy of a subject in need thereof e.g., for attenuation or alleviation or amelioration of an inappropriate or adverse humoral immune response, such as an immune response associated with or causative of an autoimmune disease. Alternatively, or in addition, an inhibitor of the present invention as described according to any example hereof is for preventing or reducing an immune response against an antigen having a therapeutic or adaptive benefit to a subject. Alternatively, or in addition, an inhibitor of the present invention as described according to any example hereof is for use in a method to prevent or reduce a counter-adaptive immune response in a subject.

As used herein, the term "treatment" or "therapy" means to improve a subject's clinical state e.g., by reducing, alleviating, ameliorating or preventing one or more adverse indications of a disease, condition or syndrome. The treatment or therapy may involve complete abrogation of adverse indication(s) or comprise a partial improvement therein.

In another example, an inhibitor of the present invention as described according to any example hereof is for therapy of an autoimmune disease.

As used herein, "autoimmune disease" describes a disease state or syndrome whereby a subject's body produces a dysfunctional immune response against the subject's own body components, with adverse effects. This may include production of B cells producing antibodies with specificity for all antigens, allergens or major histocompatibility (MHC) antigens, or it may include production of T cells bearing receptors that recognize self-components and produce cytokines that cause inflammation. Examples of autoimmune diseases include, but are not limited to, ulcerative colitis, Crohn's disease, multiple sclerosis, rheumatoid arthritis, diabetes mellitus, pernicious anemia, autoimmune gastritis, psoriasis, Bechet's disease, Wegener's granulomatosis, Sarcoidois, autoimmune thyroiditis, autoimmune oophoritis, bullous pemphigoid, phemphigus, polyendocrinopathies, Still's disease, Lambert-Eaton myasthenia syndrome, myasthenia gravis, Goodpasture's syndrome, autoimmune orchitis, autoimmune uveitis, systemic lupus erythematosus, multiple sclerosis, Sjogren's Syndrome and ankylosing spondylitis.

In one example, the autoimmune disease is rheumatoid arthritis e.g., wherein the inhibitor reduces or prevents CD40L-dependent induction of anti-collagen antibodies. In another example, the autoimmune disease is type I diabetes. In another example, the autoimmune disease is systemic lupus erythematosus (SLE) e.g., wherein the inhibitor reduces or prevents CD40L-dependent anti-dsDNA and anti-nucleosomal autoantibody production. In another example, the autoimmune disease is multiple sclerosis e.g., wherein the inhibitor reduces or prevents CD40L-dependent anti-myelin autoantibody production.

In another example, an inhibitor of the present invention as described according to any example hereof is for therapy of inflammation e.g., inflammation associated with an autoimmune disease, periodic fever syndrome, sepsis or acute respiratory distress syndrome.

In another example, an inhibitor of the present invention as described according to any example hereof is for therapy of idiopathic thrombocytopenic purpura (ITP).

In another example, an inhibitor of the present invention as described according to any example hereof is for therapy of irritable bowel syndrome/disease (IBD).

In another example, an inhibitor of the present invention as described according to any example hereof is for therapy of one or more CD40L-dependent vascular complication of diabetes e.g., cardiac ischemia, atherosclerosis.

In another example, a peptidyl inhibitor of the present invention as described according to any example hereof is for reducing the risk of complication of transplantation by blocking a CD40L regulated process involved in graft rejection.

In another example, an inhibitor of the present invention as described according to any example hereof attenuates or ameliorates bio-inhibitory humoral immunity against one or more therapeutic proteins e.g., thrombin, clotting factor such as factor VIII, one or more cytokines e.g., an interleukin (IL) such as IL-2 or an interferon (IFN) such as IFN-$\alpha$, IFN-$\beta$, IFN-$\gamma$ or IFN-$\lambda$. For example, in the therapy of hemophilia, subjects at risk of developing humoral immunity to factor VIII may be treated with an inhibitor of the present invention. Similarly, subjects suffering from an autoimmune disease e.g., multiple sclerosis, or a viral infection e.g., HCV infection and receiving interferon therapy may be treated with an inhibitor of the present invention. Procedures for determining whether a subject has developed an inhibitory response against a therapeutic peptide are well known e.g., Hematology: Clinical and Laboratory Practice, vol. 2, Bick, ed., Mosby-Year Book, Inc., publ. (1993), pp. 1544-1548.

The subject will be a mammalian animal, e.g., a human or non-human animal, such as a domesticated non-human mammal, including a companion or laboratory mammal, e.g., selected from chimpanzees, monkeys, sheep, horses, cattle, goats, pigs, dogs, cats, rabbits, guinea pigs, hamsters, gerbils, rats and mice. For example, the subject may be a subject afflicted with, or at risk of, developing an autoimmune disease or other CD40L-dependent condition such as an exogenous protein inhibitor syndrome.

The present invention is described further in the following non-limiting examples:

Example 1

Isolation and Characterization of Representative Peptidyl Inhibitors

This example provides representative peptidyl inhibitors of the present invention and describes methods for their isolation and validation. Additional peptidyl inhibitors of the invention are provided in the basic application, incorporated herein by reference.

Peptide Display

Using phage display, expression libraries produced from fragments of prokaryote and eukaryote compact genomes, including *Salmonella enterica, Bacillus subtilis, Listeria innocua, Neisseria meningitidis, Escherichia coli, Thermotoga maritima, Sulfolobus solfataricus, Borrelia burgdorferi, Deinococcus radiodurans, Campylobacter jejuni, Geobacter sulfurreducens, Pseudomonas aeruginosa, Bordetella pertussis, Haloarcula marismortui* and *Chlorobium tepidum*. The genome fragments inserted into the phage display libraries encode peptides, including natural open reading frames, capable of forming secondary structures or super-secondary structures (including folds, domains and sub-domains of proteins). Because the fragments are derived from prokaryotes or non-mammalian eukaryotes having compact genomes, the encoded peptides do not bind CD40L in their native context.

Peptides were displayed in trans with the p3 protein from the vector pJuFo. Alternatively, the peptides were displayed as fusion proteins with the p3 protein, wherein nucleic acid encoding the peptidyl inhibitor was positioned downstream of a PelB leader sequence and upstream of a sequence encoding an HA-p3 fusion moiety, and wherein the vector was configured such that the proportion of natural open reading frames displayed in the PelB-peptidyl inhibitor-HA-p3 fusion peptide is enhanced.

Base Peptides

In primary biopanning with CD40L, the inventors identified peptides that bind to CD40L. Table 2 provides the sequences of representative base peptides i.e., SEQ ID Nos: 1-18.

Modification of Base Peptides by Removal of Internal Cysteine Residues

The sequences of the base peptides having internal or C-terminal cysteine residues were modified by synthesizing the peptides with a serine residues in place of the cysteine. The sequences of the derivative peptides are provided in Table 3 i.e., SEQ ID Nos: 19-34.

Chiral Analogs of Base Peptides and Serine Derivatives

The inventors have also produced retro-inverted analogs of the base peptides comprising e.g., two or more retro-inverted amino acids and preferably, comprising a reversed amino acid sequence wherein all amino other than glycine (which is not chiral) are D-amino acids. The amino acid sequences of representative chiral analogs are set forth in Table 4 i.e., SEQ ID Nos: 35-43.

Modification of Base Peptides by Directed Evolution

The inventors have also produced multimeric forms of the peptides comprising one or two or three CD40L peptide ligands of the invention. In one example, a recombinase-based system of the present invention is used to produce the multimeric peptides. In another example, cysteine-containing linkers have been added to the peptides as described in the preceding paragraph and the peptides have been dimerized by chemical oxidation of the sulfhydryl group on the terminal cysteine residue e.g., using aldrithiol-2. Homodimers and heterodimers have been produced and assayed by chemiluminescent proximity assay for their ability to inhibit CD40L-CD40 interaction.

In one example, homodimers and heterodimers comprising the peptide CD40LM1_6 were produced, including heterodimers comprising the peptide CD40LM1_6 and a peptide selected from CD40LM1_4, CD40LM1_9, and CD40LM7_189.

In another example, peptide monomers are separated by tetra-glycine spacer or linker. A representative sequence of a heterodimeric peptide is presented in Table 2 (SEQ ID No: 44), which comprises the CD40L M1_206 monomer fused to a second peptidyl inhibitory monomer via a tetra-glycine spacer.

Modification of Base Peptides by Addition of PEG Moiety

The inventors have also produced, or will produce, derivatives of the peptides and analogs set forth in Tables 2 to 4 (SEQ ID Nos: 1-44) comprising polyethylene glycol or "PEG" (i.e., PEGylated peptides) added to their N-termini.

The N-terminal PEG residues may be separated from the peptidyl inhibitor by a linker or spacer. The linker or spacer may be e.g., an 8-amino-3,6-dioxaoctanoyl linker, an 8-amino-3,6-dioxaoctanoyl cysteine spacer, an 8-amino-3,6-dioxaoctanoyl lysine spacer, an 8-amino-3,6-dioxaoctanoyl lysyl cysteine spacer, or 8-amino-3,6-dioxaoctanoyl lysyl-lysyl-cysteine spacer. Exemplary spacers lined to the N-terminus of a peptide are represented schematically in FIGS. 1*a* to 1*c*. Exemplary peptide dimers separated by spacers are represented schematically in FIGS. 1*d* and 1*e*.

Exemplary PEGylated peptides are set forth in Tables 2 to 4 hereof i.e., the peptides for which kinetic data are provided.

Competitive Inhibition of Binding to CD40L

In a primary validation assay, the ability of base peptides to bind specifically to CD40L was confirmed by demonstrating that soluble CD40L was able to compete with the peptide displayed by the phage for binding to bound CD40L. In particular, CD40L-binding activity of phage displaying the peptides was inhibited by soluble CD40L with $IC_{50}$ values of less than 500 nM. Representative data obtained in such assays are presented in FIG. 2 for peptides CD40L M2_74, CD40L M2_82, CD40L M2_83 and CD40L M2_85. The $IC_{50}$ values of a sub-set of exemplary peptidyl inhibitors of the invention i.e., peptides CD40L M1_6, CD40L M1_9, CD40L M1_18, and CD40L M1_50, are also presented in Table 2 hereof.

Determination of Association and Dissociation Constants

Label-free analyses of the associations and dissociations of base peptides and serine derivatives of base peptides with the CD40L target protein were performed using the Octet Red system (ForteBio, Inc., USA) according to the manufacturer's instructions. These analyses provide kinetic constants of CD40L binding activity, especially the association rate constant ($K_a$) and dissociation rate constant ($K_d$) of binding, i.e., measures of the "on" and "off" rates of the peptides relative to soluble CD40L.

The equilibrium dissociation constant values ($K_D$) are presented in Tables 2 and 3. Data show that the higher affinity CD40L-binding peptides are generally encoded by natural open reading frames of bacteria or eukaryotes having compact genomes e.g., peptides CD40L M8_720, CD40L M8_721, CD40L M8_747, CD40L M8_748, CD40L M9_763, CD40L M9_780, CD40L M9_789 (SEQ ID Nos: 12-18), supporting the hypothesis that protein domains have evolved in these organisms to form stable structures. However, high affinity CD40L-binding peptides were also derived from display in pJuFo e.g., peptides CD40L M1_6, CD40L M1__9, CD40L M1__18 and CD40L M1__42 (SEQ ID Nos: 1-3 and 5). For those peptides that were modified by substitution of cysteine residues for serine residues, the binding affinity as determined by dissociation constant in the Octet Red assay was generally reduced e.g., compare $K_D$ values for peptides in Table 3 to data in Table 2, again supporting the hypothesis that natural open readings represent structures optimized in nature.

Chemiluminescent Proximity Assay

The specificities of the interactions between CD40L and of base peptides or serine derivatives of base peptides or chiral analogs of base peptides, were also demonstrated by chemiluminescent proximity assay employing (i) streptavidin-coated beads; (ii) a biotinylated phospho-CD40L; and (iii) protein A-conjugated beads having bound thereto CD40 receptor (CD40), wherein the biotinylated phospho-CD40L is captured by the streptavidin-coated donor beads via biotin-streptavidin interaction, and then specific peptides and protein A-conjugated CD40 acceptor beads are added. When the CD40L-CD40 interaction occurs, excitation at 680 nm produces an emission at wavelengths in the range of about 520 nm to about 620 nm. If the interaction is inhibited by the peptides, then emission in the 520-620 nm range is reduced or inhibited.

In one example, the Alphascreen assay (PerkinElmer) was employed according to the manufacturer's instructions. Alphascreen data presented herein demonstrate that peptides of the invention have high affinities for CD40L and are able to inhibit CD40-CD40L interactions in the nanomolar concentration range. Representative data obtained in Alphascreen assays are presented in FIGS. 3a-3d hereof for peptides CD40LM1__6; CD40LM1__4; CD40LM1_CD40LM1__9; and CD40LM7__189.

Figure 4:
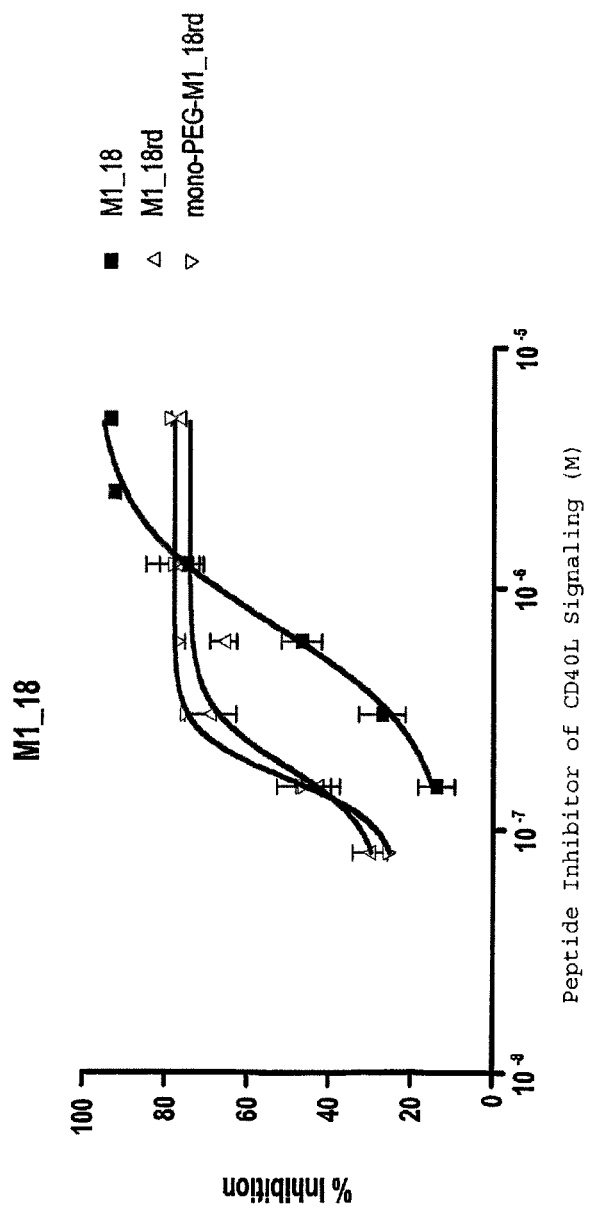
FIG. 4 is a graphical representation showing concentration-dependent inhibition of CD40L-induced 0086 expression on primary B-cells using peptide inhibitor of CD40L signaling M1_18 and enhanced inhibition thereof with a retroinverted form of peptide inhibitor of CD40L signaling M1_18 (M1-18rd) or a PEGylated form of the retroinverted peptide (mono-PEG-M1_18rd).

Data presented in Tables 2 and 3 and 4 hereof show the $EC_{50}$ values (i.e., the concentration producing a 50% reduction in control emission at 520-620 nm) for monomeric non-PEGylated (unmodified) and monomeric PEGylated base peptides, serine derivatives and chiral analogs. These data shown that the affinity of binding to CD40L to inhibit the CD40-CD40L interaction is generally enhanced for serine derivative and chiral analogs compared to the base peptides, and that PEGylated chiral analogs may exhibit even higher affinity for CD40L in the inhibition of the CD40-CD40L interaction. Representative data provided in FIG. 4 for peptide CD40L M1__18 support this conclusion, because the PEGylated chiral analog has a significantly higher affinity of binding than the core peptide or the retroinverted form alone, as evidenced by a reduced $EC_{50}$ value for the PEGylated chiral analog.

Homodimers and heterodimers were also assayed by chemiluminescent proximity assay for their ability to inhibit CD40L-CD40 interaction. Data shown in Table 5 and FIGS. 5a-5e hereof for exemplary dimeric forms of the CD40L peptide ligands of the invention demonstrate a significantly higher affinity of binding than a corresponding monomeric peptide, in the chemiluminescent proximity assay. Data presented in Table 2 for SEQ ID NO: 44 also demonstrate a 6-fold higher affinity for CD40L than the base monomeric peptide CD40L M1__206 which forms the N-terminal moiety of the heterodimer.

TABLE 2

Base peptidyl inhibitors and kinetic characteristics

| Peptide | Amino acid sequence (SEQ ID NO.) | $IC_{50}$ nM (nM) | $K_D$ (nM) | $EC_{50}$ nmodified) CD40L/CD40-Fc/BAF617 (nM) | $EC_{50}$ (PEGylated) CD40L/CD40-Fc/BAF617 (nM) |
|---|---|---|---|---|---|
| CD40L M1_6 | HPFSIKNVFCIWNFFSVY (SEQ ID NO: 1) | 16.3 | 24 | 440 | |
| CD40L M1_9 | PPRYNLFFLFRFYCSFRRDYLYF (SEQ ID NO: 2) | 81.1 | 8 | 370 | |
| CD40L M1_18 | LPFVPYRSHVLKYGWFFPVQWSIFAVLPFQYLHRCR (SEQ ID NO: 3) | 25.0 | 2.3 | 350 | |
| CD40L M1_30 | DAAGREFFQIAGLFSFRHHWWQA (SEQ ID NO: 4) | | | | |
| CD40L M1_42 | HSFVLFGVNVPFNIIDFQMRVKC (SEQ ID NO: 5) | | 30 | 200 | |
| CD40L M1_50 | PRWVRNRFYCLFVPSGVQRGGIHLWFSNWVR (SEQ ID NO: 6) | 45.8 | | | |
| CD40L M1_82 | SIQYHWRYSRFKYYFQLIWVYYCHV (SEQ ID NO: 7) | | | | 120 |
| CD40L M2_159 | LLYVKVICFFCMLVQYNNFQTYK (SEQ ID NO: 8) | | | 120 | |
| CD40L M7_189 | LLLFFFSPPFSIFCFSLTTLS (SEQ ID NO: 9) | | | 120 | |
| CD40L M7_206 | PFTWRPTIFWIIQLIVYMRHF (SEQ ID NO: 10) | 280 | | 190 | 88 |
| CD40L M7_217 | LCEMIAIYVFLWKKVFL (SEQ ID NO: 11) | | | | |
| CD40L M8_720 | RLPETRKAQAALATKYGIYGFcYYHYWFNGRRILESPVD AMLESGEPDFPFMLcWANENWT (SEQ ID NO: 12) | | 4 | 238 | |
| CD40L M8_721 | LWRLNEWNYSDAELLSLIEWcIDH (SEQ ID NO: 13) | | 7 | 524 | |
| CD40L M8_747 | LAEHAVWSLKcFPDWEWYNINIFGTDDPNHFWVEcDGHG KILFPGYPEGYYENHFLHSFELED (SEQ ID NO: 13) | | 8 | 197 | |
| CD40L M8_748 | RIESLEGEMWLINPFNGETLDEHTLEVWLK (SEQ ID NO: 15) | | 5 | 184 | |

TABLE 2 -continued

Base peptidyl inhibitors and kinetic characteristics

| Peptide | Amino acid sequence (SEQ ID NO.) | IC$_{50}$ nM (nM) | K$_D$ (nM) | EC$_{50}$(unmodified) CD40L/CD40-Fc/BAF617 (nM) | EC$_{50}$(PEGylated) CD40L/CD40-Fc/BAF617 (nM) |
|---|---|---|---|---|---|
| CD40L M9_763 | LDLFGDFNGLPEGADRTEFYQHEGHWQNRMILGDSLQVMASLAEREGLRGKVQcIYFDPPYGIKFN (SEQ ID NO: 16) | | 27 | | |
| CD40L M9_780 | LWPESWGGLPPASFFDELDPcINRHLRYPLFSETFTADLPVGTL (SEQ ID NO: 17) | | 12 | >1000 | |
| CD40L M9_789 | LLAEQAGTLKSELEAMPLGEYEHAARYVSEVEcNWKTFAGNYSEcDHcHANHQDWITDIELEESELEVNDYHWILHYTHDEDVEDEMRIHDEHEAKFYYFWPNFT (SEQ ID NO: 18) | | 4 | 331 | |
| CD40L D1_0014 | PFTWRPTIFWIIQLIVYMRHFGGGGSRSELLRENICRYVSLFDHPLQRNTPLDELRFVIFDTETSGFDLVKDRILSIR (SEQ ID NO: 44) | | 48 | | |

TABLE 3

Derivative peptidyl inhibitors comprising Cys-Ser modification and kinetic characteristic

| Peptide | Amino acid sequence (SEQ ID NO.) | K$_D$ value (nM) | EC$_{50}$(PEGylated) CD40L/CD40-Fc/BAF617 (nM) |
|---|---|---|---|
| CD40L M1_6s | HPFSIKNVFSIWNFFSVY (SEQ ID NO: 19) | | 48 |
| CD40L M1_9s | PPRYNLFFLFRFYSSFRRDYLYF (SEQ ID NO: 20) | 300 | 48 |
| CD40L M1_18s | LPFVPYRSHVLKYGWFFPVQWSIFAVLPFQYLHRSR (SEQ ID NO: 21) | | 3,300 |
| CD40L M1_30s | DAAGREFFQIAGLFSFRHHWWQA (SEQ ID NO: 22) | 400 | 32 |
| CD40L M1_42s | HSFVLFGVNVPFNIIDFQMRVKS (SEQ ID NO: 23) | 100 | 112 |
| CD40L M1_50s | PRWVRNRFYSLFVPSGVQRGGIHLWFSNWVR (SEQ ID NO: 24) | 600 | 1500 |
| CD40L M1_82s | SIQYHWRYSRFKYYFQLIWVYYSHV (SEQ ID NO: 25) | | 120 |
| CD40L M2_159s | LLYVKVISFFSMLVQYNNFQTYK (SEQ ID NO: 26) | | 120 |
| CD40L M7_189 | LLLFFFSPPFSIFSFSLTTLS (SEQ ID NO: 27) | | 120 |
| CD40L M7_217s | LSEMIAIYVFLWKKVFL (SEQ ID NO: 28) | 100 | |
| CD40L M8_720s | RLPETRKAQAALATKYGIYGFSYYHYWFNGRRILESPVDAMLESGEPDFPFMLSWANENWT (SEQ ID NO: 29) | | |
| CD40L M8_721s | LWRLNEWNYSDAELLSLIEWSIDH (SEQ ID NO: 30) | | |
| CD40L M8_747s | LAEHAVWSLKSFPDWEWYNINIFGTDDPNHFWVESDGHGKILFPGYPEGYYENHFLHSFELED (SEQ ID NO: 31) | | |
| CD40L M9_763s | LDLFGDFNGLPEGADRTEFYQHEGHWQNRMILGDSLQVMASLAEREGLRGKVQSIYFDPPYGIKFN (SEQ ID NO: 32) | | |
| CD40L M9_780s | LWPESWGGLPPASFFDELDPSINRHLRYPLFSETFTADLPVGTL (SEQ ID NO: 33) | | |
| CD40L M9_789s | LLAEQAGTLKSELEAMPLGEYEHAARYVSEVESNWKTFAGNYSESDHSHANHQDWITDIELEESELEVNDYHWILHYTHDEDVEDEMRIHDEHEAKFYYFWPNFT (SEQ ID NO: 34) | | |

TABLE 4

Representative chiral analogs of base peptidyl inhibitors and kinetic characteristics

| Peptide | Amino acid sequence (SEQ ID NO.) | EC$_{50}$(PEGylated) CD40L/CD40-Fc/BAF617 (nM) |
|---|---|---|
| CD40L M1_6rd | YVSFFNWISFVNKISFPH (SEQ ID NO: 35) | 20 |
| CD40L M1_9rd | FYLYDRRFSSYFRFLFFLNYRPP (SEQ ID NO: 36) | 14 |
| CD40L M1_18rd | RCRHLYQFPLVAFISWQVPFFWGYKLVHSRYPVFPL (SEQ ID NO: 37) | 688 |
| CD40L M1_30rd | AQWWHHRFSFLGAIQFFERGAAD (SEQ ID NO: 38) | 24 |
| CD40L M1_42rd | SKVRMQFDIINFPVNVGFLVFSH (SEQ ID NO: 39) | 16 |
| CD40L M1_50rd | RVWNSFWLHIGGRQVGSPVFLSYFRNRVWRP (SEQ ID NO: 40) | 568 |
| CD40L M1_82rd | VHSYYVWILQFYYKFRSYRWHYQIS (SEQ ID NO: 41) | 10 |
| CD40L M7_206rd | FHRMYVILQIIWFITPRWTFP (SEQ ID NO: 42) | 12 |
| CD40L M7_217rd | LFVKKWLFVYIAIMESL (SEQ ID NO: 43) | |

TABLE 5

Enhanced inhibition of CD40L-CD40 interaction by dimeric peptides as determined by Alphascreen proximity assay

| Peptide | EC50 (nM) |
|---|---|
| M1_6S | 0.1225 to 0.323 |
| Cys_M1_6S | 0.2646 |
| M1_4S | 1.616 |
| M1_9S | 0.5643 |
| M7_189S | 0.1765 |
| Cys_M1_6S homodimer | 0.04891 |
| Cys_M1_6S-Cys_M1_4S heterodimer | 0.06121 |
| Cys_M1_6S-Cys_M1_9S heterodimer | 0.03 |
| Cys_M1_6S-Cys_M1_189S heterodimer | 0.0001739 |

S denotes C-terminal serine;
Cys denotes N-terminal cysteine

Bioassays

To further validate the CD40L peptide antagonists identified by the inventors, bioassays are performed which determine the ability of a peptide of the invention or an analog or derivative thereof to inhibit or antagonize one or more CD40L-dependent biological activities known in the art.

1. Inhibition of Cd86 Expression on Primary B Cells

In one example, the ability of a peptide, analog or derivative of the invention to inhibit or reduce or delay expression of CD86 on primary B-cells was determined in the presence and absence of the peptides, analogs and derivatives of the invention. In particular, CD86 expression was determined by FACS.

Figure 5:
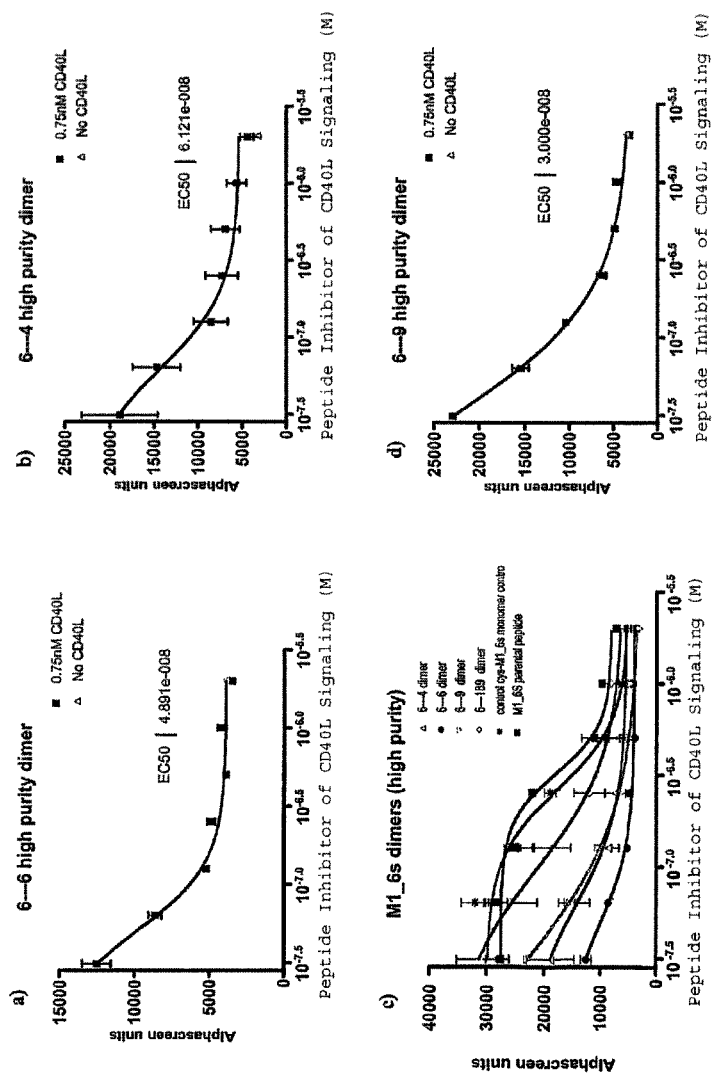
FIG. 5a is a graphical representation showing inhibition of the interaction between CD40L and CD40 by a peptide consisting of a homodimer of the peptide inhibitor of CD40L signaling M1_6 as determined by Alphascreen proximity assay (Perkin Elmer, USA).
FIG. 5b is a graphical representation showing inhibition of the interaction between CD40L and 0040 by a peptide consisting of a heterodimer of the peptide inhibitor of CD40L signaling M1_6 and the peptide inhibitor of CD40L signaling M1_4, as determined by Alphascreen proximity assay (Perkin Elmer, USA).
FIG. 5c is a graphical representation showing inhibition of the interaction between CD40L and 0040 by several dimeric peptides relative to a control monomer peptide consisting of the M1-6S monomeric peptide unit or the cysteine-containing derivative thereof. Cys-M1_6S. Dimeric peptides included a homodimer of the peptide inhibitor of CD40L signaling M1_6 (6-6 dimer), a heterodimer of the peptide inhibitor of CD40L signaling M1_6 and the peptide inhibitor of CD40L signaling M1_4 (6-4 dimer), a heterodimer of the peptide inhibitor of CD40L signaling M1_6 and the peptide inhibitor of CD40L signaling M1_9 (6-9 dimer), and a heterodimer of the peptide inhibitor of CD40L signaling M1_6 and the peptide inhibitor of CD40L signaling M1_189 (6-189 dimer). Data indicate enhanced inhibition of CD40L-CD40 interaction by binding of dimeric peptides relative to the monomeric peptide controls, as determined by Alphascreen proximity assay (Perkin Elmer, USA).
FIG. 5d is a graphical representation showing inhibition of the interaction between CD40L and CD40 by a high purity heterodimer of the peptide inhibitor of CD40L signaling M1_6 and the peptide inhibitor of CD40L signaling M1_9 (6-9 high purity dimer), as determined by Alphascreen proximity assay (Perkin Elmer, USA).
FIG. 5e is a graphical representation showing inhibition of the interaction between CD40L and CD40 by a high purity heterodimer of the peptide inhibitor of CD40L signaling M1_6 and the peptide inhibitor of CD40L signaling M1_189 (6-189 high purity dimer), as determined by Alphascreen proximity assay (Perkin Elmer, USA).
Figure 5:
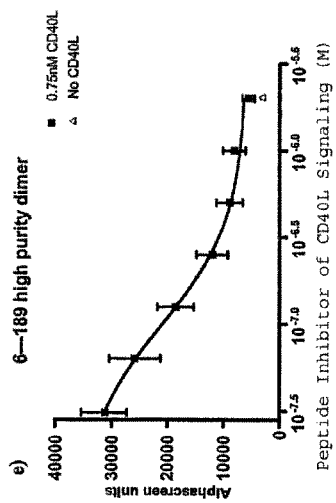
Figure 6:
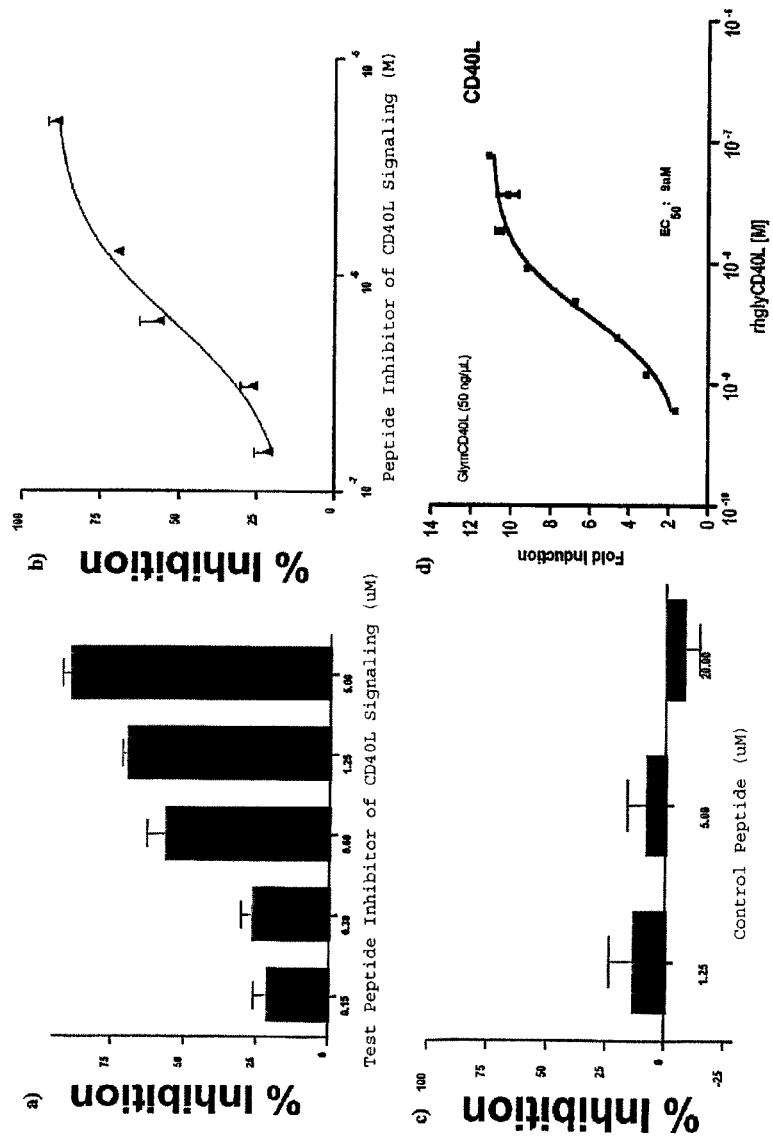
FIG. 6a is a graphical representation showing percentage inhibition of CD40L-induced CD86 expression on primary B-cells by the peptide inhibitor of CD40L signaling M1_18.
FIG. 6b is a graphical representation showing lack of significant inhibition of CD40L-induced CD86 expression on primary B-cells by a control peptide that does not bind CD40L.
FIG. 6c is a graphical representation showing concentration-dependent inhibition of CD40L-induced CD86 expression on primary B-cells by the peptide inhibitor of CD40L signaling M1_18.
FIG. 6d is a graphical representation showing concentration-dependent induction of CD40L-induced CD86 expression on primary B-cells by CD40L in a control experiment for data provided in FIGS. 6a and 6c and 6e.
FIG. 6e is a graphical representation showing concentration-dependent inhibition of CD40L-induced CD86 expression on primary B-cells by CD40L by the peptide inhibitor of CD40L signaling M1_18S compared to the effect of negative controls consisting of LPS or media.
FIG. 6f is a graphical representation showing concentration-dependent induction of CD40L-induced CD86 expression on primary B-cells by LPS in a control experiment for data provided in FIGS. 6a and 6c and 6e.
FIG. 6g is a graphical representation showing lack of concentration-dependent inhibition of LPS-induced CD86 expression on primary B-cells by peptide inhibitor of CD40L signaling M1_18S, indicating that the effect of the peptides is not mediated by LPS binding to TLR2/4.
FIG. 6h is a graphical representation showing concentration-dependent induction of cell death by TNFα in a control experiment for data provided in FIG. 6j.
FIG. 6i is a graphical representation showing inhibition of concentration-dependent induction of cell death by TNFα using a recombinant human TNF receptor (TNFRII) in a control experiment for data provided in FIG. 6j.
FIG. 6j is a graphical representation showing lack of inhibition of concentration-dependent induction of cell death by TNFα using peptide inhibitors of CD40L signaling M1_2S, M1_5S, M1_6S, M1_7S, M1_2S, M1_9S and M1_2S, M1_18*S, indicating that the effect of the peptides is not mediated by TNFα.
Figure 6:
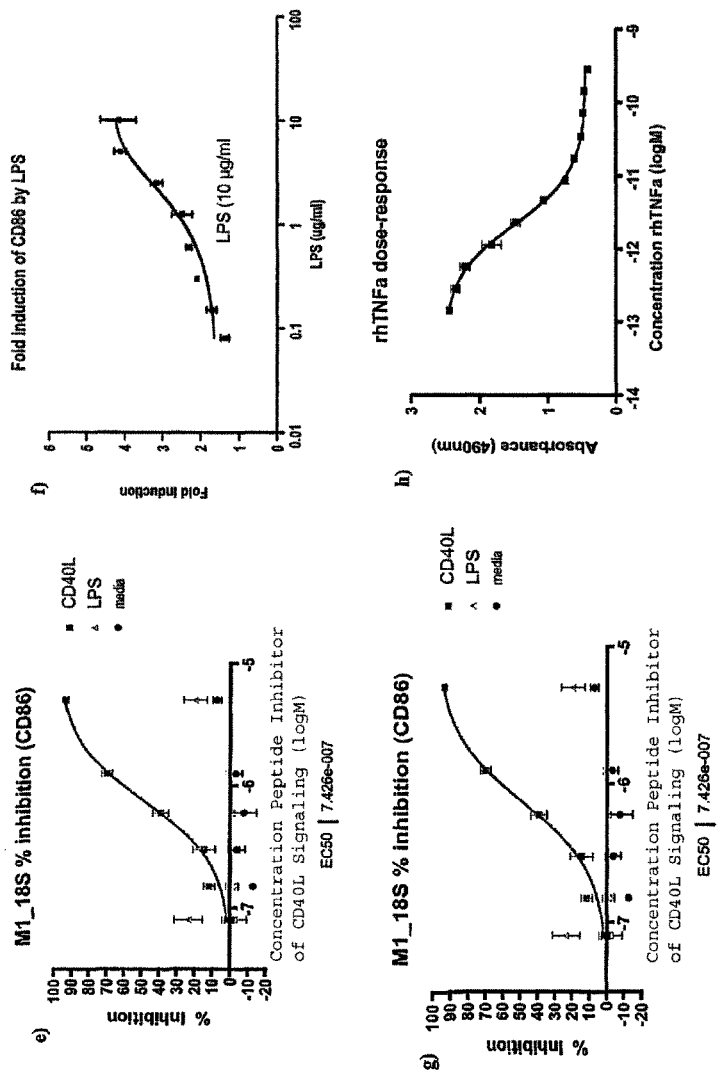
Figure 6:
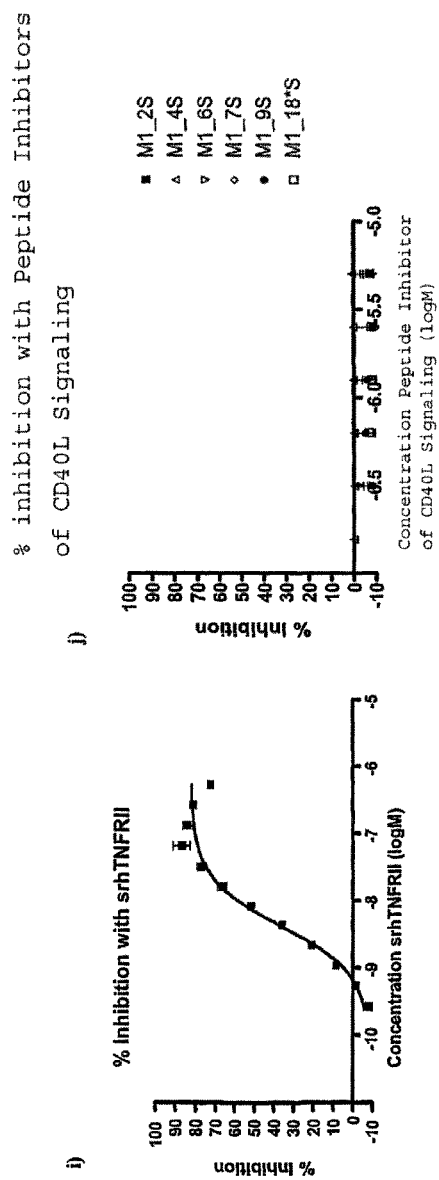
Figure 7:
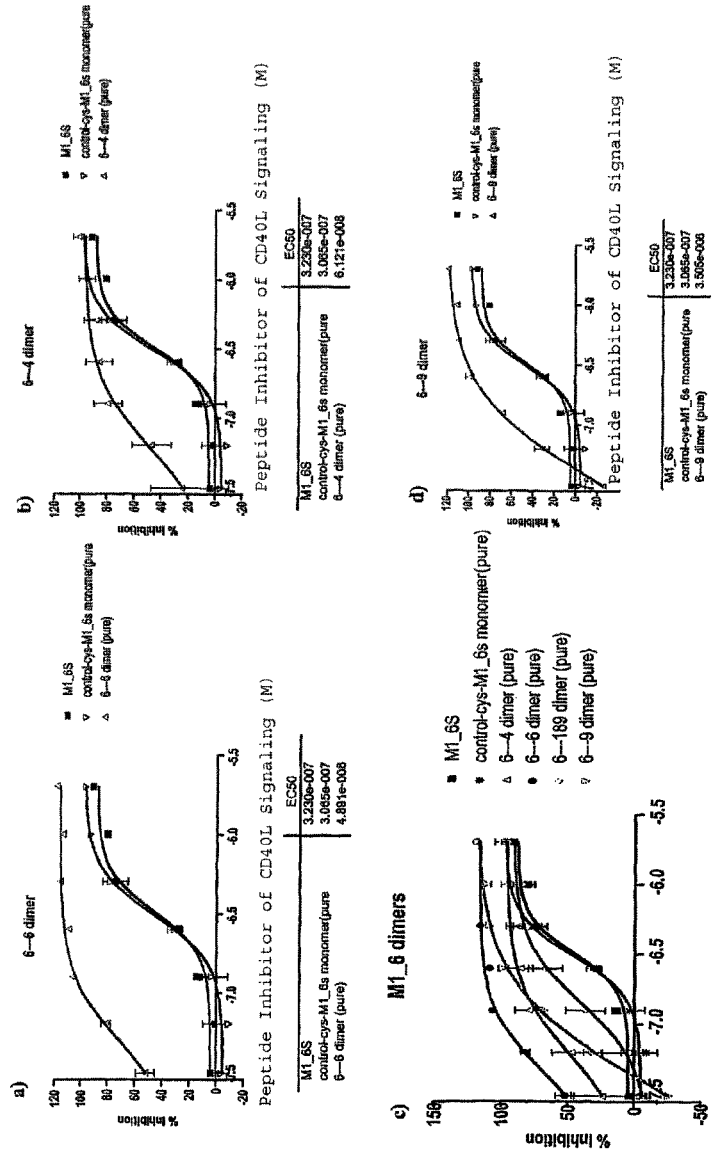
FIG. 7a is a graphical representation showing percentage inhibition of CD40L-induced CD86 expression on primary B-cells by a homodimer of the peptide inhibitor of CD40L signaling M1_6 (6-6 dimer) relative to a control monomer peptide consisting of the M1-6S monomeric peptide unit or the cysteine-containing derivative thereof. Cys-M1_6S. $EC_{50}$ values are also indicated for each peptide. Data indicate enhanced inhibition of CD40L-induced CD86 expression by dimeric peptide relative to the monomeric peptide controls.
FIG. 7b is a graphical representation showing percentage inhibition of CD40L-induced CD86 expression on primary B-cells by a heterodimer of the peptide inhibitor of CD40L signaling M1_6 and the peptide inhibitor of CD40L signaling M1_4 (6-4 dimer) relative to a control monomer peptide consisting of the M1-6S monomeric peptide unit or the cysteine-containing derivative thereof. Cys-M1_6S. $EC_{50}$ values are also indicated for each peptide. Data indicate enhanced inhibition of CD40L-induced CD86 expression by dimeric peptide relative to the monomeric peptide controls.
FIG. 7c is a graphical representation showing percentage inhibition of CD40L-induced CD86 expression on primary 3-cells by several dimeric peptides relative to a control monomer peptide consisting of the M1-6S monomeric peptide unit or the cysteine-containing derivative thereof. Cys-M1_6S. Dimeric peptides included a homodimer of the peptide inhibitor of CD40L signaling M1_6 (6-6 dimer), a heterodimer of the peptide inhibitor of CD40L signaling M1_6 and the peptide inhibitor of CD40L signaling M1_4 (6-4 dimer), a heterodimer of the peptide inhibitor of CD40L signaling M1_6 and the peptide inhibitor of CD40L signaling M1_9 (6-9 dimer), and a heterodimer of the peptide inhibitor of CD40L signaling M1_6 and the peptide inhibitor of CD40L signaling M1_189 (6-189 dimer). Data indicate enhanced inhibition of CD40L-induced CD86 expression by dimeric peptides relative to the monomeric peptide controls.
FIG. 7d is a graphical representation showing percentage inhibition of CD40L-induced CD86 expression on primary B-cells by a heterodimer of the peptide inhibitor of CD40L signaling M1_6 and the peptide inhibitor of CD40L signaling M1_9 (6-9 dimer) relative to a control monomer peptide consisting of the M1-6S monomeric peptide unit or the cysteine-containing derivative thereof. Cys-M1_6S. $EC_{50}$ values are also indicated for each peptide. Data indicate enhanced inhibition of CD40L-induced CD86 expression by dimeric peptide relative to the monomeric peptide controls.
FIG. 7e is a graphical representation showing percentage inhibition of CD40L-induced CD86 expression on primary B-cells by a heterodimer of the peptide inhibitor of CD40L signaling M1_6 and the peptide inhibitor of CD40L signaling M1_189 (6-189 dimer) relative to a control monomer peptide consisting of the M1-65 monomeric peptide unit or the cysteine-containing derivative thereof. Cys-M1_6S. $EC_{50}$ values are also indicated for each peptide. Data indicate enhanced inhibition of CD40L-induced CD86 expression by dimeric peptide relative to the monomeric peptide controls.
Figure 7:
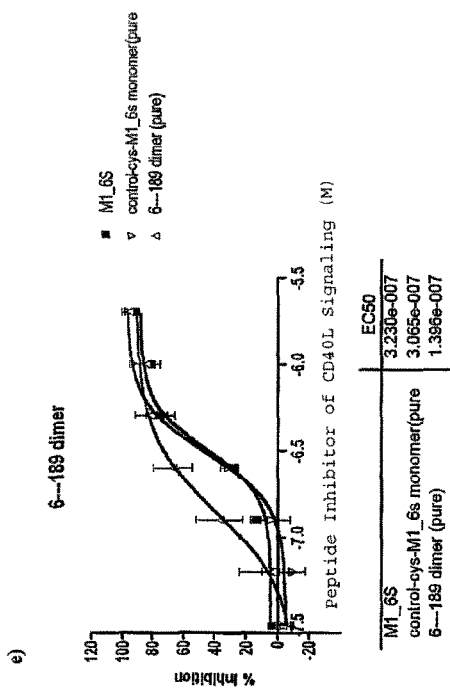

Representative data presented in Table 6, and in FIGS. 6a and 6b demonstrate the ability of the monomeric peptide designated M1_18 to inhibit CD40L-induced expression of CD86 on primary B-cells in a concentration-dependent manner, with an IC$_{50}$ of less than 0.5 µM. Similar results were obtained for a variant of the peptide having a C-terminal serine residue i.e., peptide M1_$_{18}$S, for which the EC50 value was about 7.426×10-7 M (FIG. 5e). In contrast, a control peptide that does not function as a peptidyl inhibitor of the invention failed to provide significant concentration-dependent inhibition at micromolar concentrations (FIG. 6c). In these assays, CD40L induced CD86 expression in a concentration-dependent manner in the absence of a peptidyl inhibitor of the present invention with an EC$_{50}$ value of about 9 nM (FIG. 6d, 6e). As a control in these assays, LPS-induced expression of CD86 mediated by the Toll-like receptors TLR 2/4, and TNFα-induced cytoxicity, were also assayed to exclude effects mediated by ligands other than CD40L. As shown in FIGS. 6f and 6g, no significant inhibition of LPS-induced CD86 expression was detected for peptide M1__18S and, as shown in FIGS. 6h-6j, none of the peptides designated M1__2S, M1__4S, M1__6S, M1__7S, M1__9S or M1__18S provided significant inhibition of rTNFα-induced cytoxicity.

TABLE 6

Inhibition of CD40L-CD40 interaction by monomeric peptides as determined by inhibition of CD40L-induced CD86 expression on primary B-cells

| Peptide | EC$_{50}$ unmodified peptide (nM) | EC$_{50}$ PEGylated peptide (nM) |
|---|---|---|
| M1_6S | | 1.5 |
| M1_9S | | 180 |
| M1-18S | | 90 |
| M1_30S | | >2000 |
| M1_42S | | 5000 |
| M1_50S | | 30 |
| M1_82rd | | 470 |
| M7_206rd | | 2,000 |
| M7_217 | 2,500 | |

S denotes C-terminal serine;
Cys denotes N-terminal cysteine

In a similar series of bioassays, dimeric forms of the CD40L peptide inhibitors were also tested for their ability to inhibit or reduce CD40L-induced expression of CD86 on primary B-cells. Representative data are provided in FIGS. 7a-7e and Table 7.

TABLE 7

Enhanced inhibition of CD40L-CD40 interaction by dimeric peptides as determined by inhibition of CD40L-induced CD86 expression on primary B-cells

| Peptide | EC$_{50}$ (M) |
|---|---|
| M1_6S | 3.23 × 10-7 |
| Cys_M1_6S | 3.065 × 10-7 |
| M1_4S | 1.616 × 10-6 |

TABLE 7-continued

Enhanced inhibition of CD40L-CD40 interaction by dimeric peptides as determined by inhibition of CD40L-induced CD86 expression on primary B-cells

| Peptide | $EC_{50}$ (M) |
| --- | --- |
| M1_9S | $5.643 \times 10\text{-}7$ |
| M1-18S | $7.426 \times 10\text{-}7$ |
| M7_189S | $1.765 \times 10\text{-}7$ |
| Cys_M1_6S homodimer | $4.891 \times 10\text{-}8$ |
| Cys_M1_6S-Cys_M1_4S heterodimer | $6.121 \times 10\text{-}8$ |
| Cys_M1_6S-Cys_M1_9S heterodimer | $3.505 \times 10\text{-}8$ |
| Cys_M1_6S-Cys_M1_189S heterodimer | $1.396 \times 10\text{-}7$ |

S denotes C-terminal serine;
Cys denotes N-terminal cysteine

2. T-Cell Proliferation Assays

An antigen-specific T-cell proliferation assay was used to measure the ability of anti-CD40L-peptides to inhibit CD40L receptor activity displayed natively on the surface of T cells. Briefly, pooled DLN (consisting parathymic and pos

```
<210> SEQ ID NO 4
<211> LENGTH: 23
<212> TYPE: PRT
<213> ORGANISM: Artificial
<220> FEATURE:
<223> OTHER INFORMATION: Synthetic peptide

<400> SEQUENCE: 4

Asp Ala Ala Gly Arg Glu Phe Phe Gln Ile Ala Gly Leu Phe Ser Phe
1               5                   10                  15

Arg His His Trp Trp Gln Ala
            20

<210> SEQ ID NO 5
<211> LENGTH: 23
<212> TYPE: PRT
<213> ORGANISM: Artificial
<220> FEATURE:
<223> OTHER INFORMATION: Synthetic peptide

<400> SEQUENCE: 5

His Ser Phe Val Leu Phe Gly Val Asn Val Pro Phe Asn Ile Ile Asp
1               5                   10                  15

Phe Gln Met Arg Val Lys Cys
            20

<210> SEQ ID NO 6
<211> LENGTH: 31
<212> TYPE: PRT
<213> ORGANISM: Artificial
<220> FEATURE:
<223> OTHER INFORMATION: Synthetic peptide

<400> SEQUENCE: 6

Pro Arg Trp Val Arg Asn Arg Phe Tyr Cys Leu Phe Val Pro Ser Gly
1               5                   10                  15

Val Gln Arg Gly Gly Ile His Leu Trp Phe Ser Asn Trp Val Arg
            20                  25                  30

<210> SEQ ID NO 7
<211> LENGTH: 25
<212> TYPE: PRT
<213> ORGANISM: Artificial
<220> FEATURE:
<223> OTHER INFORMATION: Synthetic peptide

<400> SEQUENCE: 7

Ser Ile Gln Tyr His Trp Arg Tyr Ser Arg Phe Lys Tyr Tyr Phe Gln
1               5                   10                  15

Leu Ile Trp Val Tyr Tyr Cys His Val
            20                  25

<210> SEQ ID NO 8
<211> LENGTH: 23
<212> TYPE: PRT
<213> ORGANISM: Artificial
<220> FEATURE:
<223> OTHER INFORMATION: Synthetic peptide

<400> SEQUENCE: 8

Leu Leu Tyr Val Lys Val Ile Cys Phe Phe Cys Met Leu Val Gln Tyr
1               5                   10                  15

Asn Asn Phe Gln Thr Tyr Lys
            20
```

<210> SEQ ID NO 9
<211> LENGTH: 21
<212> TYPE: PRT
<213> ORGANISM: Artificial
<220> FEATURE:
<223> OTHER INFORMATION: Synthetic peptide

<400> SEQUENCE: 9

Leu Leu Leu Phe Phe Phe Ser Pro Pro Phe Ser Ile Phe Cys Phe Ser
1               5                   10                  15

Leu Thr Thr Leu Ser
            20

<210> SEQ ID NO 10
<211> LENGTH: 21
<212> TYPE: PRT
<213> ORGANISM: Artificial
<220> FEATURE:
<223> OTHER INFORMATION: Synthetic peptide

<400> SEQUENCE: 10

Pro Phe Thr Trp Arg Pro Thr Ile Phe Trp Ile Ile Gln Leu Ile Val
1               5                   10                  15

Tyr Met Arg His Phe
            20

<210> SEQ ID NO 11
<211> LENGTH: 17
<212> TYPE: PRT
<213> ORGANISM: Artificial
<220> FEATURE:
<223> OTHER INFORMATION: Synthetic peptide

<400> SEQUENCE: 11

Leu Cys Glu Met Ile Ala Ile Tyr Val Phe Leu Trp Lys Lys Val Phe
1               5                   10                  15

Leu

<210> SEQ ID NO 12
<211> LENGTH: 61
<212> TYPE: PRT
<213> ORGANISM: Artificial
<220> FEATURE:
<223> OTHER INFORMATION: Synthetic peptide

<400> SEQUENCE: 12

Arg Leu Pro Glu Thr Arg Lys Ala Gln Ala Ala Leu Ala Thr Lys Tyr
1               5                   10                  15

Gly Ile Tyr Gly Phe Cys Tyr Tyr His Tyr Trp Phe Asn Gly Arg Arg
            20                  25                  30

Ile Leu Glu Ser Pro Val Asp Ala Met Leu Glu Ser Gly Glu Pro Asp
        35                  40                  45

Phe Pro Phe Met Leu Cys Trp Ala Asn Glu Asn Trp Thr
    50                  55                  60

<210> SEQ ID NO 13
<211> LENGTH: 24
<212> TYPE: PRT
<213> ORGANISM: Artificial
<220> FEATURE:
<223> OTHER INFORMATION: Synthetic peptide

<400> SEQUENCE: 13

```
Leu Trp Arg Leu Asn Glu Trp Asn Tyr Ser Asp Ala Glu Leu Leu Ser
1               5                   10                  15

Leu Ile Glu Trp Cys Ile Asp His
            20
```

<210> SEQ ID NO 14
<211> LENGTH: 63
<212> TYPE: PRT
<213> ORGANISM: Artificial
<220> FEATURE:
<223> OTHER INFORMATION: Synthetic peptide

<400> SEQUENCE: 14

```
Leu Ala Glu His Ala Val Trp Ser Leu Lys Cys Phe Pro Asp Trp Glu
1               5                   10                  15

Trp Tyr Asn Ile Asn Ile Phe Gly Thr Asp Asp Pro Asn His Phe Trp
            20                  25                  30

Val Glu Cys Asp Gly His Gly Lys Ile Leu Phe Pro Gly Tyr Pro Glu
        35                  40                  45

Gly Tyr Tyr Glu Asn His Phe Leu His Ser Phe Glu Leu Glu Asp
    50                  55                  60
```

<210> SEQ ID NO 15
<211> LENGTH: 30
<212> TYPE: PRT
<213> ORGANISM: Artificial
<220> FEATURE:
<223> OTHER INFORMATION: Synthetic peptide

<400> SEQUENCE: 15

```
Arg Ile Glu Ser Leu Glu Gly Glu Met Trp Leu Ile Asn Pro Phe Asn
1               5                   10                  15

Gly Glu Thr Leu Asp Glu His Thr Leu Glu Val Trp Leu Lys
            20                  25                  30
```

<210> SEQ ID NO 16
<211> LENGTH: 66
<212> TYPE: PRT
<213> ORGANISM: Artificial
<220> FEATURE:
<223> OTHER INFORMATION: Synthetic peptide

<400> SEQUENCE: 16

```
Leu Asp Leu Phe Gly Asp Phe Asn Gly Leu Pro Glu Gly Ala Asp Arg
1               5                   10                  15

Thr Glu Phe Tyr Gln His Glu Gly His Trp Gln Asn Arg Met Ile Leu
            20                  25                  30

Gly Asp Ser Leu Gln Val Met Ala Ser Leu Ala Glu Arg Glu Gly Leu
        35                  40                  45

Arg Gly Lys Val Gln Cys Ile Tyr Phe Asp Pro Pro Tyr Gly Ile Lys
    50                  55                  60

Phe Asn
65
```

<210> SEQ ID NO 17
<211> LENGTH: 44
<212> TYPE: PRT
<213> ORGANISM: Artificial
<220> FEATURE:
<223> OTHER INFORMATION: Synthetic peptide

<400> SEQUENCE: 17

```
Leu Trp Pro Glu Ser Trp Gly Gly Leu Pro Pro Ala Ser Phe Phe Asp
1               5                   10                  15

Glu Leu Asp Pro Cys Ile Asn Arg His Leu Arg Tyr Pro Leu Phe Ser
            20                  25                  30

Glu Thr Phe Thr Ala Asp Leu Pro Val Gly Thr Leu
        35                  40
```

<210> SEQ ID NO 18
<211> LENGTH: 105
<212> TYPE: PRT
<213> ORGANISM: Artificial
<220> FEATURE:
<223> OTHER INFORMATION: Synthetic peptide

<400> SEQUENCE: 18

```
Leu Leu Ala Glu Gln Ala Gly Thr Leu Lys Ser Glu Leu Glu Ala Met
1               5                   10                  15

Pro Leu Gly Glu Tyr Glu His Ala Ala Arg Tyr Val Ser Glu Val Glu
            20                  25                  30

Cys Asn Trp Lys Thr Phe Ala Gly Asn Tyr Ser Glu Cys Asp His Cys
        35                  40                  45

His Ala Asn His Gln Asp Trp Ile Thr Asp Ile Glu Leu Glu Glu Ser
    50                  55                  60

Glu Leu Glu Val Asn Asp Tyr His Trp Ile Leu His Tyr Thr His Asp
65                  70                  75                  80

Glu Asp Val Glu Asp Glu Met Arg Ile His Asp Glu His Gly Ala Lys
                85                  90                  95

Phe Tyr Tyr Phe Trp Pro Asn Phe Thr
            100                 105
```

<210> SEQ ID NO 19
<211> LENGTH: 18
<212> TYPE: PRT
<213> ORGANISM: Artificial
<220> FEATURE:
<223> OTHER INFORMATION: Synthetic peptide

<400> SEQUENCE: 19

```
His Pro Phe Ser Ile Lys Asn Val Phe Ser Ile Trp Asn Phe Phe Ser
1               5                   10                  15

Val Tyr
```

<210> SEQ ID NO 20
<211> LENGTH: 23
<212> TYPE: PRT
<213> ORGANISM: Artificial
<220> FEATURE:
<223> OTHER INFORMATION: Synthetic peptide

<400> SEQUENCE: 20

```
Pro Pro Arg Tyr Asn Leu Phe Phe Leu Phe Arg Phe Tyr Ser Ser Phe
1               5                   10                  15

Arg Arg Asp Tyr Leu Tyr Phe
            20
```

<210> SEQ ID NO 21
<211> LENGTH: 36
<212> TYPE: PRT
<213> ORGANISM: Artificial
<220> FEATURE:
<223> OTHER INFORMATION: Synthetic peptide

```
<400> SEQUENCE: 21

Leu Pro Phe Val Pro Tyr Arg Ser His Val Leu Lys Tyr Gly Trp Phe
1               5                   10                  15

Phe Pro Val Gln Trp Ser Ile Phe Ala Val Leu Pro Phe Gln Tyr Leu
            20                  25                  30

His Arg Ser Arg
        35

<210> SEQ ID NO 22
<211> LENGTH: 23
<212> TYPE: PRT
<213> ORGANISM: Artificial
<220> FEATURE:
<223> OTHER INFORMATION: Synthetic peptide

<400> SEQUENCE: 22

Asp Ala Ala Gly Arg Glu Phe Phe Gln Ile Ala Gly Leu Phe Ser Phe
1               5                   10                  15

Arg His His Trp Trp Gln Ala
            20

<210> SEQ ID NO 23
<211> LENGTH: 23
<212> TYPE: PRT
<213> ORGANISM: Artificial
<220> FEATURE:
<223> OTHER INFORMATION: Synthetic peptide

<400> SEQUENCE: 23

His Ser Phe Val Leu Phe Gly Val Asn Val Pro Phe Asn Ile Ile Asp
1               5                   10                  15

Phe Gln Met Arg Val Lys Ser
            20

<210> SEQ ID NO 24
<211> LENGTH: 31
<212> TYPE: PRT
<213> ORGANISM: Artificial
<220> FEATURE:
<223> OTHER INFORMATION: Synthetic peptide

<400> SEQUENCE: 24

Pro Arg Trp Val Arg Asn Arg Phe Tyr Ser Leu Phe Val Pro Ser Gly
1               5                   10                  15

Val Gln Arg Gly Gly Ile His Leu Trp Phe Ser Asn Trp Val Arg
            20                  25                  30

<210> SEQ ID NO 25
<211> LENGTH: 25
<212> TYPE: PRT
<213> ORGANISM: Artificial
<220> FEATURE:
<223> OTHER INFORMATION: Synthetic peptide

<400> SEQUENCE: 25

Ser Ile Gln Tyr His Trp Arg Tyr Ser Arg Phe Lys Tyr Tyr Phe Gln
1               5                   10                  15

Leu Ile Trp Val Tyr Tyr Ser His Val
            20                  25

<210> SEQ ID NO 26
<211> LENGTH: 23
<212> TYPE: PRT
```

```
<213> ORGANISM: Artificial
<220> FEATURE:
<223> OTHER INFORMATION: Synthetic peptide

<400> SEQUENCE: 26

Leu Leu Tyr Val Lys Val Ile Ser Phe Phe Ser Met Leu Val Gln Tyr
1               5                   10                  15

Asn Asn Phe Gln Thr Tyr Lys
            20

<210> SEQ ID NO 27
<211> LENGTH: 21
<212> TYPE: PRT
<213> ORGANISM: Artificial
<220> FEATURE:
<223> OTHER INFORMATION: Synthetic peptide

<400> SEQUENCE: 27

Leu Leu Leu Phe Phe Phe Ser Pro Pro Phe Ser Ile Phe Ser Phe Ser
1               5                   10                  15

Leu Thr Thr Leu Ser
            20

<210> SEQ ID NO 28
<211> LENGTH: 17
<212> TYPE: PRT
<213> ORGANISM: Artificial
<220> FEATURE:
<223> OTHER INFORMATION: Synthetic peptide

<400> SEQUENCE: 28

Leu Ser Glu Met Ile Ala Ile Tyr Val Phe Leu Trp Lys Lys Val Phe
1               5                   10                  15

Leu

<210> SEQ ID NO 29
<211> LENGTH: 61
<212> TYPE: PRT
<213> ORGANISM: Artificial
<220> FEATURE:
<223> OTHER INFORMATION: Synthetic peptide

<400> SEQUENCE: 29

Arg Leu Pro Glu Thr Arg Lys Ala Gln Ala Ala Leu Ala Thr Lys Tyr
1               5                   10                  15

Gly Ile Tyr Gly Phe Ser Tyr Tyr His Tyr Trp Phe Asn Gly Arg Arg
            20                  25                  30

Ile Leu Glu Ser Pro Val Asp Ala Met Leu Glu Ser Gly Glu Pro Asp
        35                  40                  45

Phe Pro Phe Met Leu Ser Trp Ala Asn Glu Asn Trp Thr
    50                  55                  60

<210> SEQ ID NO 30
<211> LENGTH: 24
<212> TYPE: PRT
<213> ORGANISM: Artificial
<220> FEATURE:
<223> OTHER INFORMATION: Synthetic peptide

<400> SEQUENCE: 30

Leu Trp Arg Leu Asn Glu Trp Asn Tyr Ser Asp Ala Glu Leu Leu Ser
1               5                   10                  15

Leu Ile Glu Trp Ser Ile Asp His
```

20

<210> SEQ ID NO 31
<211> LENGTH: 63
<212> TYPE: PRT
<213> ORGANISM: Artificial
<220> FEATURE:
<223> OTHER INFORMATION: Synthetic peptide

<400> SEQUENCE: 31

```
Leu Ala Glu His Ala Val Trp Ser Leu Lys Ser Phe Pro Asp Trp Glu
1               5                   10                  15

Trp Tyr Asn Ile Asn Ile Phe Gly Thr Asp Asp Pro Asn His Phe Trp
            20                  25                  30

Val Glu Ser Asp Gly His Gly Lys Ile Leu Phe Pro Gly Tyr Pro Glu
        35                  40                  45

Gly Tyr Tyr Glu Asn His Phe Leu His Ser Phe Glu Leu Glu Asp
    50                  55                  60
```

<210> SEQ ID NO 32
<211> LENGTH: 66
<212> TYPE: PRT
<213> ORGANISM: Artificial
<220> FEATURE:
<223> OTHER INFORMATION: Synthetic peptide

<400> SEQUENCE: 32

```
Leu Asp Leu Phe Gly Asp Phe Asn Gly Leu Pro Glu Gly Ala Asp Arg
1               5                   10                  15

Thr Glu Phe Tyr Gln His Glu Gly His Trp Gln Asn Arg Met Ile Leu
            20                  25                  30

Gly Asp Ser Leu Gln Val Met Ala Ser Leu Ala Glu Arg Glu Gly Leu
        35                  40                  45

Arg Gly Lys Val Gln Ser Ile Tyr Phe Asp Pro Tyr Gly Ile Lys
    50                  55                  60

Phe Asn
65
```

<210> SEQ ID NO 33
<211> LENGTH: 44
<212> TYPE: PRT
<213> ORGANISM: Artificial
<220> FEATURE:
<223> OTHER INFORMATION: Synthetic peptide

<400> SEQUENCE: 33

```
Leu Trp Pro Glu Ser Trp Gly Gly Leu Pro Pro Ala Ser Phe Phe Asp
1               5                   10                  15

Glu Leu Asp Pro Ser Ile Asn Arg His Leu Arg Tyr Pro Leu Phe Ser
            20                  25                  30

Glu Thr Phe Thr Ala Asp Leu Pro Val Gly Thr Leu
        35                  40
```

<210> SEQ ID NO 34
<211> LENGTH: 105
<212> TYPE: PRT
<213> ORGANISM: Artificial
<220> FEATURE:
<223> OTHER INFORMATION: Synthetic peptide

<400> SEQUENCE: 34

```
Leu Leu Ala Glu Gln Ala Gly Thr Leu Lys Ser Glu Leu Glu Ala Met
```

```
                1               5                  10                 15
            Pro Leu Gly Glu Tyr Glu His Ala Ala Arg Tyr Val Ser Glu Val Glu
                        20                  25                  30

Ser Asn Trp Lys Thr Phe Ala Gly Asn Tyr Ser Glu Ser Asp His Ser
                        35                  40                  45

His Ala Asn His Gln Asp Trp Ile Thr Asp Ile Glu Leu Glu Glu Ser
                        50                  55                  60

Glu Leu Glu Val Asn Asp Tyr His Trp Ile Leu His Tyr Thr His Asp
            65                  70                  75                  80

Glu Asp Val Glu Asp Glu Met Arg Ile His Asp Glu His Glu Ala Lys
                        85                  90                  95

Phe Tyr Tyr Phe Trp Pro Asn Phe Thr
                        100                 105

<210> SEQ ID NO 35
<211> LENGTH: 18
<212> TYPE: PRT
<213> ORGANISM: Artificial
<220> FEATURE:
<223> OTHER INFORMATION: Synthetic peptide

<400> SEQUENCE: 35

Tyr Val Ser Phe Phe Asn Trp Ile Ser Phe Val Asn Lys Ile Ser Phe
1               5                   10                  15

Pro His

<210> SEQ ID NO 36
<211> LENGTH: 23
<212> TYPE: PRT
<213> ORGANISM: Artificial
<220> FEATURE:
<223> OTHER INFORMATION: Synthetic peptide

<400> SEQUENCE: 36

Phe Tyr Leu Tyr Asp Arg Arg Phe Ser Ser Tyr Phe Arg Phe Leu Phe
1               5                   10                  15

Phe Leu Asn Tyr Arg Pro Pro
                20

<210> SEQ ID NO 37
<211> LENGTH: 36
<212> TYPE: PRT
<213> ORGANISM: Artificial
<220> FEATURE:
<223> OTHER INFORMATION: Synthetic peptide

<400> SEQUENCE: 37

Arg Cys Arg His Leu Tyr Gln Phe Pro Leu Val Ala Phe Ile Ser Trp
1               5                   10                  15

Gln Val Pro Phe Phe Trp Gly Tyr Lys Leu Val His Ser Arg Tyr Pro
                20                  25                  30

Val Phe Pro Leu
            35

<210> SEQ ID NO 38
<211> LENGTH: 23
<212> TYPE: PRT
<213> ORGANISM: Artificial
<220> FEATURE:
<223> OTHER INFORMATION: Synthetic peptide

<400> SEQUENCE: 38
```

```
Ala Gln Trp Trp His His Arg Phe Ser Phe Leu Gly Ala Ile Gln Phe
1               5                   10                  15

Phe Glu Arg Gly Ala Ala Asp
            20

<210> SEQ ID NO 39
<211> LENGTH: 23
<212> TYPE: PRT
<213> ORGANISM: Artificial
<220> FEATURE:
<223> OTHER INFORMATION: Synthetic peptide

<400> SEQUENCE: 39

Ser Lys Val Arg Met Gln Phe Asp Ile Ile Asn Phe Pro Val Asn Val
1               5                   10                  15

Gly Phe Leu Val Phe Ser His
            20

<210> SEQ ID NO 40
<211> LENGTH: 31
<212> TYPE: PRT
<213> ORGANISM: Artificial
<220> FEATURE:
<223> OTHER INFORMATION: Synthetic peptide

<400> SEQUENCE: 40

Arg Val Trp Asn Ser Phe Trp Leu His Ile Gly Gly Arg Gln Val Gly
1               5                   10                  15

Ser Pro Val Phe Leu Ser Tyr Phe Arg Asn Arg Val Trp Arg Pro
            20                  25                  30

<210> SEQ ID NO 41
<211> LENGTH: 25
<212> TYPE: PRT
<213> ORGANISM: Artificial
<220> FEATURE:
<223> OTHER INFORMATION: Synthetic peptide

<400> SEQUENCE: 41

Val His Ser Tyr Tyr Val Trp Ile Leu Gln Phe Tyr Tyr Lys Phe Arg
1               5                   10                  15

Ser Tyr Arg Trp His Tyr Gln Ile Ser
            20                  25

<210> SEQ ID NO 42
<211> LENGTH: 21
<212> TYPE: PRT
<213> ORGANISM: Artificial
<220> FEATURE:
<223> OTHER INFORMATION: Synthetic peptide

<400> SEQUENCE: 42

Phe His Arg Met Tyr Val Ile Leu Gln Ile Ile Trp Phe Ile Thr Pro
1               5                   10                  15

Arg Trp Thr Phe Pro
            20

<210> SEQ ID NO 43
<211> LENGTH: 17
<212> TYPE: PRT
<213> ORGANISM: Artificial
<220> FEATURE:
<223> OTHER INFORMATION: Synthetic peptide
```

```
<400> SEQUENCE: 43

Leu Phe Val Lys Lys Trp Leu Phe Val Tyr Ile Ala Ile Met Glu Ser
1               5                   10                  15

Leu

<210> SEQ ID NO 44
<211> LENGTH: 78
<212> TYPE: PRT
<213> ORGANISM: Artificial
<220> FEATURE:
<223> OTHER INFORMATION: Synthetic peptide

<400> SEQUENCE: 44

Pro Phe Thr Trp Arg Pro Thr Ile Phe Trp Ile Ile Gln Leu Ile Val
1               5                   10                  15

Tyr Met Arg His Phe Gly Gly Gly Gly Ser Arg Ser Glu Leu Leu Arg
                20                  25                  30

Glu Asn Ile Cys Arg Tyr Val Ser Leu Phe Asp His Pro Leu Gln Arg
            35                  40                  45

Asn Thr Pro Leu Asp Glu Leu Arg Phe Val Ile Phe Asp Thr Glu Thr
        50                  55                  60

Ser Gly Phe Asp Leu Val Lys Asp Arg Ile Leu Ser Ile Arg
65                  70                  75
```

We claim:

1. A composition comprising one or more peptides wherein the peptide comprises a sequence of amino acids other than the sequence of CD40, binds to CD40 ligand (CD40L), partially or completely inhibits interaction of CD40 with CD40L and one or more CD40-CD40L costimulatory effects and comprises a sequence selected from the group consisting of:

(i) a sequence set forth in any one of SEQ ID NOs: 1, 2, 5, 7, 19, 20, 23, 25, 35, 36, 39, 41 and 42;

(ii) a sequence of a peptidyl fusion comprising a plurality of sequences at (i); and (iii) a sequence of (i) additionally comprising a protein transduction domain.

2. The composition of claim 1, wherein the peptide that binds to CD40L and partially or completely inhibits interaction of CD40 with CD40L and one or more CD40-CD40L costimulatory effects comprises a sequence encoded by a nucleic acid fragment of a prokaryote genome or a compact eukaryote genome.

3. The composition of claim 2, wherein the peptide comprises a sequence of a natural open reading frame of a prokaryote genome or a compact eukaryote genome.

4. The composition of claim 1, wherein the peptide that binds CD40L and partially or completely inhibits interaction of CD40 with CD40L and one or more CD40-CD40L costimulatory effects is cysteine-free.

5. The composition of claim 1, wherein the peptide that binds CD40L and partially or completely inhibits interaction of CD40 with CD40L and one or more CD40-CD40L costimulatory effects comprises one or more D amino acids.

6. The composition of claim 1, wherein the peptide that binds CD40L and partially or completely inhibits interaction of CD40 with CD40L and one or more CD40-CD40L costimulatory effects is a retroinverso peptide analog.

7. The composition of claim 1, wherein the peptide that binds to CD40L and partially or completely inhibits interaction of CD40 with CD40L, and one or more CD40-CD40L costimulatory effects is a peptidyl-fusion between a plurality of smaller peptides that each bind CD40L, wherein the peptidyl-fusion has a higher affinity for CD40L and/or enhanced inhibitory activity than a single peptide of the peptidyl-fusion.

8. The composition of claim 7, wherein the peptidyl-fusion is a dimer comprising two peptides that each bind CD40L and partially or completely inhibits interaction of CD40 with CD40L and one or more CD40-CD40L costimulatory effects.

9. The composition of claim 1, wherein the peptide that binds to CD40L and partially or completely inhibits interaction of CD40 with CD40L and one or more CD40-CD40L costimulatory effects is a peptidyl-fusion between the peptide that binds CD40L and a serum protein-binding moiety or serum protein moiety.

10. The composition of claim 1, wherein the peptide that binds to CD40L and partially or completely inhibits interaction of CD40 with CD40L and one or more CD40-CD40L costimulatory effects is a peptidyl-fusion between the peptide that binds CD40L and a protein transduction domain.

11. The composition of claim 1, wherein the peptide that binds to CD40L and partially or completely inhibits interaction of CD40 with CD40L and one or more CD40-CD40L costimulatory effects comprises a polyethylene glycol (PEG) moiety, a hydroxyetheyl starch (HES) moiety, or a polyglycine moiety.

12. The composition of claim 1 comprising a pharmaceutically acceptable carrier and/or excipient.

13. A method of treating one or more adverse consequences of CD40L-dependent signaling in a subject in need thereof, said method comprising administering an amount of the composition of claim 1 for a time and under conditions sufficient to inhibit inappropriate CD40L-dependent signaling.

14. A method of treating inflammation mediated by adverse consequences of CD40L-dependent signaling in a subject in need thereof, said method comprising administering an amount of the composition of claim 1 for a time and under conditions sufficient to ameliorate one or more adverse effects of CD40L-dependent signaling that contribute to an inflammatory response in a subject.

15. A method of treating autoimmunity mediated by adverse consequences of CD40L-dependent signaling in a subject in need thereof, said method comprising administering an amount of the composition of claim 1 for a time and under conditions sufficient to ameliorate one or more adverse effects of CD40L-dependent signaling that contribute to autoimmunity in a subject.

16. A method of treating a CD40-expressing cancer or metastatic disease in a subject in need thereof, said method comprising administering an amount of the composition of claim 1 for a time and under conditions sufficient to ameliorate one or more adverse effects of CD40L-dependent signaling that contribute to cancer in a subject.

17. A method of reducing humoral immunity against a therapeutic protein that has been administered to a subject in treatment of a disease or condition, wherein said humoral immunity is mediated by adverse consequences of CD40L-dependent signaling in the subject, said method comprising administering an amount of the composition of claim 1 for a time and under conditions sufficient to ameliorate one or more adverse effects of CD-40L dependent signaling that contribute to the humoral immunity and thereby attenuating or reducing humoral immunity against the therapeutic protein administered to the subject.

18. The method of claim 17 further comprising administering the therapeutic protein to the subject.

* * * * *